United States Patent
Aljuri et al.

(10) Patent No.: US 12,324,641 B2
(45) Date of Patent: Jun. 10, 2025

(54) ARTIFICIAL INTELLIGENCE FOR ROBOTIC SURGERY

(71) Applicant: PROCEPT BioRobotics Corporation, San Jose, CA (US)

(72) Inventors: Nikolai Aljuri, Hillsborough, CA (US); Surag Mantri, East Palo Alto, CA (US); Kevin Staid, Lowell, MA (US)

(73) Assignee: PROCEPT BioRobotics Corporation, San Jose, CA (US)

( * ) Notice: Subject to any disclaimer, the term of this patent is extended or adjusted under 35 U.S.C. 154(b) by 0 days.

(21) Appl. No.: 18/593,464

(22) Filed: Mar. 1, 2024

(65) Prior Publication Data

US 2024/0277427 A1     Aug. 22, 2024

Related U.S. Application Data

(63) Continuation of application No. 17/250,230, filed as application No. PCT/US2019/038574 on Jun. 21, 2019, now Pat. No. 11,963,729.

(Continued)

(51) Int. Cl.
*A61B 34/30* (2016.01)
*A61B 34/10* (2016.01)

(52) U.S. Cl.
CPC ............ *A61B 34/30* (2016.02); *A61B 34/10* (2016.02); *A61B 2034/104* (2016.02); *A61B 2034/107* (2016.02); *A61B 2034/108* (2016.02)

(58) Field of Classification Search
CPC ... A61B 34/30; A61B 34/10; A61B 2034/104; A61B 2034/107; A61B 2034/108;

(Continued)

(56) References Cited

U.S. PATENT DOCUMENTS

| | | | |
|---|---|---|---|
| 4,742,815 A | 5/1988 | Ninan | |
| 6,863,654 B2 * | 3/2005 | Zappala | A61B 1/307 |
| | | | 600/439 |

(Continued)

FOREIGN PATENT DOCUMENTS

| | | |
|---|---|---|
| CN | 101795636 | 8/2010 |
| CN | 103796607 | 5/2014 |

(Continued)

OTHER PUBLICATIONS

"Clinical Guideline for Benign Prostatic Hyperplasia," The Japanese Urological Association, pp. 115-116, 125-127, RichHill Medical Inc., machine translation (Apr. 2011).

(Continued)

*Primary Examiner* — Juan A Torres

(74) *Attorney, Agent, or Firm* — FisherBroyles, LLP; John K. Shimmick

(57) ABSTRACT

An apparatus for robotic surgery comprises a processor configured with instructions to receive patient data from treated patients, receive surgical robotics data for each of the plurality of treated patients, and output a treatment plan of a patient to be treated in response to the patient data and the surgical robotics data. This approach has the advantage of accommodating individual variability among patients and surgical system parameters so as to provide improved treatment outcomes.

20 Claims, 70 Drawing Sheets

Related U.S. Application Data

(60) Provisional application No. 62/688,349, filed on Jun. 21, 2018.

(58) Field of Classification Search
CPC ............... A61B 18/1492; A61B 90/30; A61B 2017/00725; A61B 2018/00285; A61B 2018/00547; A61B 2018/00577; A61B 2034/2048; A61B 2034/2059; G16H 20/40; G16H 40/63; G16H 50/20
USPC ........................................................ 606/130
See application file for complete search history.

(56) References Cited

U.S. PATENT DOCUMENTS

| | | | |
|---|---|---|---|
| 8,152,816 | B2 | 4/2012 | Tuma |
| 8,229,188 | B2 | 7/2012 | Rusko |
| 9,144,461 | B2 | 9/2015 | Kruecker |
| 9,277,969 | B2 | 3/2016 | Brannan |
| 9,364,251 | B2 * | 6/2016 | Aljuri ................ A61B 18/1485 |
| 9,549,739 | B2 * | 1/2017 | Catanese, III ..... A61B 17/1227 |
| 9,724,069 | B2 * | 8/2017 | Neuberger ........... A61B 8/0841 |
| 9,867,635 | B2 | 1/2018 | Alvarez |
| 10,226,298 | B2 | 3/2019 | Ourselin |
| 10,420,616 | B2 | 9/2019 | Kostrzewski |
| 10,423,757 | B2 | 9/2019 | Kruecker |
| 10,448,956 | B2 | 10/2019 | Gordon |
| 11,278,451 | B2 | 3/2022 | Andrews |
| 11,963,729 | B2 | 4/2024 | Aljuri |
| 2002/0040220 | A1 | 4/2002 | Zvuloni |
| 2007/0014454 | A1 | 1/2007 | Sawyer |
| 2008/0027420 | A1 | 1/2008 | Wang |
| 2008/0262486 | A1 | 10/2008 | Zvuloni |
| 2010/0305439 | A1 | 12/2010 | Shai |
| 2011/0015628 | A1 | 1/2011 | Dalal |
| 2011/0026786 | A1 | 2/2011 | Mohamed |
| 2011/0184391 | A1 | 7/2011 | Aljuri |
| 2012/0277763 | A1 | 11/2012 | Greenblatt |
| 2013/0090554 | A1 | 4/2013 | Zvuloni |
| 2013/0317353 | A1 | 11/2013 | Frank |
| 2013/0317363 | A1 | 11/2013 | Case |
| 2014/0303659 | A1 | 10/2014 | Aljuri |
| 2014/0309649 | A1 | 10/2014 | Alvarez |
| 2015/0025539 | A1 | 1/2015 | Alvarez |
| 2015/0335344 | A1 | 11/2015 | Aljuri |
| 2016/0058517 | A1 | 3/2016 | Kim |
| 2016/0150952 | A1 | 6/2016 | Raymond |
| 2017/0035611 | A1 | 2/2017 | Dai |
| 2017/0143428 | A1 | 5/2017 | Raffy |
| 2017/0273797 | A1 | 9/2017 | Gordon |
| 2018/0028261 | A1 | 2/2018 | Chen |
| 2018/0318011 | A1 | 11/2018 | Leibinger |
| 2019/0201214 | A1 | 7/2019 | Miller |
| 2019/0254759 | A1 | 8/2019 | Azizian |
| 2019/0262084 | A1 | 8/2019 | Roh |
| 2019/0282301 | A1 | 9/2019 | Bonillas Vaca |
| 2022/0293013 | A1 | 9/2022 | Hannaford |
| 2022/0415006 | A1 | 12/2022 | Donhowe |

FOREIGN PATENT DOCUMENTS

| | | |
|---|---|---|
| CN | 104203078 | 12/2014 |
| CN | 104582624 | 4/2015 |
| CN | 105997245 | 10/2016 |
| CN | 107997821 | 5/2018 |
| CN | 118750165 | 10/2024 |
| EP | 1486900 | 12/2004 |
| JP | 2015509789 | 4/2015 |
| WO | 2008083407 | 7/2008 |
| WO | 2009111736 | 9/2009 |
| WO | 2011097505 A1 | 8/2011 |
| WO | 2013053614 | 4/2013 |
| WO | 2013130895 A1 | 9/2013 |
| WO | 2014127242 A2 | 8/2014 |
| WO | 2014165703 A1 | 10/2014 |
| WO | 2015035249 A2 | 3/2015 |
| WO | 2015200538 A1 | 12/2015 |
| WO | 2016004071 A1 | 1/2016 |
| WO | 2016037132 A1 | 3/2016 |
| WO | 2016037137 A1 | 3/2016 |
| WO | 2017161331 A1 | 9/2017 |
| WO | 2018048753 | 3/2018 |
| WO | 2018092071 | 5/2018 |
| WO | 2019032986 | 2/2019 |
| WO | 2019137665 | 7/2019 |
| WO | 2019143635 | 7/2019 |
| WO | 2019204777 | 10/2019 |
| WO | 2019226440 | 11/2019 |
| WO | 2019246580 | 12/2019 |
| WO | 2020117561 | 6/2020 |
| WO | 2020180724 | 9/2020 |
| WO | 2020181278 | 9/2020 |
| WO | 2020181280 | 9/2020 |
| WO | 2020181281 | 9/2020 |
| WO | 2020181290 | 9/2020 |

OTHER PUBLICATIONS

Amended claims filed after receipt of (European) search report dated Sep. 22, 2022 for EP 19821567. NPL2 (Year: 2022).

Amendments received before examination dated Sep. 22, 2022 for EP 19821567. NPL3 (Year: 2022).

International Search Report and Written Opinion for International Patent Application No. PCT/US2019/038574, 16 pages (Oct. 29, 2019).

The Japanese Urological Association, Clinical Guideline for Benign Prostatic Hyperplasia, p. 115-116, 125-127, Japan, Publisher: Rich-Hill Medical Inc., https://222.urol.or.jp.lib/files/other/guideline/08_prostatic_hyperplasica.pdf, 301 pages including English machine translation (Jun. 25, 2011).

Macrae, C., Gilling, P., How I do it: Aquablation of the prostate using the AquaBeam system. Can U Urol 23 (6):8590-8593 (2016).

AquaBeam System, Instructions for Use (US), provided beginning on Jan. 25, 2018, with products that were sold, not available to public.

AquaBeam System, Instructions for Use (US), provided beginning on Jul. 12, 2018, with products that were sold, not available to public.

AquaBeam System, Instructions for Use (US), provided beginning on Mar. 27, 2019, with products that were sold, not available to public.

* cited by examiner

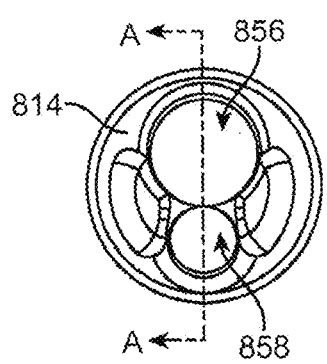
FIG. 8E1
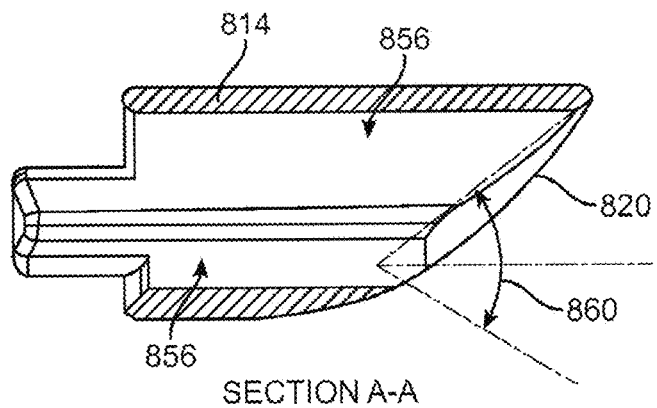
SECTION A-A
FIG. 8E2
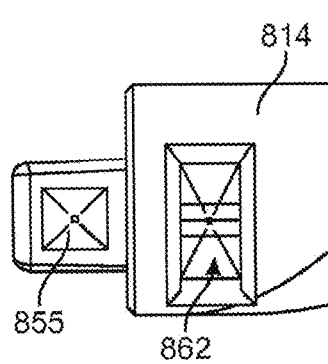
FIG. 8E3
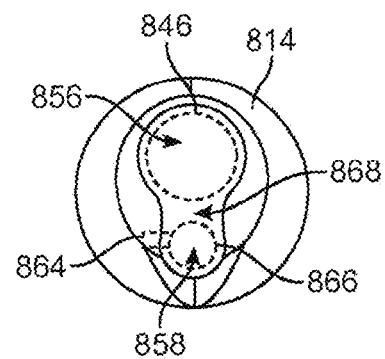
FIG. 8E4

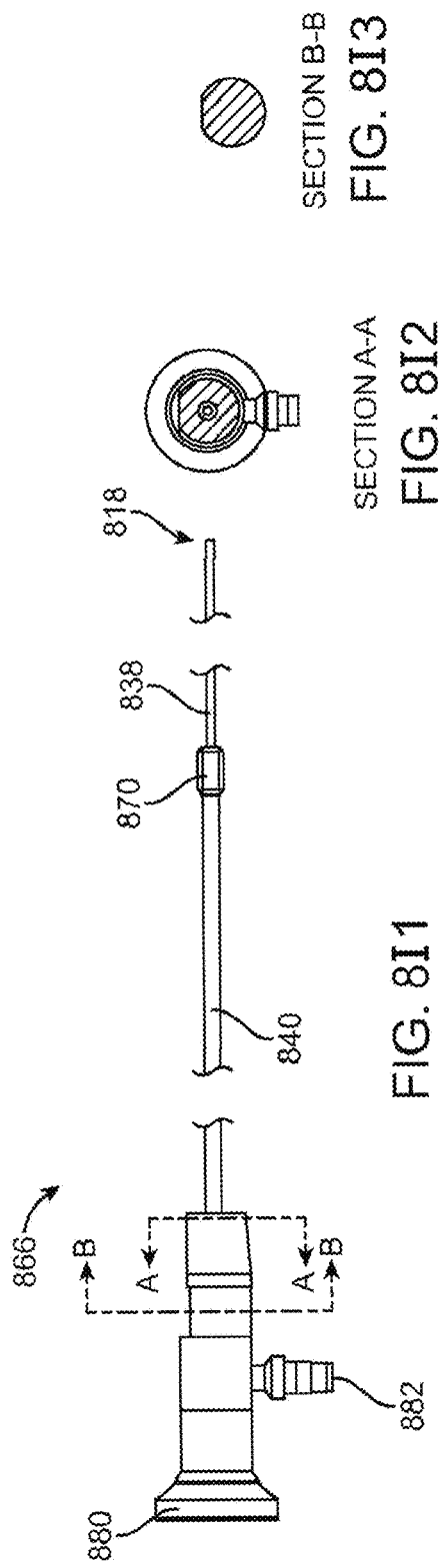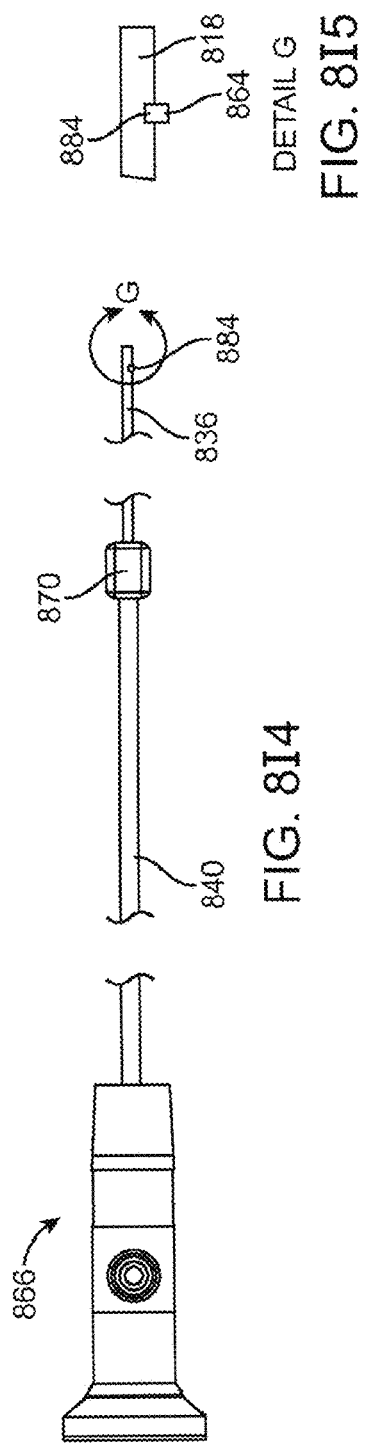

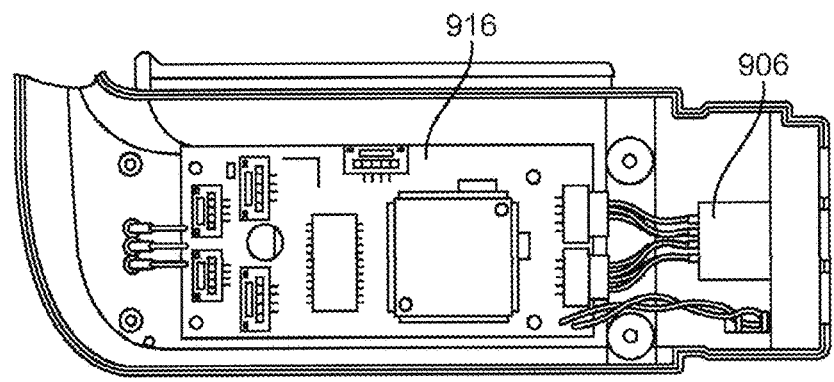
FIG. 8O1
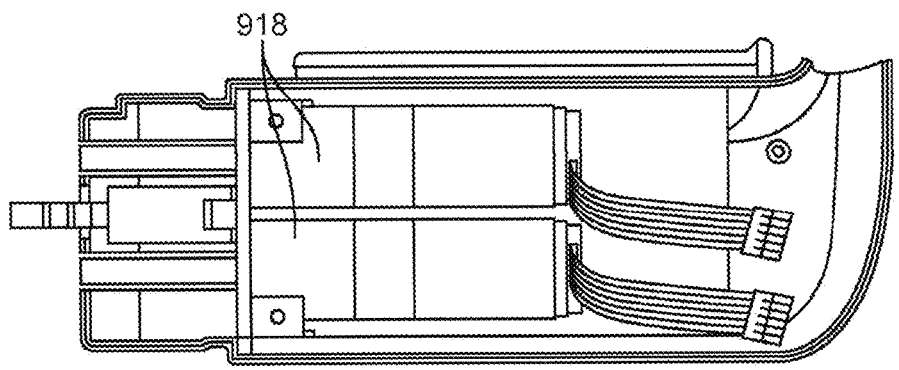
FIG. 8O2

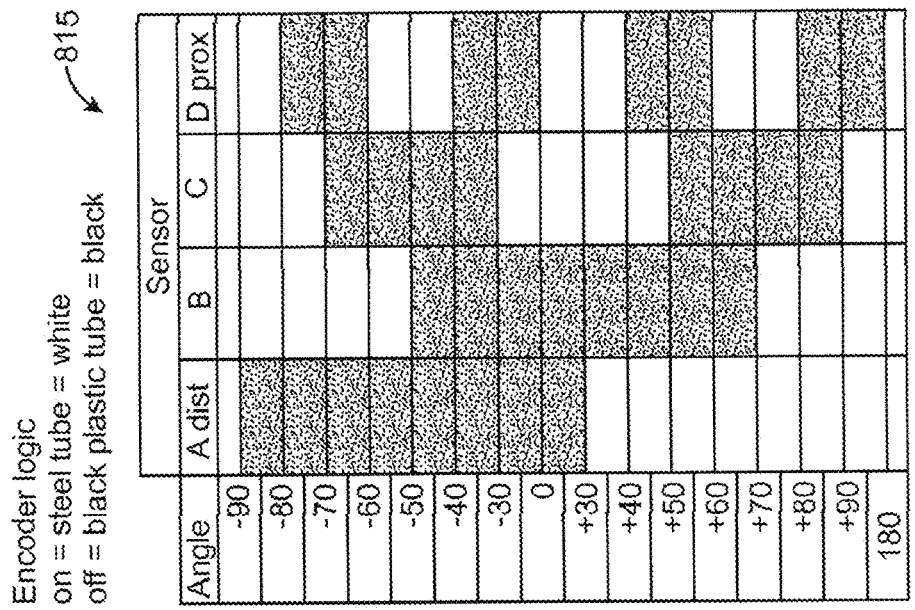
FIG. 8R2
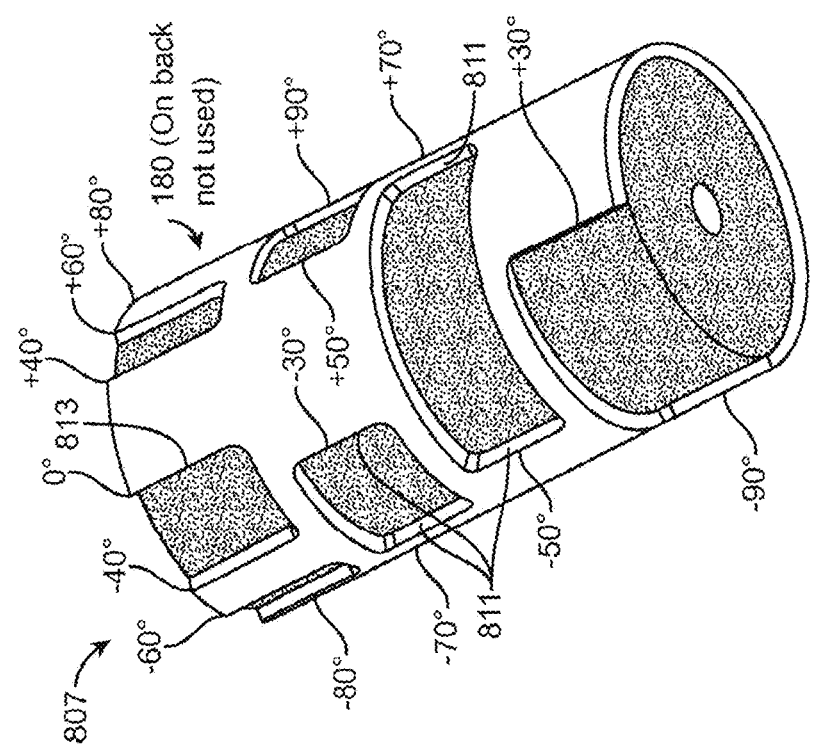
FIG. 8R1

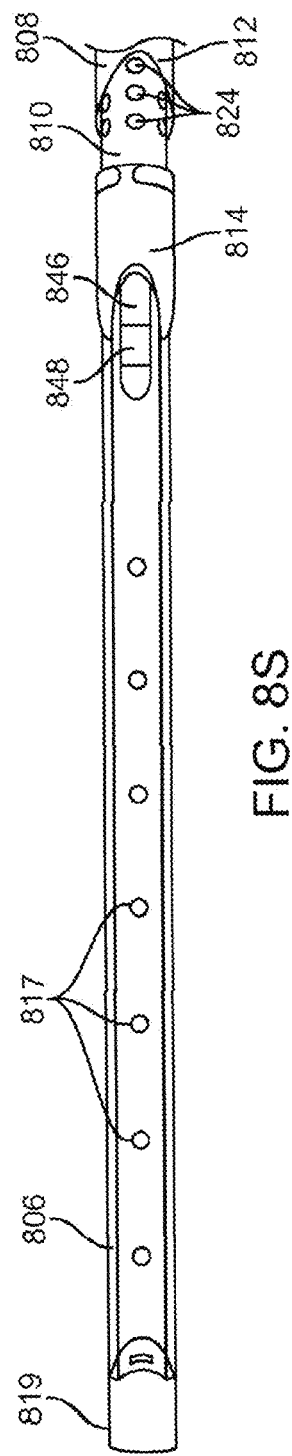

FIG. 10R

ARTIFICIAL INTELLIGENCE FOR ROBOTIC SURGERY

CROSS-REFERENCE

This application is a continuation of U.S. patent application Ser. No. 17/250,230, filed Dec. 18, 2020, now U.S. Pat. No. 11,963,729, issued Apr. 23, 2024, which is a 371 national phase of PCT/US2019/038574, filed Jun. 21, 2019, published as WO 2019/246580 on Dec. 26, 2019, and claims the benefit under 35 U.S.C. § 119(e) of U.S. Provisional Application No. 62/688,349, filed Jun. 21, 2018, the disclosures of which are incorporated, in their entirety, by this reference.

The subject matter of this application is related to International Application No. PCT/US2015/048695, filed Sep. 4, 2015, published as WO 2016/037137 on Mar. 10, 2016, International Application No. PCT/US2015/048687, filed Sep. 4, 2015, published as WO 2016/037132 on Mar. 10, 2016; International Application No. PCT/US2015/038605, filed on Jun. 30, 2015, published as WO 2016/004071 on Jan. 7, 2016; International Application No. PCT/US2015/037521, filed Jun. 24, 2015, published as WO 2015/200538 on Dec. 30, 2015; and International Application No. PCT/US2014/054412, filed Sep. 5, 2014 published as WO 2015/035249 on Mar. 12, 2015, which are hereby incorporated herein by reference in their entirety.

BACKGROUND

Surgical robotics has led to new surgical procedures and improvements to prior surgical procedures. However, prior methods and apparatus for robotic surgery can be less than ideal in at least some respects. For example, prior approaches may less than ideally address individual variability, such as tissue ablation rates and healing. Also, additional factors such as surgical set up time and treatment time can be related to outcomes and may be less than ideally addressed with the prior methods an apparatus.

At least some prior surgical procedures can be less than ideally suited to customize the surgical procedure to the specific desires of an individual patient. For example with prostate surgery such as surgery for benign prostate hyperplasia (BPH), there can be a tradeoff between the efficacy of the procedure and possible side effects. Surgery of the prostate can involve cutting or ablating BPH tissue near delicate tissue structures such as the verumontanum, which is typically critical for male sexual function. Work in relation to the present disclosure suggests that it may be helpful to determine the locations and amounts of BPH tissue to be removed in relation to patient specific preferences.

In light of the above, improved methods and apparatus for surgical procedures would be helpful. Ideally, such methods and apparatus would improve at least some of the shortcomings of the prior procedures.

SUMMARY

In a first aspect, an apparatus for robotic surgery comprises a processor configured with instructions to receive patient data from treated patients, receive surgical robotics data for each of the plurality of treated patients, and output a treatment plan of a patient to be treated in response to the patient data and the surgical robotics data. This approach has the advantage of accommodating individual variability among patients and surgical system parameters so as to provide improved treatment outcomes.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 8E1-8E4 show the coupling in accordance with some embodiments;

FIG. 8I1 shows a side view of the endoscope in accordance with some embodiments;

FIG. 8I2 shows a side view along section AA as in FIG. 8I1;

FIG. 8I3 shows section BB of the endoscope of FIG. 8I1;

FIG. 8I4 shows a top view of the endoscope as in FIG. 8I1;

FIG. 8I5 shows a distal end of the endoscope as in FIG. 8I1;

FIG. 8O1 and FIG. 8O2 show internal structures of the arm components shown in FIG. 8N;

FIG. 8R1 shows an encoder in accordance with some embodiments;

FIG. 8R2 shows a table showing coordinate references for different transitions measured with a plurality of photo detectors;

FIG. 8S shows aspiration ports on the distal end of the support in accordance with some embodiments;

DETAILED DESCRIPTION

Figure 1:
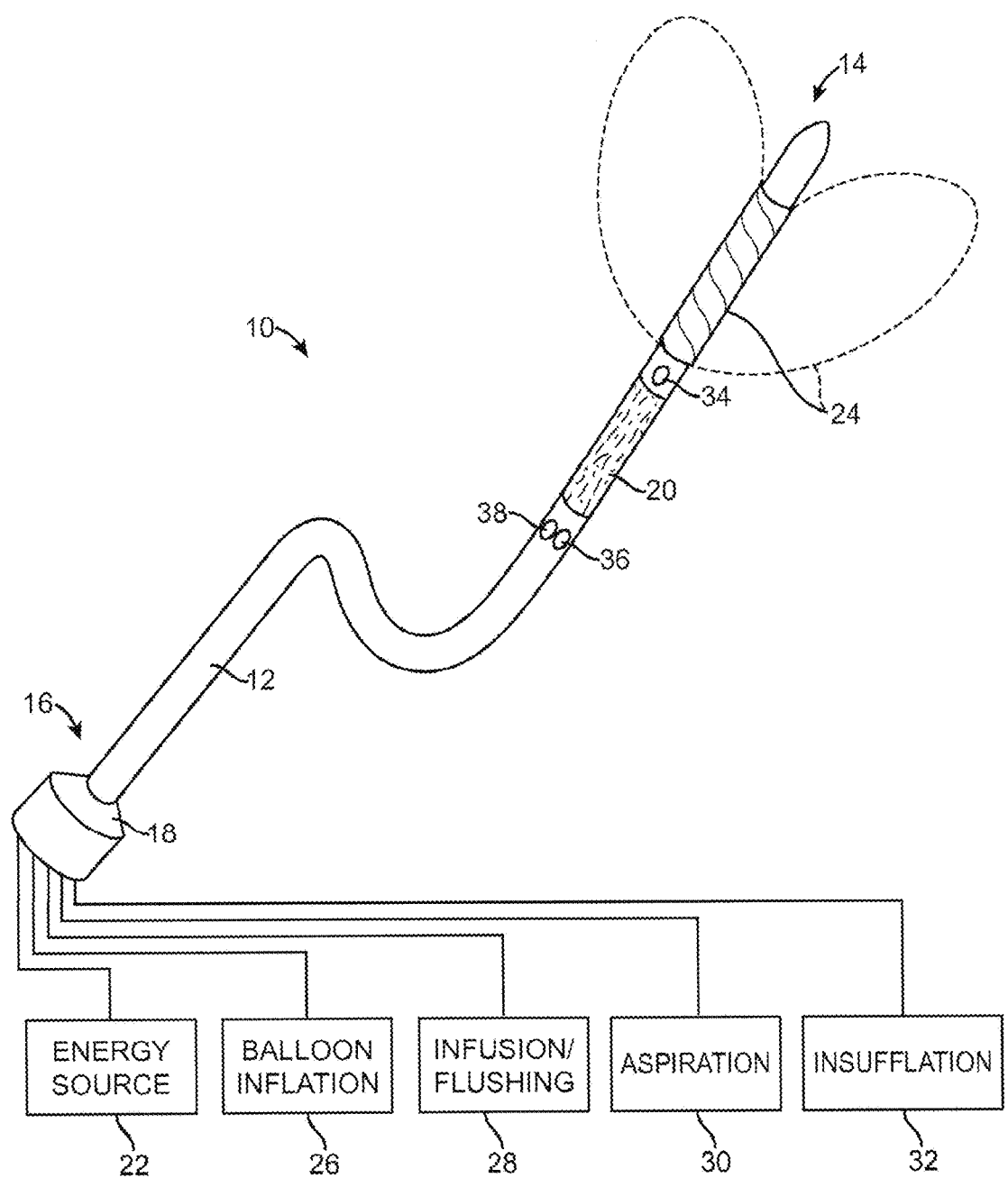
FIG. 1 is a schematic illustration of a device suitable for performing intraurethral prostatic tissue debulking in accordance with some embodiments.

The presently disclosed methods and apparatus are well suited for combination with many types of surgery such as a prostate surgery and related methods and apparatus. The methods and apparatus disclosed herein can be used to determine suitable treatment parameters, and are suitable for combination with devices that use energy used to treat the prostate such as mechanical energy, radiation therapy, water jet treatment, radiation treatment, laser ablation, and combination thereof. The presently disclosed methods and apparatus can be used with surgical robotics systems with treatment image guidance, multi-dimensional imaging, autonomous robots, and ablation such as heat free water jet ablation. The presently disclosed methods and apparatus can be used to improve many types of surgical robotics procedures, such as joint based robotics systems, rotating and oscillating shaft systems, and systems comprising joints capable of mimicking human movement in response to user input. These systems can rely on image guidance in which surgical parameters are input into the system prior to treatment. The systems can be set up by an operator prior to surgery.

The systems and methods disclosed herein comprise a plurality of sensors, each of which is capable of measuring recording states of the robotic system components before, during and after surgery, which can be used for analysis to improve the surgical procedures and outcomes. For example, the surgical robotics system may comprise a plurality of parameters related to the state of the system and associated components, such as an angle of a shaft, a longitudinal position of a shaft, data related to energy used to ablate tissue (e.g. pressure or irradiance), real time ultrasonic imaging, and real-time endoscopic imaging (e.g. cystoscopic imaging), for example. The data during treatment can be recorded in real time and used to generate a plurality of data frames corresponding to the state of the surgical robotics system throughout the treatment. The data frames may correspond to fixed time intervals between frames, e.g. one second, in order to provide input data suitable for processing with machine learning or artificial intelligence as described herein.

While embodiments of the present disclosure are specifically directed to treatment of the prostate, certain aspects of the disclosure may also be used to treat and modify other organs and tissue such as brain, heart, lungs, intestines, eyes, skin, kidney, liver, pancreas, stomach, uterus, ovaries, testicles, bladder, car, nose, mouth, soft tissues such as bone marrow, adipose tissue, muscle, glandular and mucosal tissue, spinal and nerve tissue, cartilage, hard biological tissues such as teeth, bone, as well as body lumens and passages such as the sinuses, ureter, colon, esophagus, lung passages, blood vessels, and throat. The devices disclosed herein may be inserted through an existing body lumen, or inserted through an opening created in body tissue.

Work in relation to embodiments suggests that input patient data such as demographic data and image data of the organ to be treated such as the prostate, can be related to outcomes, such as the cut profile of the tissue removed. Biopsy data, if available, may also be helpful in determining appropriate adjustments to a planned surgical treatment.

This input data can be generated and recorded from many types of surgical systems. The presently disclosed methods and apparatus are well suited for combination with many applications related to surgical robotics, and can incorporate the hardware, processors and software of many prior systems such as those described in PCT/US2015/048695, filed on Sep. 4, 2015, entitled "PHYSICIAN CONTROLLED TISSUE RESECTION INTEGRATED WITH TREATMENT MAPPING OF TARGET ORGAN IMAGES"; PCT/US2015/048687, filed on Sep. 4, 2015, entitled "GENE ANALYSIS AND GENERATION OF STEM CELL METHODS AND APPARATUS"; PCT/US2015/038605, filed on Jun. 30, 2015, entitled "FLUID JET TISSUE RESECTION AND COLD COAGULATION (AQUABLATION) METHODS AND APPARATUS"; PCT/US2015/037521, filed on Jun. 24, 2015, entitled "TISSUE SAMPLING AND CANCER TREATMENT METHODS AND APPARATUS"; and PCT/US2014/054412, filed on Sep. 5, 2014, entitled "AUTOMATED IMAGE-GUIDED TISSUE RESECTION AND TREATMENT"; the full disclosures of which have been previously incorporated by reference. Many of the components of the AQUABEAM SYSTEM commercially available from Procept BioRobotics are well suited for combination in accordance with the embodiments disclosed herein.

The embodiments disclosed herein can be combined in many ways to provide improved treatments to the patient. Although reference is made to some components in some figures and other components in other figures, it is contemplated that each of these components can be combined with any one or more of the other components in order to provide an improved treatment to the patient.

As used herein, the terms proximal and distal in the context of the apparatus refer to proximal and distal as referenced from the apparatus outside the patient, such that proximal may refer to components outside the patient and distal may refer to components inside the patient.

As used herein like words and characters denote like structures.

As used herein the terms "carrier probe" and "treatment probe" are used interchangeably.

As used herein the terms "ablation" and "resection" are used interchangeably.

As used herein "based on" and "in response to" are used interchangeably.

As used herein, the terms "cut profile" and "resection profile" are used interchangeably.

Figure 2A:
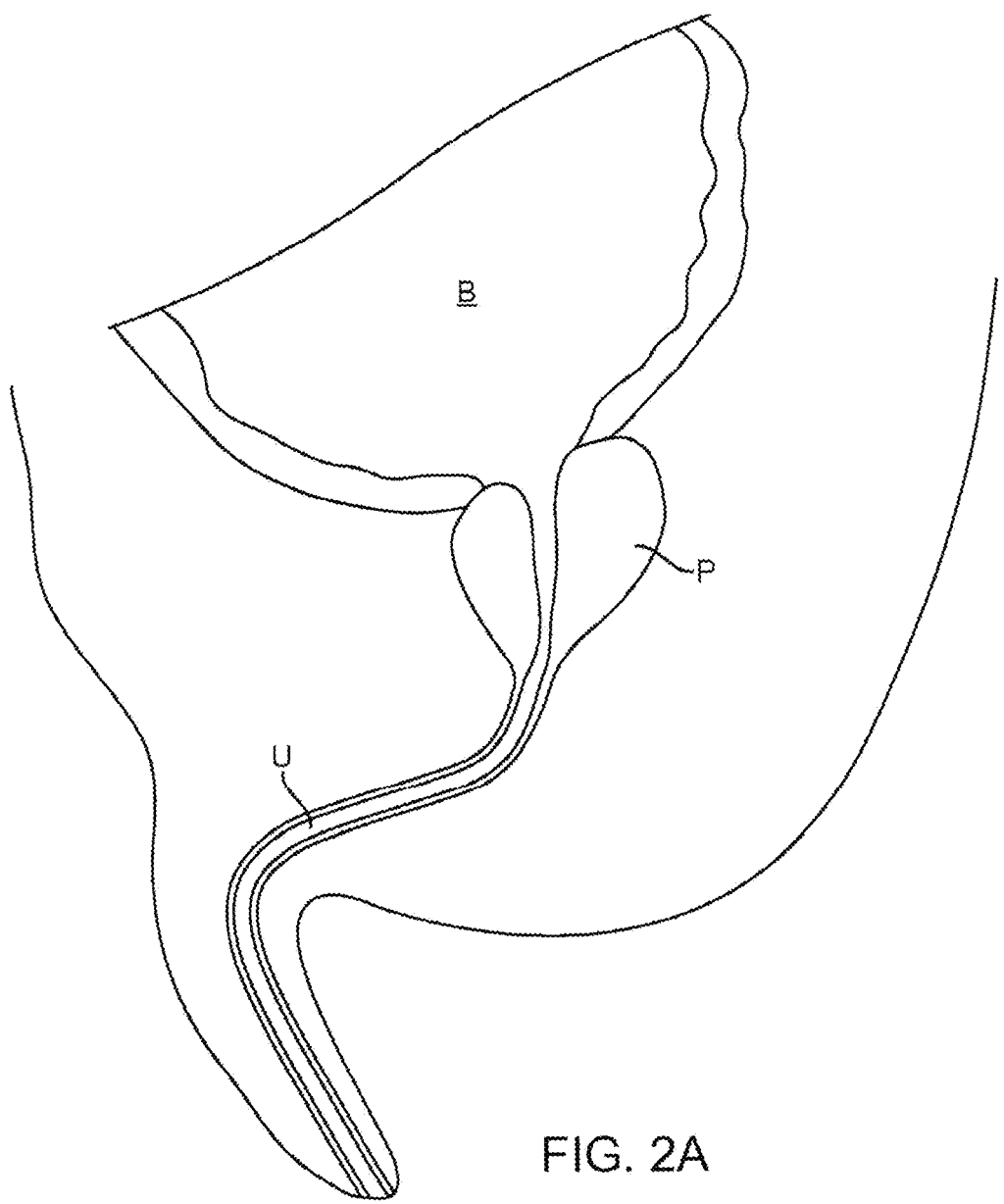
FIGS. 2A-2D illustrate use of the device of FIG. 1 in performing prostatic tissue debulking.
Figure 2B:
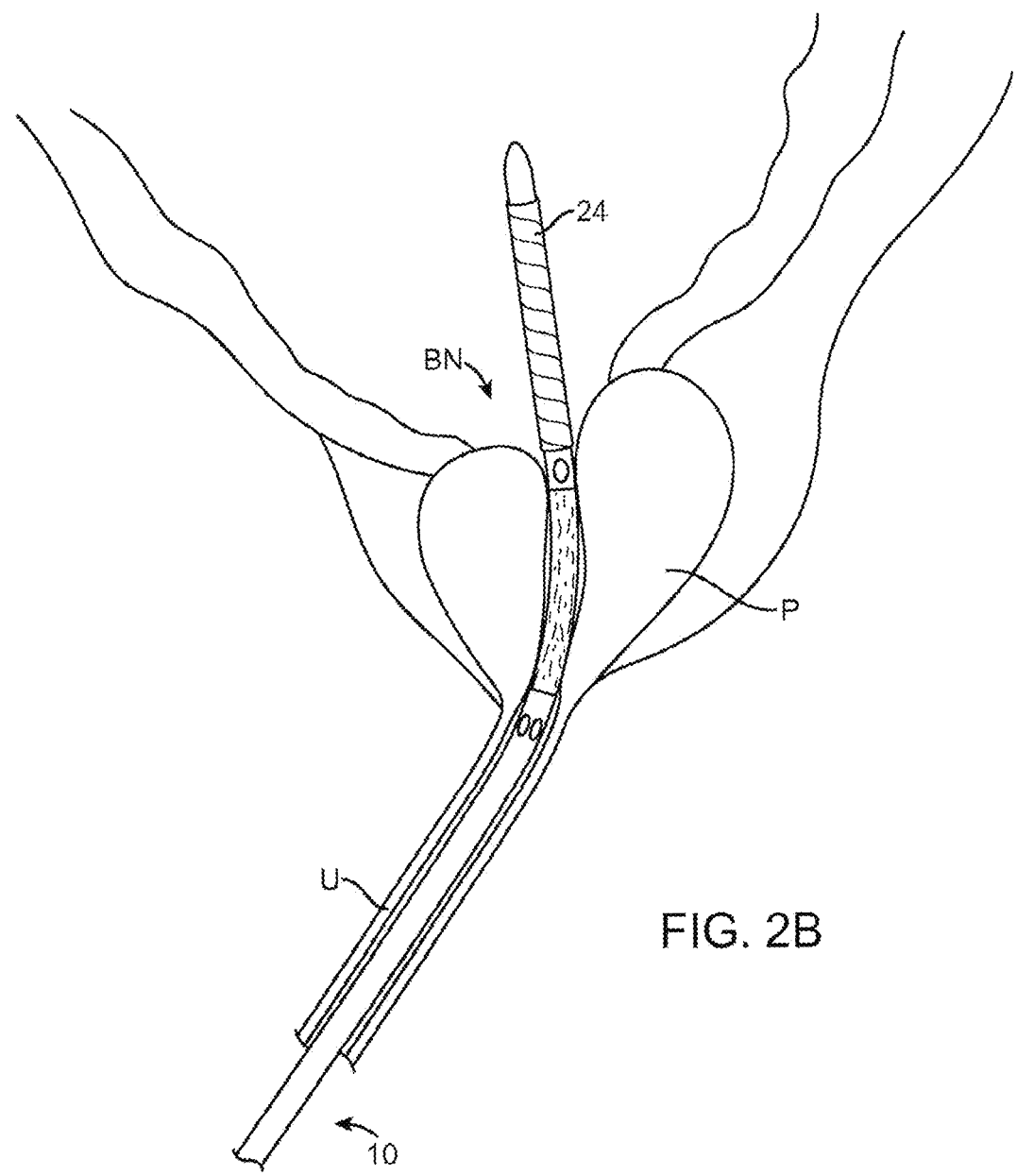
Figure 2C:
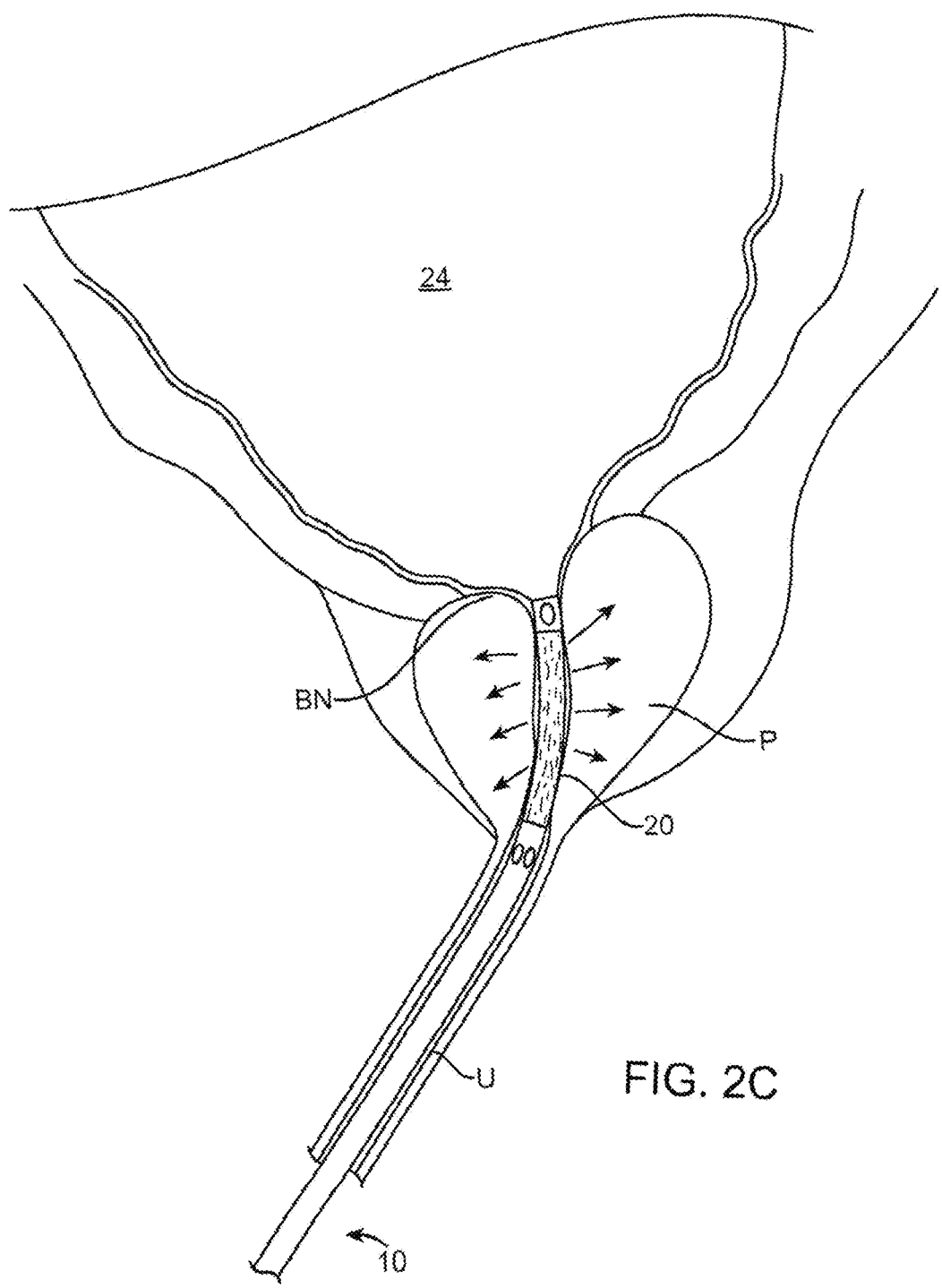
Figure 2D:
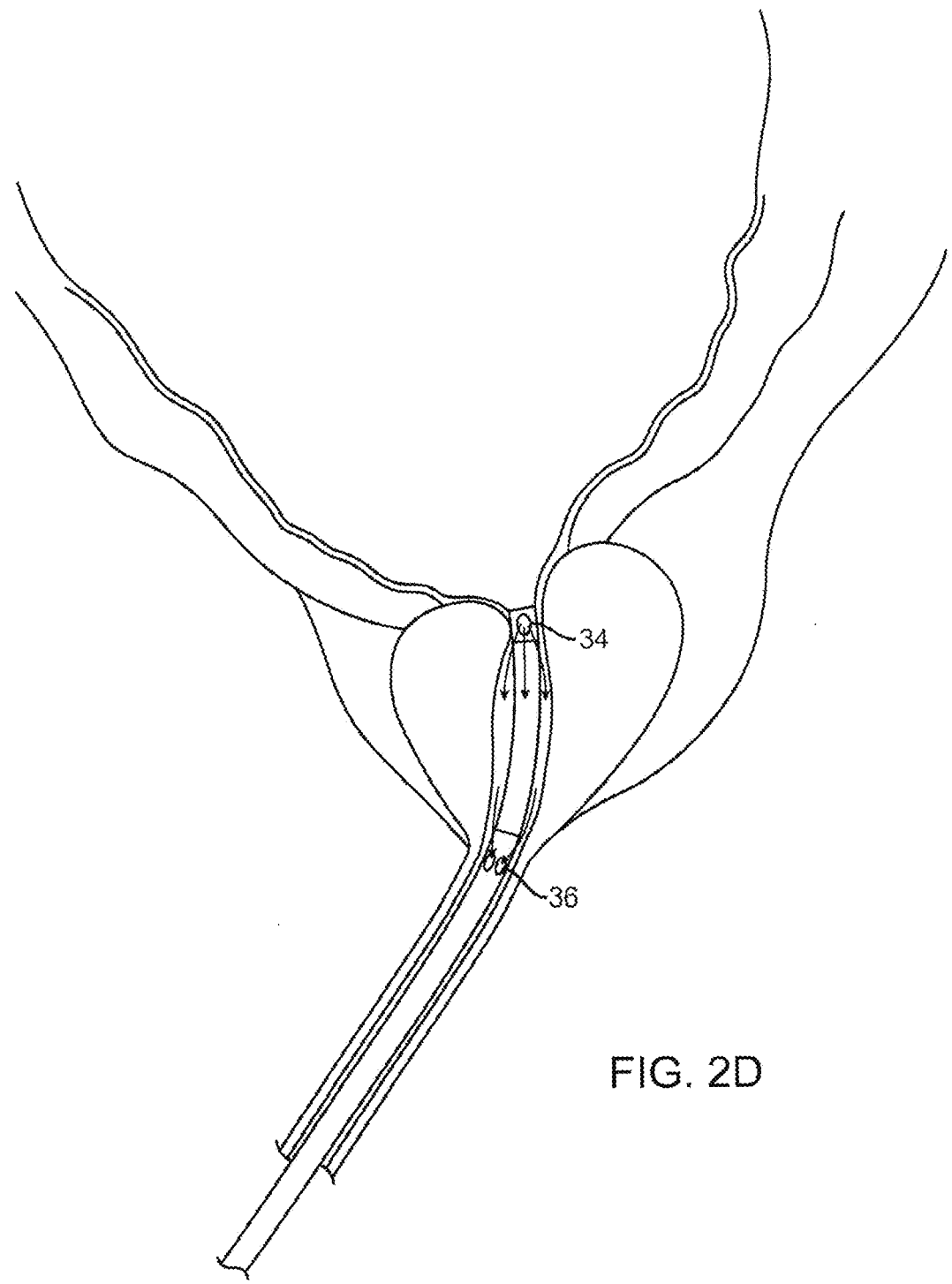

The subject matter of FIGS. 1 to 2D and the corresponding text have been incorporated by reference as described in U.S. application Ser. No. 12/700,568, filed Feb. 4, 2010, now U.S. Pat. No. 9,232,959 issued Jan. 12, 2016, and International Application No. PCT/US2011/023781, filed on Feb. 4, 2011, published as WO 2011/097505 on Nov. 8, 2011, the full disclosures of which have been previously incorporated herein by reference.

The methods and apparatus disclosed herein are well suited for combination with many commercially available surgical systems and procedures, and may comprise one or more components of surgical systems for AQUABLATION® therapy, commercially available from Procept BioRobotics Inc. CORPORATION. In some embodiments disclosed herein, a water jet immersed in saline is used to resect tissue, and referred to herein as "aqua-ablation".

Referring to FIG. 1, an exemplary prostatic tissue debulking device 10 constructed in accordance with the principles of the present invention comprises a catheter assembly generally including a shaft 12 having a distal end 14 and a proximal end 16. The shaft 12 will typically be a polymeric extrusion including one, two, three, four, or more axial lumens extending from a hub 18 at the proximal end 16 to locations near the distal end 14. The shaft 12 will generally have a length in the range from 15 cm to 25 cm and a diameter in the range from 1 mm to 10 mm, usually from 2 mm to 6 mm. The shaft will have sufficient column strength so that it may be introduced upwardly through the male urethra, as described in more detail below.

The shaft will include an energy source positioned in the energy delivery region 20, where the energy source can be any one of a number of specific components as discussed in more detail below. Distal to the energy delivery region, an inflatable anchoring balloon 24 will be positioned at or very close to the distal end 14 of the shaft. The balloon will be connected through one of the axial lumens to a balloon inflation source 26 connected through the hub 18. In addition to the energy source 22 and the balloon inflation source 26, the hub will optionally further include connections for an infusion/flushing source 28, an aspiration (a vacuum) source 30, and/or an insufflation (pressurized $CO_2$ or other gas) source 32. In the exemplary embodiment, the infusion or flushing source 28 can be connected through an axial lumen (not shown) to one or more delivery ports 34 proximal to the balloon anchor 24 and distal to the energy delivery region 20. The aspiration source 30 can be connected to a second port or opening 36, usually positioned proximally of the energy delivery region 20, while the insufflation source 32 can be connected to an additional port 38, also usually located proximal of the energy delivery region. It will be appreciated that the locations of the ports 34, 36, and 38 are not critical, although certain positions may result in particular advantages described herein, and that the lumens and delivery means could be provided by additional catheters, tubes, and the like, for example including coaxial sleeves, sheathes, and the like which could be positioned over the shaft 12.

While the present embodiments are described with reference to the human prostate, it is understood that they may be used to treat mammal prostates in general. Referring now to FIGS. 2A-2D, the prostatic tissue debulking device 10 is introduced through the male urethra U to a region within the prostate P which is located immediately distal to the bladder B. The anatomy is shown in FIG. 2A. Once the catheter 10 has been positioned so that the anchoring balloon 24 is located just distal of the bladder neck BN (FIG. 2B) the balloon can be inflated, preferably to occupy substantially the entire interior of the bladder, as shown in FIG. 2C. Once the anchoring balloon 24 is inflated, the position of the prostatic tissue debulking device 10 will be fixed and stabilized within the urethra U so that the energy delivery region 20 is positioned within the prostate P. It will be appreciated that proper positioning of the energy delivery region 20 depends only on the inflation of the anchoring balloon 24 within the bladder. As the prostate is located immediately proximal to the bladder neck BN, by spacing the distal end of the energy delivery region very close to the proximal end of the balloon, typically within the range from 0 mm to 5 mm, preferably from 1 mm to 3 mm, the delivery region can be properly located. After the anchoring balloon 24 has been inflated, energy can be delivered into the prostate for debulking, as shown by the arrows in FIG. 2. Once the energy has been delivered for a time and over a desired surface region, the energy region can be stopped and the prostate will be debulked to relieve pressure on the urethra, as shown in FIG. 2D. At that time, a flushing fluid may be delivered through port 34 and aspirated into port 36, as shown in FIG. 2D. Optionally, after the treatment, the area could be cauterized using a cauterizing balloon and/or stent which could be placed using a modified or separate catheter device.

Figure 3A:
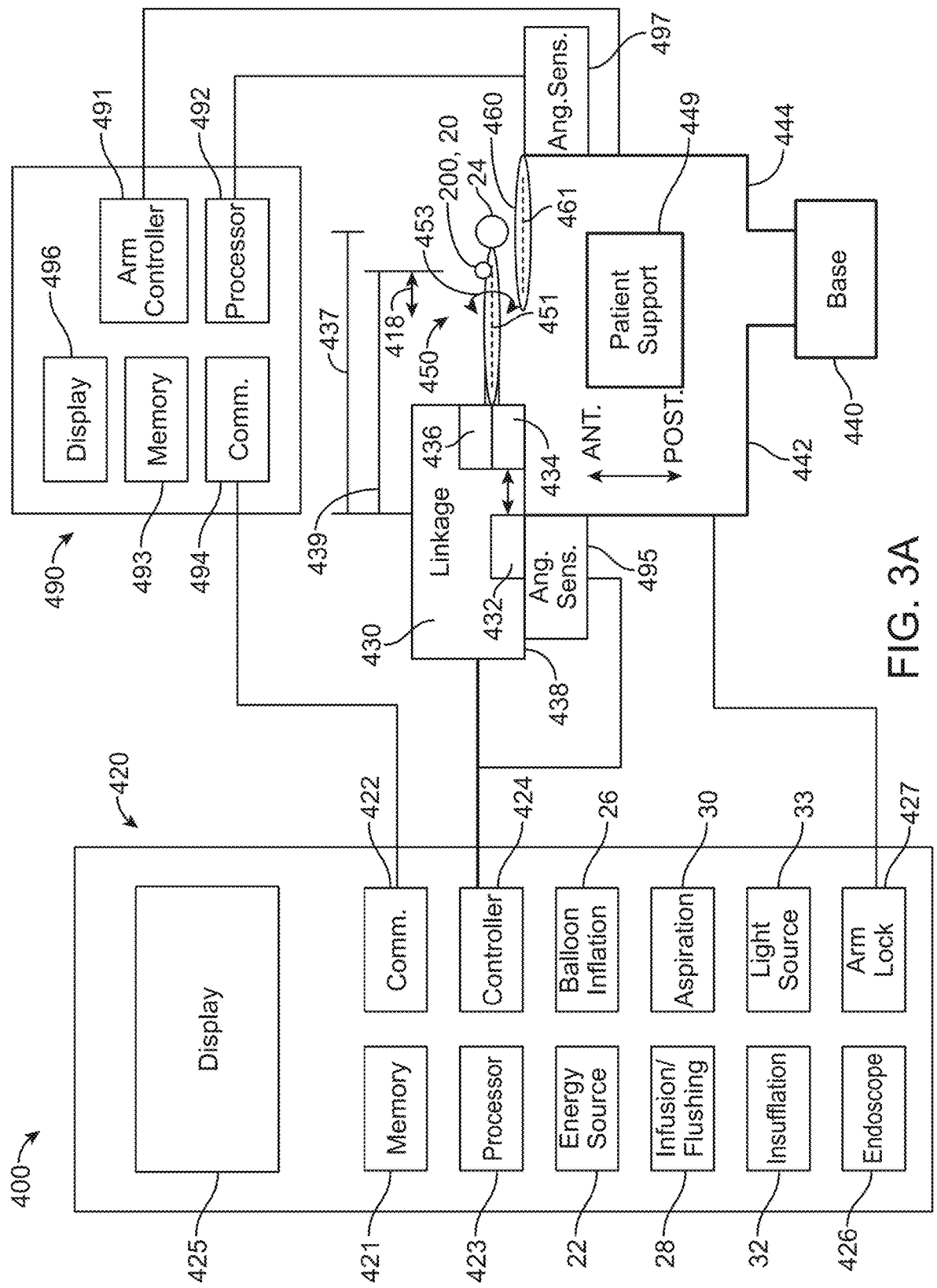
FIGS. 3A and 3B show a system to treat a patient in accordance with some embodiments.
Figure 3B:
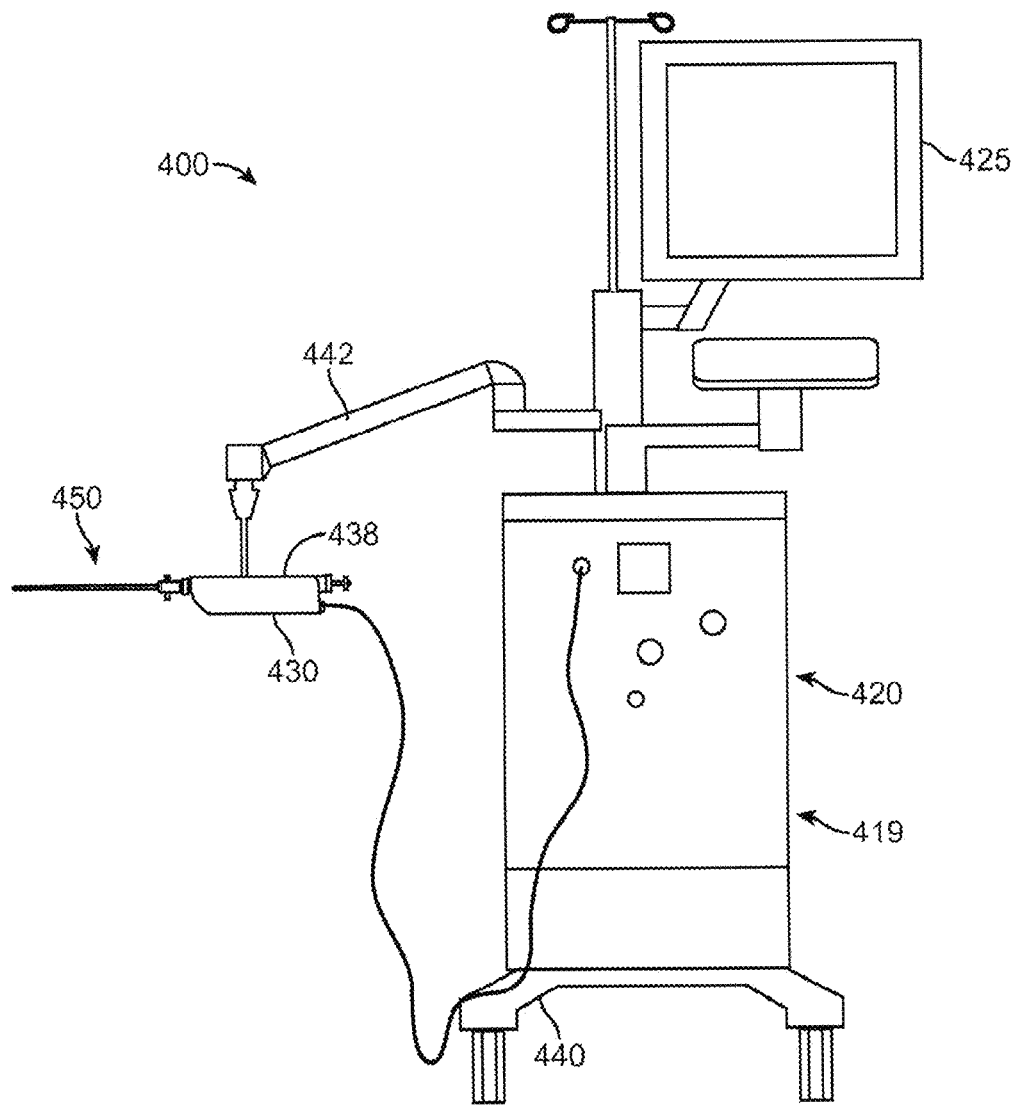

FIGS. 3A and 3B show a system to treat a patient in accordance with embodiments. The system 400 comprises a treatment probe 450 and may optionally comprise an imaging probe 460, and a light source 33. The treatment probe 450 is coupled to a console 420 and a linkage 430. The imaging probe 460 is coupled to an imaging console 490. The patient treatment probe 450 and the imaging probe 460 can be coupled to a common base 440. The patient is supported with the patient support 449. The treatment probe 450 is coupled to the base 440 with an arm 442. The imaging probe 460 is coupled to the base 440 with an arm 444.

The patient is placed on the patient support 449, such that the treatment probe 450 and ultrasound probe 460 can be inserted into the patient. The patient can be placed in one or more of many positions such as prone, supine, upright, or inclined, for example. In many embodiments, the patient is placed in a lithotomy position, and stirrups may be used, for example. In many embodiments, the treatment probe 450 is inserted into the patient in a first direction on a first side of the patient, and the imaging probe is inserted into to the patient in a second direction on a second side of the patient. For example, the treatment probe can be inserted from an anterior side of the patient into a urethra of the patient, and the imaging probe can be inserted trans-rectally from a posterior side of the patient into the intestine of the patient. The treatment probe and imaging probe can be placed in the patient with one or more of urethral tissue, urethral wall tissue, prostate tissue, intestinal tissue, or intestinal wall tissue extending therebetween.

The treatment probe 450 and the imaging probe 460 can be inserted into the patient in one or more of many ways. During insertion, each arm may comprise a substantially unlocked configuration such the probe can be desirably rotated and translated in order to insert the probe into to the patient. When a probe has been inserted to a desired location, the arm can be locked. In the locked configuration, the probes can be oriented in relation to each other in one or more of many ways, such as parallel, skew, horizontal, oblique, or non-parallel, for example. It can be helpful to determine the orientation of the probes with angle sensors as described herein, in order to map the image date of the imaging probe to treatment probe coordinate references. Having the tissue image data mapped to treatment probe coordinate reference space can allow accurate targeting and treatment of tissue identified for treatment by an operator such as the physician.

In many embodiments, the treatment probe 450 is coupled to the imaging probe 460. In order to align the treatment with probe 450 based on images from imaging probe 460. The coupling can be achieved with the common base 440 as shown. Alternatively or in combination, the treatment probe and/or the imaging probe may comprise magnets to hold the probes in alignment through tissue of the patient. In many embodiments, the arm 442 is a movable and lockable arm such that the treatment probe 450 can be positioned in a desired location in a patient. When the probe 450 has been positioned in the desired location of the patient, the arm 442 can be locked with an arm lock 427. The imaging probe can be coupled to base 440 with arm 444, can be used to adjust the alignment of the probe when the treatment probe is locked in position. The arm 444 may comprise a lockable and movable probe under control of the imaging system or of the console and of the user interface, for example. The movable arm 444 may be micro-actuable so that the imaging probe 440 can be adjusted with small movements, for example a millimeter or so in relation to the treatment probe 450.

In many embodiments the treatment probe 450 and the imaging probe 460 are coupled to angle sensors so that the treatment can be controlled based on the alignment of the imaging probe 460 and the treatment probe 450. An angle sensor 495 is coupled to the treatment probe 450 with a support 438. An angle sensor 497 is coupled to the imaging probe 460. The angle sensors may comprise one or more of many types of angle sensors. For example, the angle sensors may comprise goniometers, accelerometers and combinations thereof. In many embodiments, angle sensor 495 comprises a 3-dimensional accelerometer to determine an orientation of the treatment probe 450 in three dimensions. In many embodiments, the angle sensor 497 comprises a 3-dimensional accelerometer to determine an orientation of the imaging probe 460 in three dimensions. Alternatively or in combination, the angle sensor 495 may comprise a goniometer to determine an angle of treatment probe 450 along an elongate axis of the treatment probe. Angle sensor 497 may comprise a goniometer to determine an angle of the imaging probe 460 along an elongate axis of the imaging probe 460. The angle sensor 495 is coupled to a controller 424. The angle sensor 497 of the imaging probe is coupled to a processor 492 of the imaging system 490. Alternatively, the angle sensor 497 can be coupled to the controller 424 and also in combination.

The console 420 comprises a display 425 coupled to a processor system in components that are used to control treatment probe 450. The console 420 comprises a processor 423 having a memory 421. Communication circuitry 422 is coupled to processor 423 and controller 422. Communication circuitry 422 is coupled to the imaging system 490. The console 420 comprises components of an endoscope 35 that is coupled to anchor 24. Infusion flashing control 28 is coupled to probe 450 to control infusion and flushing. Aspiration control 30 is coupled to probe 450 to control aspiration. Endoscope 426 can be components of console 420 and an endoscope insertable with probe 450 to treat the patient. Arm lock 427 of console 420 is coupled to arm 422 to lock the arm 422 or to allow the arm 422 to be freely movable to insert probe 450 into the patient.

The console 420 may comprise a pump 419 coupled to the carrier and nozzle as described herein.

The processor, controller and control electronics and circuitry can include one or more of many suitable components, such as one or more processor, one or more field-programmable gate array (FPGA), and one or more memory storage devices. In many embodiments, the control electronics controls the control panel of the graphic user interface (hereinafter "GUI") to provide for pre-procedure planning according to user specified treatment parameters as well as to provide user control over the surgery procedure.

The treatment probe 450 comprises an anchor 24. The anchor 24 anchors the distal end of the probe 450 while energy is delivered to energy delivery region 20 with the probe 450. The probe 450 may comprise a nozzle 200 as described herein. The probe 450 is coupled to the arm 422 with a linkage 430.

The linkage 430 comprises components to move energy delivery region 20 to a desired target location of the patient, for example, based on images of the patient. The linkage 430 comprises a first portion 432 and a second portion 434 and a third portion 436. The first portion 432 comprises a substantially fixed anchoring portion. The substantially fixed anchoring portion 432 is fixed to support 438. Support 438 may comprise a reference frame of linkage 430. Support 438 may comprise a rigid chassis or frame or housing to rigidly and stiffly couple arm 442 to treatment probe 450. The first portion 432 remains substantially fixed, while the second portion 434 and third portion 436 move to direct energy from the probe 450 to the patient. The first portion 432 is fixed to the substantially constant distance 437 to the anchor 24. The substantially fixed distance 437 between the anchor 24 and the fixed first portion 432 of the linkage allows the treatment to be accurately placed. The first portion 424 may comprise the linear actuator to accurately position the high pressure nozzle in treatment region 20 at a desired axial position along an elongate axis of probe 450.

The elongate axis of probe 450 generally extends between a proximal portion of probe 450 near linkage 430 to a distal end having anchor 24 attached thereto. The third portion 436 controls a rotation angle 453 around the elongate axis. During treatment of the patient, a distance 439 between the treatment region 20 and the fixed portion of the linkage varies with reference to anchor 24. The distance 439 adjusts in response to computer control to set a target location along the elongate axis of the treatment probe referenced to anchor 24. The first portion of the linkage remains fixed, while the second portion 434 adjusts the position 418 of the treatment region along the axis 453. The third portion of the linkage 436 adjusts the angle around the axis in response to controller 424 such that the distance along the axis at an angle of the treatment can be controlled very accurately with reference to anchor 24. The probe 450 may comprise a stiff member such as a spine extending between support 438 and anchor 24 such that the distance from linkage 430 to anchor 24 remains substantially constant during the treatment. The treatment probe 450 is coupled to treatment components as described herein to allow treatment with one or more forms of energy such as mechanical energy from a jet, electrical energy from electrodes or optical energy from a light source such as a laser source. The light source may comprise infrared, visible light or ultraviolet light. The energy delivery region 20 can be moved under control of linkage 430 such as to deliver an intended form of energy to a target tissue of the patient.

The imaging system 490 comprises a memory 493, communication circuitry 494, display 496 and processor 492. The processor 492 in corresponding circuitry is coupled to the imaging probe 460. An arm controller 491 is coupled to arm 444 to precisely position imaging probe 460.

Figure 4A:
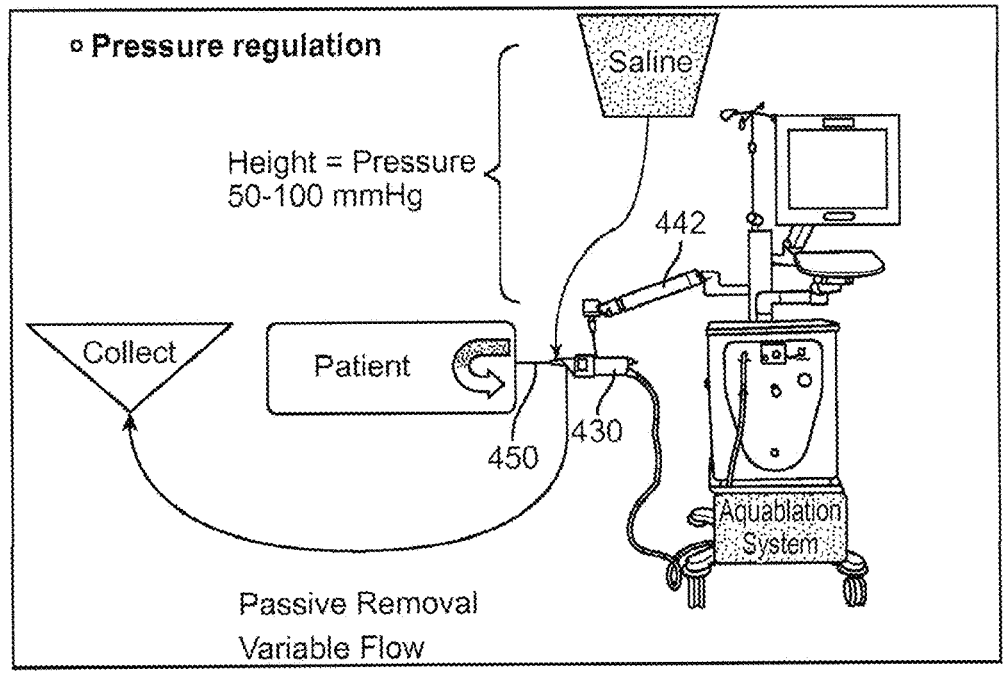
FIG. 4A shows pressure regulation of the surgical site with a substantially constant pressure and variable flow, in accordance with some embodiments.

FIG. 4A shows pressure regulation of the surgical site with a substantially constant pressure and variable flow. The saline bag is placed at a height to provide substantially constant pressure regulation. The bag of saline can be placed at a height corresponding to about 50 to 100 mm of Mercury (hereinafter "mmHg"). The saline bag is coupled to the irrigation port as described herein. A collection bag is coupled to one or more of the irrigation port, the aspiration port, or the suction port as described herein. The collection bag collects tissue removed with the water jet ablation probe 450 as described herein.

Figure 4B:
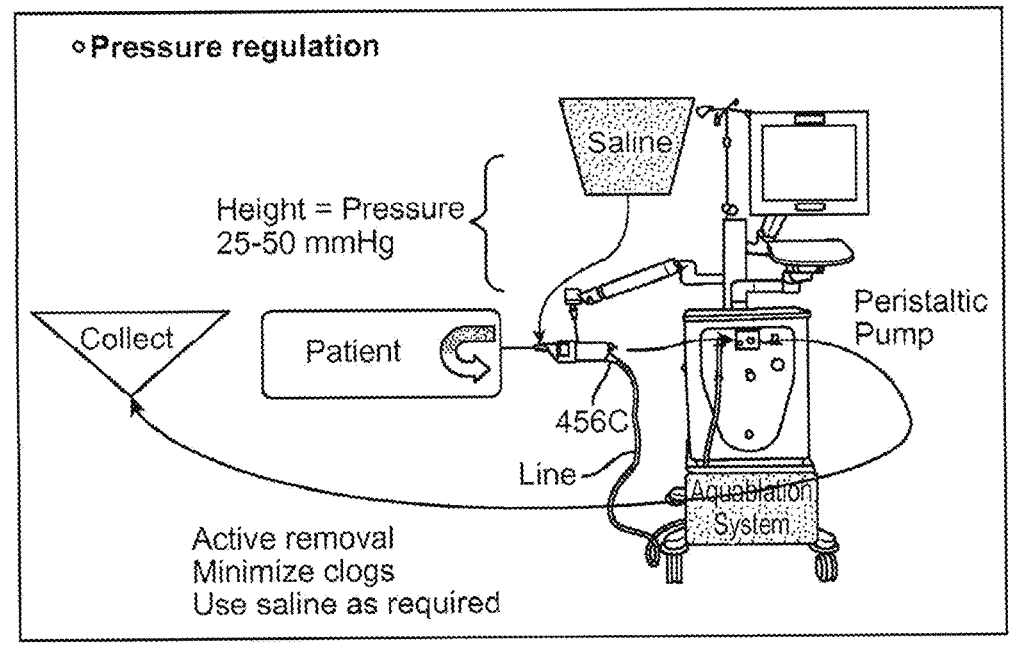
FIG. 4B shows flow regulation of the surgical site with a pump providing a substantially fixed fluidic flow and a substantially constant pressure, in accordance with some embodiments.

FIG. 4B shows flow fluidic regulation of the surgical site with a pump providing a substantially fixed fluidic flow. A pump removes fluid from the surgical site at a substantially fixed flow rate. The pump may comprise a peristaltic pump, for example. The pump is configured to remove fluid at the substantially the same rate or greater than the water ablation jet saline flow rate, in order to inhibit pressure build up at the surgical site. The peristaltic pump can be coupled to the aspiration port of the manifold comprising tissue removal port 456C as described herein, for example. Providing the pump having the flow rate that is at least the flow rate of the tissue ablation jet provides improve suction as ablated tissue that might otherwise block the tissue removal openings and channel can be subjected to greater amounts of pressure when the pump maintains the substantially fixed flow rate in order to remove the material that would otherwise block the channel.

The irrigation flow from the saline bag may remain open in order to provide at least two functions: 1) maintain pressure based on the height of the saline bag; and 2) provide a safety check valve in case the peristaltic pump is not functioning correctly as visually a person would see flow entering the bag as a pink color.

In alternate embodiments, the flow of the pump comprises a variable rate in order to provide a substantially constant pressure within the patient near the surgical site. The active sensing of pressure of the treated organ and variable flow rate of the pump may comprise a closed loop pressure regulation system. The pump can be coupled to a sensor such as a pressure sensor, and the flow rate varied to maintain substantially constant pressure. The pressure sensor can be located in one or more of many places such as on the treatment probe, within the aspiration channel of the probe, in a recess of an outer surface the probe, on an inner surface of the probe coupled to the surgical site, or near the inlet to the pump on the console for example.

Figure 5A:
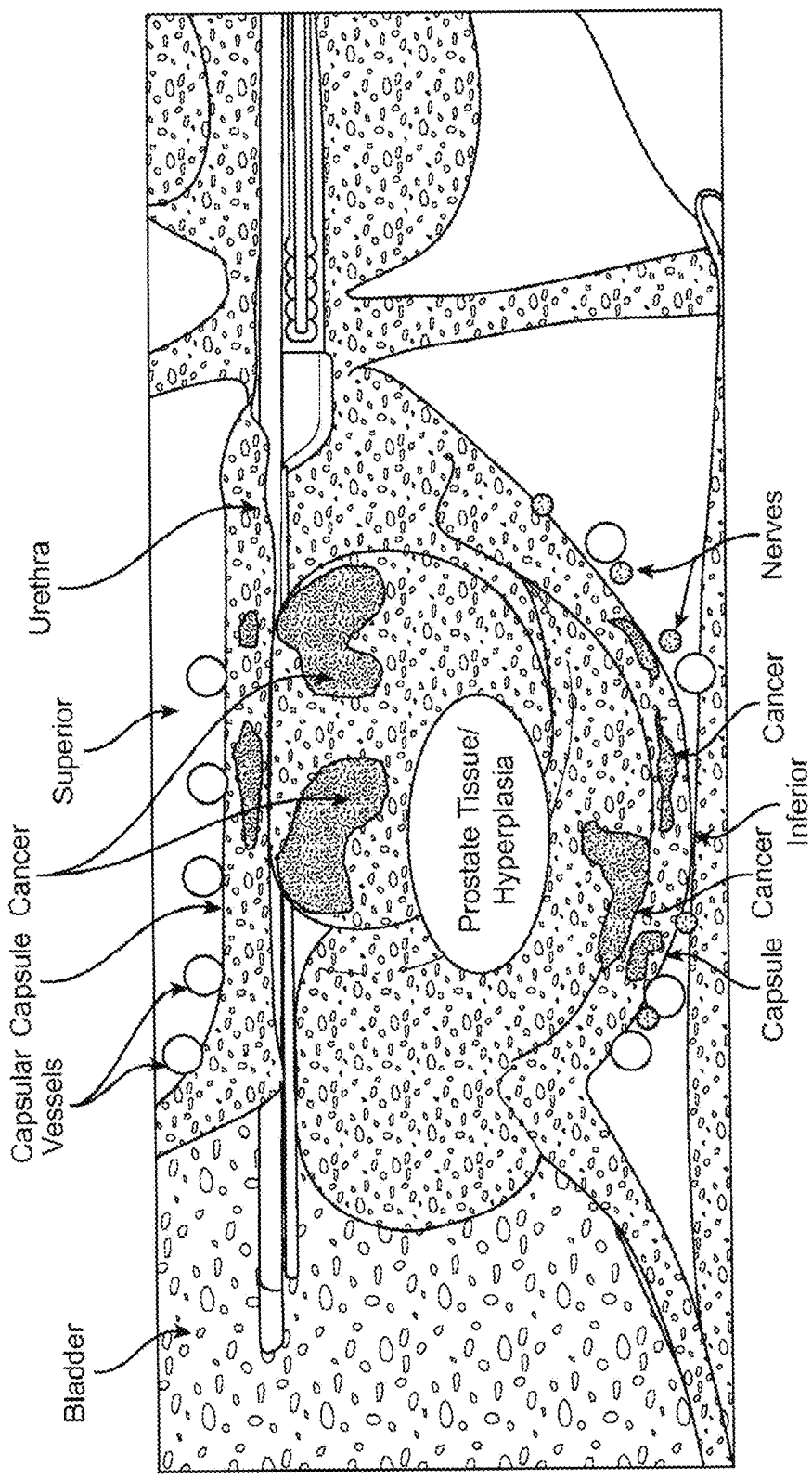
FIG. 5A shows an organ suitable for incorporation in accordance with many embodiments.

FIG. 5A shows an organ suitable for incorporation in accordance with embodiments. The organ may comprise one or more of many organs as described herein, for example, the prostate. In many embodiments the organ comprises a capsule and tissue contained within the capsule and capsular vessels and nerves located on an exterior of the capsule, for example. In many embodiments the organ comprises a prostate. The prostate may comprise hyperplasia such as benign prostate hyperplasia or cancer and combinations thereof, for example. In many embodiments the hyperplasic tissue may comprise tissue located within the patient in which the cancer may not have been detected. In many embodiments capsular vessels and nerves extend along an exterior surface of the prostate. In many embodiments the hyperplasic tissue can be located superiorly on the prostate. In the many embodiments the hyperplasic tissue may comprise tissue of unknown specificity with respect to whether the tissue comprises cancerous tissue or benign tissue.

Figure 5B:
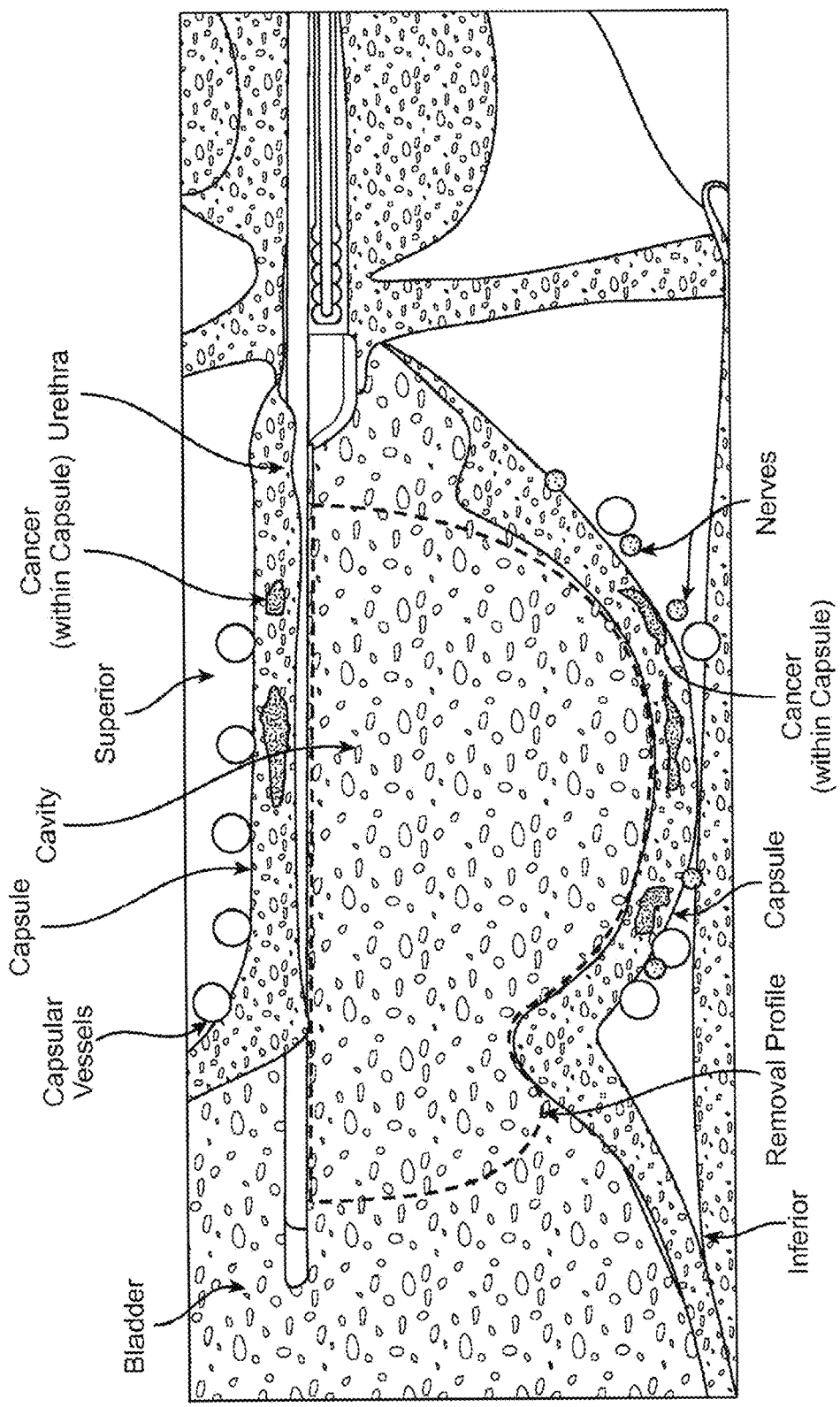
FIG. 5B shows the prostate of FIG. 5A treated with an apparatus in accordance with many embodiments.

FIG. 5B shows the prostate of FIG. 5A treated with an apparatus in accordance with embodiments. In many embodiments the tissue of the prostate is removed in accordance with a tissue removal profile. The tissue removal profile may comprise of predetermined tissue removal profile based on image-guided tissue removal as described herein, for example. Alternatively the tissue removal profile may comprise of removal profile of tissue removed with a handheld tissue removal apparatus. In many embodiments the tissue of the organ, such as the prostate, is removed to within the capsule in order to decrease the distance from the tissue removable profile to the exterior of the capsule, for example.

An apparatus for tissue removal may comprise a nozzle configured to deliver a fluid stream, wherein the fluid stream may comprise one or more of a liquid or a gas. A liquid fluid stream may comprise one or more of water or saline, for example. A liquid fluid stream may be configured to exit the nozzle in the form a liquid ablation jet, causing cavitations in the prostate tissue and dissociating the tissue into a plurality of fragments. The liquid fluid stream can be released into a liquid in which the nozzle is immersed in order to provide cavitation with shedding pulses as described herein. The liquid in which the nozzle is immersed may comprise one or more of water or saline, for example.

Figure 6A:
FIG. 6A shows an ablative flame visible to the human eye, in accordance with some embodiments.

FIG. 6A shows an ablative flame visible to the human eye, in accordance with embodiments.

Figure 6B:
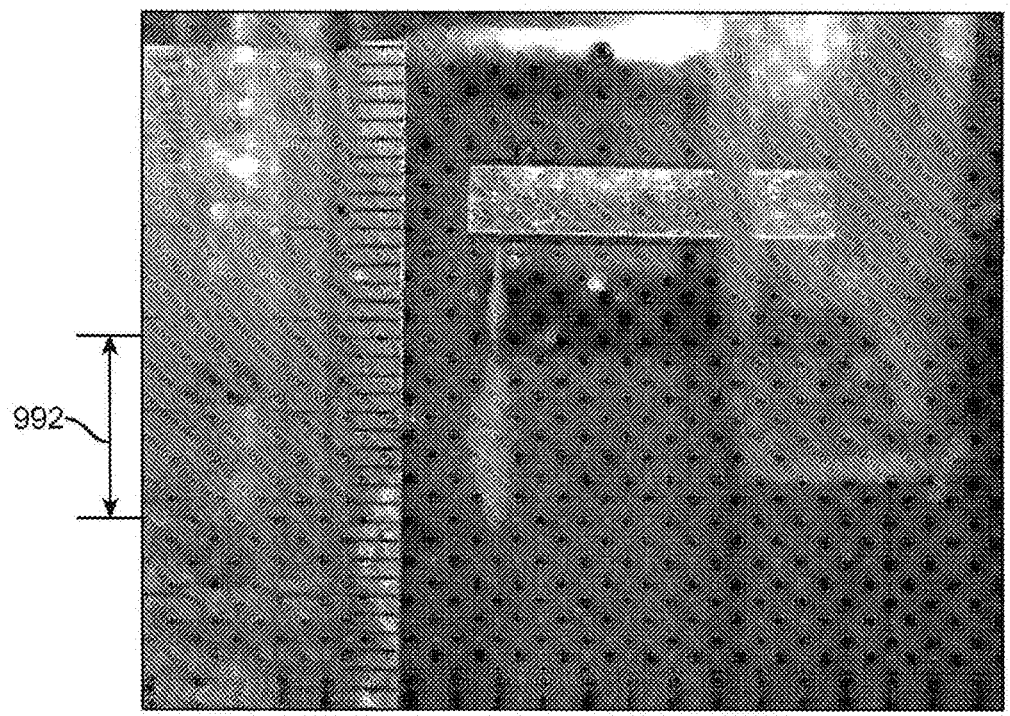
FIG. 6B shows a high speed image of the ablative flame as in FIG. 6A.

FIG. 6B shows a high speed image of the ablative flame as in FIG. 6A. The image was taken at a speed of about ¹⁄₄₀₀ of a second.

The data of FIGS. 6A and 6B show that the ablative flame comprises a plurality of white clouds generated with the ablative stream when released from the nozzle. Work in relation to embodiments has shown that the cavitating cloud can shed from the jet at a characteristic shedding frequency. A length 992 of each cloud is related to the shedding frequency and the velocity of the cloud. The relatively cool ablative flame of the jet comprises a length 990 corresponding to the cutting length of the jet which can be adjusted to cut tissue to controlled depth as described herein. In many embodiments, nozzle of the jet is placed at least about a quarter of the length 992 of a shed cloud in a non-cutting configuration as shown in FIG. 6B, in order to allow the shedding cloud to substantially form prior to the cloud striking tissue. This divergence of the shed cloud to a larger cross sectional size can also provide improved tissue removal as the cloud can be distributed to a larger region of tissue and provide improved overlap among the pulses of the jet.

In addition to the impact pressure of the jet, the highly turbulent and aggressive region corresponding to the white cloud of the image contributes substantially to the ablation of tissue as described herein. The white cloud comprises a plurality of cavitation regions. When pressurized water is injected into water, small cavitations are generated in areas of low pressure in the shear layer, near the nozzle exit. The small cavitations may comprise cavitation vortices. The cavitation vortices merge with one another, forming large discrete cavitation structures that appear in the high speed images as cavitation clouds. These cavitation clouds provide effective ablation when interacting with tissue. Without being bound by any particular theory, it is believed that the cavitation clouds striking tissue cause substantial erosion of tissue related to the cavitations in combination of the high velocity fluid that defines the cavitations striking tissue.

The nozzle and pressure as described herein can be configured to provide the pulsatile clouds, for example with control of the angle of the nozzle, by a person of ordinary skill on the art based on the teachings provided herein. In many embodiments, the nozzle of the fluid delivery element comprises a cavitating jet in order to improve ablation of tissue.

The fluid delivery element nozzle and pressure can be arranged to provide a shedding frequency suitable for removal of tissue.

In many embodiments, the "white cloud" of "flame" comprises an "entrainment" region where surrounding water is drawn in or "entrained" into the jet. Work in relation to embodiments suggests that the entrainment of fluid can be related to the shedding frequency.

Figure 7:
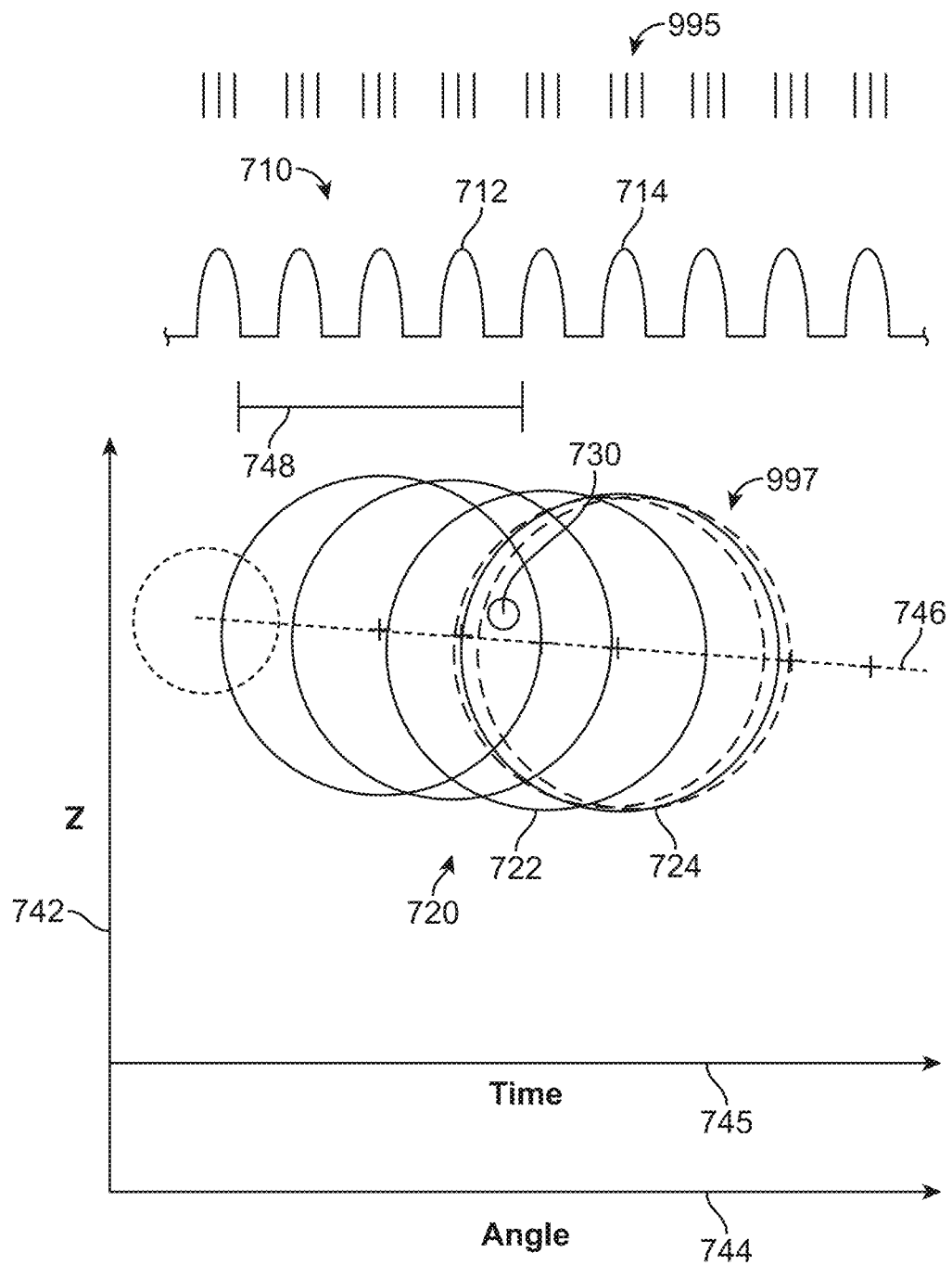
FIG. 7 shows a plurality of shedding pulses and sweeping of the ablative jet to provide smooth and controlled tissue erosion at a plurality of overlapping locations in accordance with some embodiments.

The shedding frequency and size 748 of the cloud shed from the jet can be used to provide tissue ablation in accordance with embodiments, as shown in FIG. 7. The shedding frequency can be combined with the angular sweep rate of the probe around the longitudinal axis to provide overlap of the locations where each cloud interacts with the tissue.

FIG. 7 shows a plurality of shedding pulses 995 and sweeping 720 of the ablative jet to provide smooth and controlled tissue erosion at a plurality of overlapping locations 997 at time 745, angle 744, and z position 742 of the jet, in accordance with embodiments. This shedding frequency can be substantially faster than the pump frequency 710, when a pump is used, such that a plurality of shedding clouds 995 is provided for each pulse 714 of the pulsatile pump. The sweep rate of the probe along path 746 can be related to shedding frequency to provide improved tissue removal, for example with the shedding clouds configured to provide overlapping pulses 722, 724 at location 730.

In many embodiments, the system comprises a pump having a frequency less than a frequency of the shedding pulses, in order to provide a plurality of shedding pulses for each pulse of the pump. The pump can have a pulse rate of at least about 50 Hz, for example within a range of about 50 Hz to about 200 Hz, and the shedding pulses comprise a frequency of at least about 500 Hz, for example within a range from about 1 kHz to about 10 KHz.

Although pulses 712, 714 of a pump are illustrated, similar scanning of pulsed clouds can be provided with a continuous flow pump.

While the nozzle can be configured in one or more of many ways, in many embodiments the nozzle comprises a Strouhal number (hereinafter "St") within a range from about 0.02 to about 0.3, for example within a range from about 0.10 to about 0.25, and in many embodiments within a range from about 0.14 to about 0.2.

In many embodiments, the Strouhal number is defined by:

$$St = (Fshed)*(W)/U$$

where Fshed is the shedding frequency, W is the width of the cavitating jet, and U is the velocity of the jet at the exit. A person of ordinary skill in the art can modify nozzles as described herein in order to obtain shedding frequencies suitable for combination in accordance with embodiments described herein, and experiments can be conducted to determine the cloud lengths and shedding frequencies suitable for tissue removal.

The nozzle configurations providing plurality of shedding clouds are suitable for use with one or more of the probes as described herein.

Figure 8A:
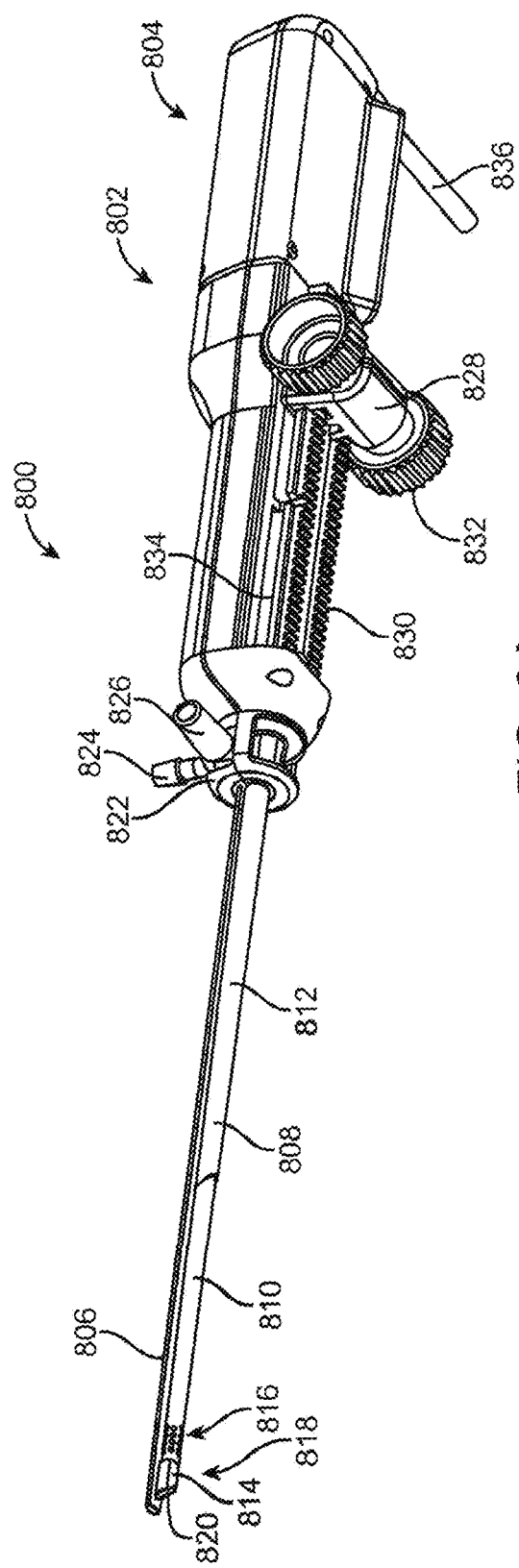
FIG. 8A shows an attachment device in accordance with some embodiments.

FIG. 8A shows an attachment device 800 in accordance with embodiments. The attachment device is configured to attach to an arm as described herein. The attachment device comprises one or more components of the surgical system to treat the patient as described herein. In many embodiments the attachment device comprises a handpiece 802 for the surgeon to manipulate the attachment device with the arm in the unlocked position in order to insert the distal end of the attachment device into the patient. In many embodiments the attachment device comprises a linkage 804 comprising rotatable bodies configured to receive torque in rotation from the arm as described herein.

The attachment device comprises a plurality of components sized to fit within a surgical access site of the patient such as a urethra, for example. The attachment device may comprise the elongate support 806, the elongate tube 808 and the coupling 814 as described herein, for example. The elongate support 806 comprises a stiff support configured for insertion into the patient. The elongate support may comprise a rounded distal end in order to facilitate insertion into the patient along an access path in order to expand the path to allow and facilitate insertion of the coupling. The elongate support may comprise a plurality of aspiration channels located to remove tissue excised from the surgical site. The elongate support may comprise a plurality of channels extending from an aspiration port 828 to the openings on the distal end of the elongate support.

The elongate tube 808 may comprise a telescopic tube comprising a first distal portion 810 and a second proximal portion 812. The second portion can be sized larger than the first portion in order to receive the first portion and allow sliding of the tube. The coupling 814 on the distal end of the distal portion of the tube can be connected to an endoscope. The endoscope connected to the coupling can be moved proximally and distally and the elongate tube can shorten and decrease in length as the coupling moves proximally and distally with the distal tip 818 of the endoscope.

The coupling 814 may comprise inclined distal surfaces 820 or at least one surface that is shaped to facilitate the insertion of the coupling into the patient. The coupling can be placed adjacent to the distal end of the elongate support when the attachment device is inserted into the patient. The endoscope tip 818 can be coupled to the coupling with structures of the coupling. For example, the coupling may comprise an engagement structure shaped to receive a corresponding engagement structure on the endoscope tip such that the coupling mates with the endoscope tip and is effectively keyed and locked to the endoscope tip. Proximal and distal movement of the endoscope can move the coupling proximally and distally with a corresponding decrease or increase in the length of the elongate tube.

The attachment device may comprise a hub 822 comprising the irrigation port 824 and the aspiration port 826. The irrigation port can be coupled to the internal channel of the elongate tube in order to direct fluid such as saline to irrigation openings 816 located on the distal end of the elongate tube. The irrigation openings can provide fluid to the surgical site such as saline. Alternatively, a fluid such as a gas can be provided to the surgical site with insufflation. The aspiration port on the hub can be connected to openings on the elongate support with channels extending axially along the elongate support.

The elongate tube 808 of the endoscope comprises a first distal portion 810 of the tube and a second proximal portion 812 of the elongate telescopic tube. The second proximal portion is sized larger than the first distal portion in order to slidingly receive the first distal portion to allow the coupling to move proximally and distally with the endoscope.

The attachment device comprises a plurality of structures that allow a user such as a physician to adjust the endoscope independently of other components of the device. In many embodiments, the endoscope is coupled to an endoscope carriage 828. The endoscope carriage can be advanced and retracted in order to move the distal end of the endoscope connected to the coupling proximally and distally. The attachment device may comprise a rack 830 that is coupled to a pinion gear that allows the endoscope carriage to be moved proximally and distally with rotation of a knob 832 on the endoscope carriage. The attachment device may comprise a rail 834 to engage the endoscope carriage such that the endoscope carriage can slide along the rail with rotation of the knob, for example. In many embodiments the attachment device comprises a connection of a high pressure cable 836 with a carrier that carries a source of treatment energy under control of the linkage.

Figure 8B:
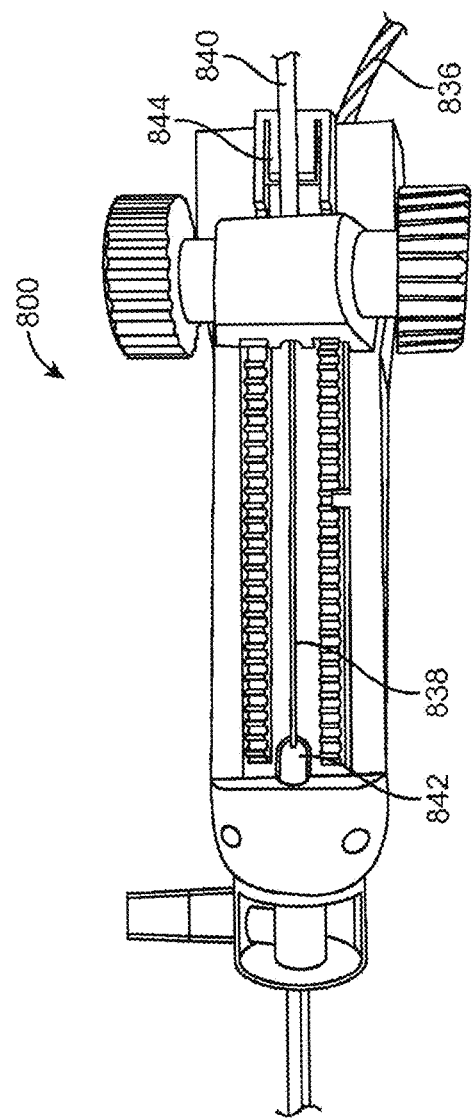
FIG. 8B shows components of the attachment device.

FIG. 8B shows components of the attachment device 800. The endoscope may comprise a stiff distal portion 838 and a flexible proximal portion 840. The stiff portion of the endoscope can extend from the endoscope carriage 828 to the distal tip of the endoscope. The stiff portion of the endoscope can extend through a seal 842 in order to seal and contain fluid from the surgical site. The stiff portion of the endoscope can be coupled to the carriage with an engagement structure on a proximal portion of the endoscope. The stiff portion of the endoscope can also be coupled to the coupling with a distal engagement structure located near the tip of the endoscope. The stiff portion of the endoscope extending between the carriage and the coupling provides proximal and distal motion of the coupling and the distal portion of the telescopic tube.

In many embodiments a flexible high pressure saline tube 836 extends to the attachment device to provide pressurized fluid from an external pump.

In many embodiments, the attachment device is configured for the user to remove components of the device such as the endoscope. For example, a carriage release 844 can be provided on the proximal end of the attachment device that allows the user to slide the carriage off of the rail proximally in order to remove the endoscope from the surgical site.

Figure 8C:
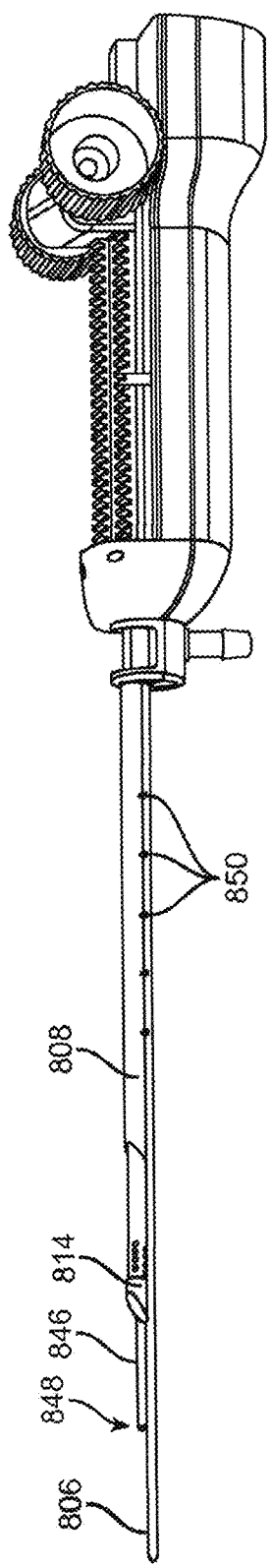
FIG. 8C shows components of the attachment device with the coupling in a partially retracted position and an elongate carrier comprising an energy source extending through the coupling toward the distal end of the elongate support.

FIG. 8C shows components of the attachment device 800 with the coupling 814 in a partially retracted position and an elongate carrier 846 comprising an energy source 848 extending through the coupling toward the distal end of the elongate support 806. In many embodiments, the endoscope tip can be at least partially retracted in order to view the treatment probe 846 in the support. The elongate carrier comprising the treatment probe can have an energy source located thereon to direct energy to a treatment site. The distal portion of the elongate tube 808 can be retracted within the proximal portion of the elongate tube in order to allow the coupling having the endoscope tip attached thereto to view the treatment site. The coupling can be retracted proximally with rotation of the knob to a proximal location, for example.

The elongate support 806 can be connected to the elongate tube 808 in one or more of many ways to add stiffness. For example, the elongate support can be welded to a proximal portion of the elongate tube at a plurality of locations 850 to add stiffness to the combination of the elongate support and the elongate tube.

The welded portion of the elongate tube can remain at a fixed position in relation to the elongate support when the distal portion of the elongate tube slides relative to the proximal fixed portion of the tube.

Figure 8D:
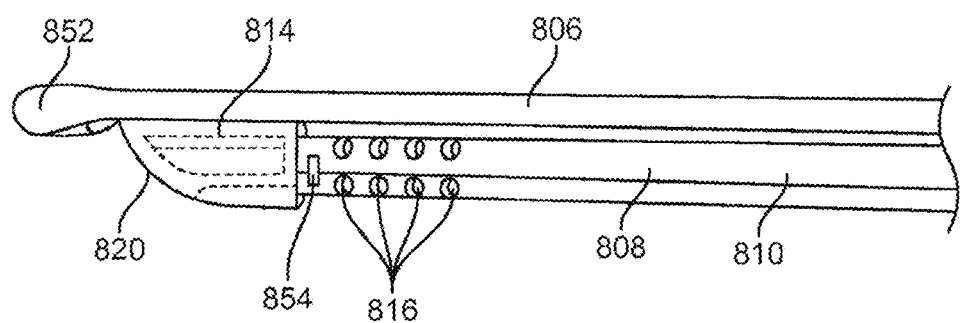
FIG. 8D shows distal portions of the elongate support and the elongate tube having the coupling mounted thereon.

FIG. 8D shows distal portions of the elongate support 806 and the elongate tube 808 having the coupling 814 mounted thereon. The elongate support may comprise a pressure reducing tip such as a rounded distal tip 852 in order to facilitate insertion along a surgical access path such as through the urethra. The inclined distal surface 820 of the coupling can facilitate insertion and urge tissue away from the elongate support. In many embodiments, the elongate support comprises a recess sized to receive a portion of the coupling such that the distal most tip of the coupling fits within the recess behind the pressure-reducing distal tip. The pressure-reducing distal tip can define an access path for the attachment device into the patient and the inclined distal surface of the coupling can follow the pressure-reducing tip and the tip of the coupling can follow a path of the pressure-reducing tip. This combination of the pressure-reducing tip and inclined distal surface can facilitate insertion.

The elongate tube 808 comprising a plurality of openings 816 can move with the coupling 814. The coupling to receive the distal tip of the endoscope can be configured in one or more of many ways to receive the endoscope tip, such as with a channel or slot that receives a protrusion on the endoscope and locks to the endoscope. The distal portion of the elongate telescopic tube may comprise an opening 854 to receive a fastener from the coupling. The fastener from the coupling extending through the opening of the tube can effectively lock the coupling to the distal end of the tube. The distal end 810 of the tube may comprise a plurality of irrigation openings 816. The plurality of irrigation openings can move with the endoscope tip in order to rinse and facilitate viewing with the endoscope tip. The movement of the irrigation openings generally directs fluid towards the surgical site such that the fluid can be directed. The irrigation openings that move with the endoscope tip have the advantage of rinsing the tip and providing fluid to increase visibility when the treatment probe tip is immersed in liquid, for example.

FIGS. 8E1 through 8E4 show the coupling 814 in accordance with embodiments. FIG. 8E1 shows a cross-sectional end view. FIG. 8E2 shows a cross-sectional side view. FIG. 8E3 shows a side view and FIG. 8E4 shows an end view. The coupling comprises a carrier channel 856 to receive the treatment probe on the carrier as described herein. The carrier channel is sized to allow the carrier comprising the treatment probe to slide proximally, distally and rotationally without interference from the coupling. The carrier channel may comprise a guide that facilitates alignment and placement and stabilizes the location of the distal end of the carrier comprising the energy source. The coupling comprises an endoscope channel 858 sized to receive the endoscope. The endoscope channel can be configured to receive the endoscope and an engagement structure of the endoscope and lock the engagement structure of the endoscope to the coupling.

With the side view shown in FIG. 8E2, the field of view 860 of the endoscope is shown. The field of view of the endoscope can be a field of view of a commercially available endoscope such as a 70° field of view, for example. The endoscope can view the surgical site, the elongate support and the treatment probe of the carrier from within the endoscope channel. In many embodiments, the inclined surface 820 of the distal end of the coupling is inclined with an angle so as to define the field of view along an upper portion of the field of view of the endoscope.

As shown in FIG. 8E3, the coupling 814 may comprise a slot 862 to receive a protrusion on the endoscope. The slot can be sized so as to allow the protrusion to enter the slot with rotation of the endoscope, for example. Although a slot is shown, the engagement structure of the coupling that receives the engagement structure on the distal end of the stiff portion of the endoscope can be configured in one or more of many ways such as with locking structures, threaded structures, hubs and threads, for example.

For example, the endoscope tip may comprise a leaf spring or a similar structure, configured to snap into a corresponding catching edge or lip disposed along at least a portion of an inner circumference of the coupling. Using such a mechanism, a user may lock the endoscope tip to the coupling by simply pushing the endoscope tip into the coupling until the leaf spring engages the catching edge. To allow uncoupling of the endoscope tip from the coupling, a portion of the inner circumference of the coupling may comprise a slanted edge configured to allow the leaf spring to slide out. To uncouple the endoscope tip from the coupling, the user may rotate the endoscope until the leaf spring is aligned with the slanted edge, and pull the endoscope out.

Also shown in FIG. 8E3 is a protrusion 855 that extends through the tube.

FIG. 8E4 shows approximate dimensions of the treatment probe carrier 846 and endoscope 866 with dashed lines in the carrier channel 856 and endoscope channel 858 respectively. The carrier channel and endoscope channel can be sized and spaced apart to provide a clearance gap 868 between the carrier and the endoscope. In many embodiments, the stiff distal tip of the endoscope comprises a protrusion 864 as described herein. The protrusion can extend a radial distance from the stiff distal portion to fit into the slot 862 and engage the coupling. In many embodiments, the protrusion is dimensioned to extend a distance greater than the gap in order to lock the coupling to the endoscope when the carrier probe comprising the energy source extends through the carrier channel. This configuration can facilitate assembly and disassembly of the coupling from the endoscope with the carrier removed, and provides locking of the coupling with the carrier inserted into the coupling, for example.

Figure 8F:
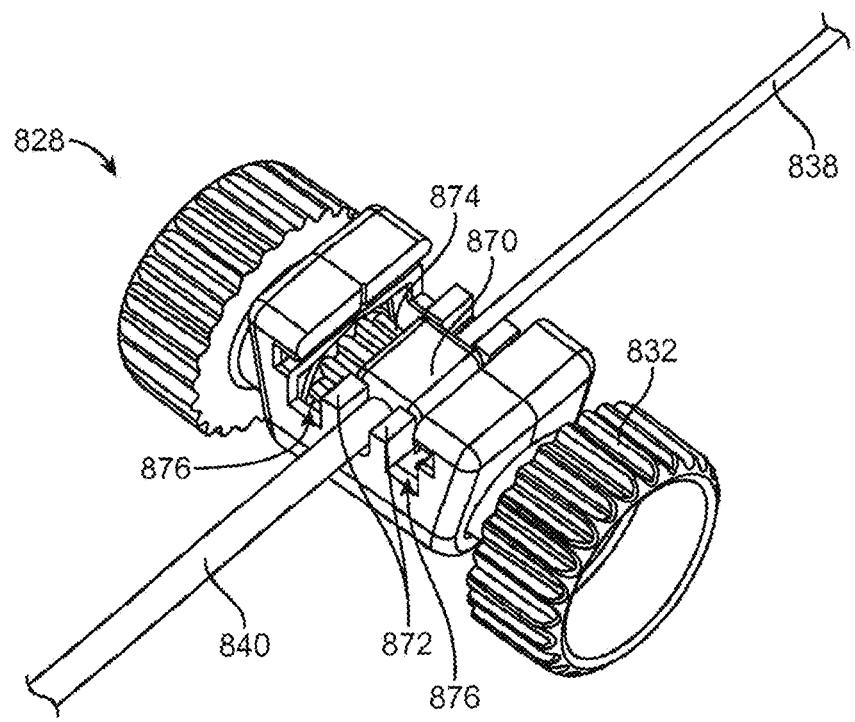
FIG. 8F shows an underside view of the carriage in accordance with some embodiments.

FIG. 8F shows an underside view of the carriage 828 in accordance with embodiments. The underside view shows the stiff portion 838 of the endoscope and the flexible portion 840 of the endoscope coupled to the proximal engagement structure 870 of the endoscope. The proximal engagement structure of the endoscope fits within an engagement structure 872 of the carriage such that movement of the carriage proximally and distally moves the stiff portion of the endoscope in the engagement structure. The underside view of the carriage shows a pinion gear 874 which rotates with the knob 832. The pinion gear engages the rack as described herein. Also shown in the underside view is a slot 876 on each side of the carriage that receives a rail of the attachment device as described herein. The engagement structure 872 of the carriage may comprise a plurality of protrusions. For example, the plurality of protrusions can extend on a proximal side of the carriage and a distal side of the carriage in order to move the endoscope proximally and distally.

Figure 8G:
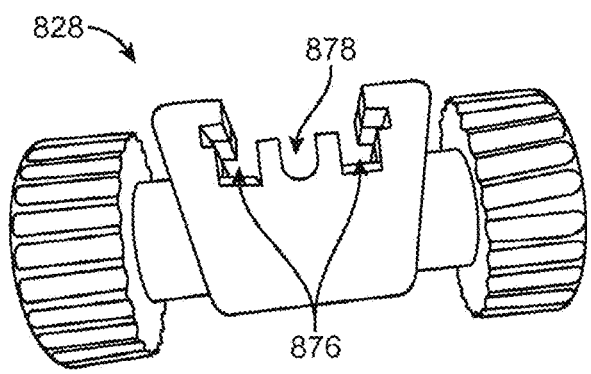
FIG. 8G shows an end view of the carriage in accordance with some embodiments.

FIG. 8G shows an end view of the carriage 828 in accordance with embodiments. The carriage comprises a plurality of slots 876 sized to receive the rail of the attachment device. The carriage also comprises a channel 878 sized to receive the endoscope.

The carriage shown in FIGS. 8F and 8G may be configured to have a low profile, in order to facilitate user handling of the attachment device. For example, the carriage can be configured to have a housing with a relatively shorter height, and the knobs can be shaped and dimensioned to have a relatively smaller diameter and longer length (e.g., to facilitate gripping of the knob by a user).

Figure 8H:
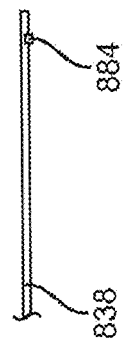
FIG. 8H shows an endoscope in isolation in accordance with some embodiments.
Figure 8H:
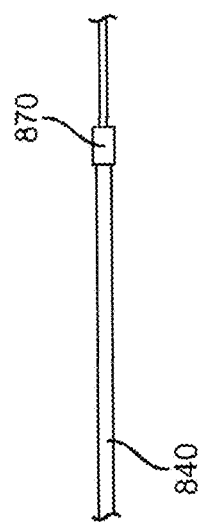
Figure 8H:
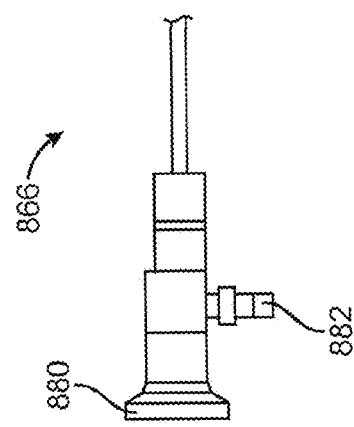

FIG. 8H shows an endoscope 866 in isolation in accordance with embodiments. The endoscope comprises an eyepiece 880 that allows a user such as a surgeon to view the surgical site from the distal end of the endoscope, wherein the eyepiece is located on the proximal end of the endoscope. The endoscope comprises an illumination port 882 that allows a camera such as a high definition camera to be coupled to the endoscope. The endoscope comprises the proximal flexible portion 840 as described herein. The endoscope comprises a proximal engagement structure 870. The proximal engagement structure is located between the flexible proximal portion 838 of the endoscope and the stiff distal portion 840 of the endoscope. The endoscope comprises a distal engagement structure 884 as described herein.

FIG. 8I1 shows a side view of the endoscope 866. FIG. 8I2 shows a side view along section AA as in FIG. 8I1. FIG. 8I3 shows section BB of the endoscope of FIG. 8I1, wherein section BB comprises structures similar to those shown in section AA. FIG. 8I4 shows a top view of the endoscope as in FIG. 8I1. FIG. 8I5 shows a distal end of the endoscope as in FIG. 8I. The endoscope comprises the eyepiece 880, the illumination port 882, the flexible portion 840, the proximal engagement structure 870, the stiff distal portion 838 and the distal end 818 of the endoscope as described herein. FIGS. 8I2 and 8I3 show cross-sectional views of the endoscope and structures that provide a fixed alignment of the endoscope with respect to the engagement structures. For example, the flat surfaces shown along section AA and section BB correspond to a maximum of dimension across the proximal engagement structure. Having the proximal engagement structure in a fixed alignment with the endoscope can facilitate alignment and ensure an accurate reference frame when the endoscope is used. FIG. 8I4 in the top view shows the distal engagement structure 884 along section G. Detail G in FIG. 8I5 shows the distal engagement structure 884 extending as a protrusion 864 from the distal end.

In many embodiments, the proximal engagement structure comprises a reference structure such as a maximum dimension across that defines an orientation of the endoscope with respect to the attachment device. The maximum dimension across the proximal engagement structure informs the user or other person assembling the device of the reference frame of the endoscope with respect to the attachment device as described herein. The attachment device may comprise a reference frame for the treatment and surgery as described herein. For example, angular rotation of the treatment probe about an access can be made with respect to the attachment device and components of the attachment device such as encoders as described herein.

Figure 8J:
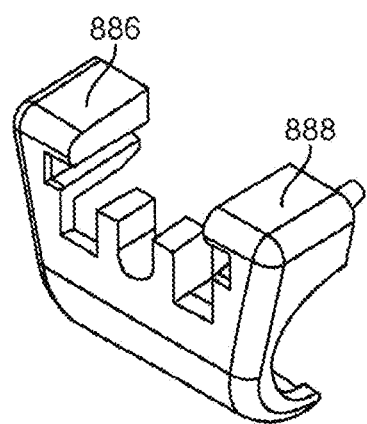
FIG. 8J shows a housing of the carriage as described herein.

FIG. 8J shows a housing 886 of the carriage as described herein. The housing of the carriage may comprise a single piece of injection-molded plastic, for example. A single piece can be provided in duplicate such as a pair of pieces of the single piece in order to allow assembly of the carriage housing. For example with reference to FIG. 8J, a second housing having the same shape as the first component 888 of the housing can be provided such that the two pieces snap together over the knob and axel and pinion gear as described herein so as to define the carriage.

Figure 8K:
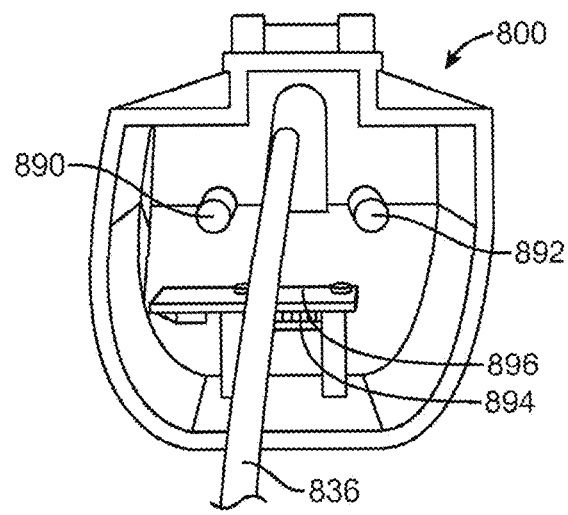
FIG. 8K shows an end view of the attachment device as described herein.

FIG. 8K shows an end view of the attachment device 800 as described herein. The attachment device comprises a plurality of rotatable connectors such as a first rotatable connector 890 and a second rotatable connector 892. A first rotatable connector determines an axial location of the energy source to treat the patient. A second rotatable connector determines an angular location of the energy source with respect to the axis. For example, the energy source may comprise a jewel mounted on a hypo tube in which an axial location of the jewel is determined with a first rotatable connector and an angle of the jewel with respect to the axis is determined with respect to a second rotatable connector. The first and second rotatable connectors can be used to control both the rotation and the axial location of the energy source as described herein. The attachment device comprising the handpiece may comprise an electrical connector 894. The electrical connector can connect to an electrical connector on the arm. The electrical connector can be used to transmit signals to and from the attachment device. The signals transmitted with the electrical connector can comprise electrical signals from the encoder to a controller away from the attachment device. The attachment device may comprise a printed circuit board 896 having the electrical connector disposed thereon in order to connect the attachment device to the arm. The electrical connector may comprise standard connectors known in the industry. The printed circuit board may comprise circuitry of the handpiece. The circuitry may comprise a processor for example in a nonvolatile memory configured to record aspects of the treatment such as the treatment table as described herein and machine parameters such as flow rate and pressure for example. The high pressure saline tube 836 may comprise a flexible tube extending into the proximal end of the handpiece.

Figure 8L:
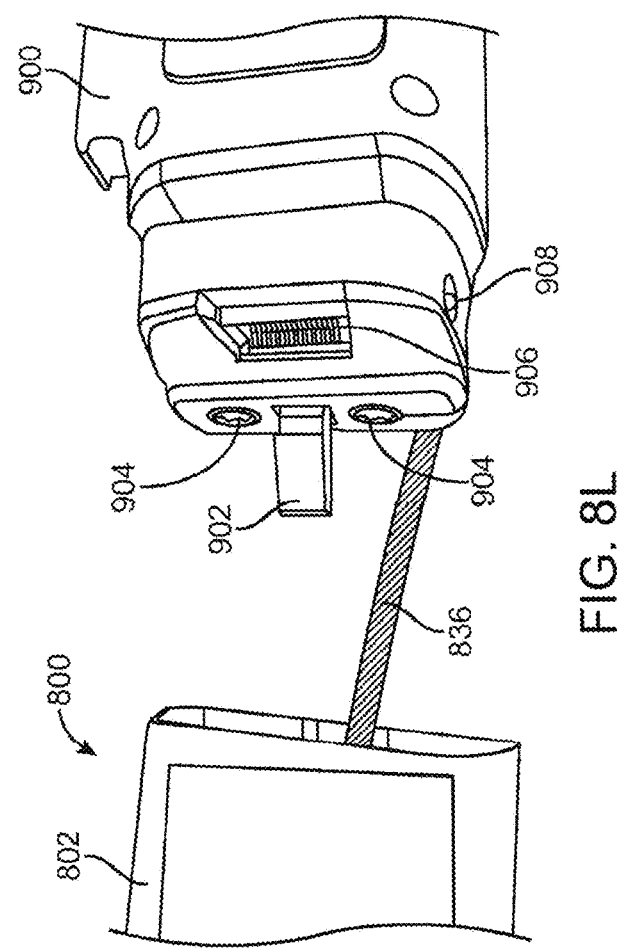
FIG. 8L shows components of the arm configured to couple to the attachment device.

FIG. 8L shows components of the arm 900 configured to couple to the attachment device 800. The arm may comprise a locking mechanical connector 902 configured to couple to the attachment device and lock the attachment device in place. The arm may comprise a plurality of rotatable connectors 904 configured to engage the rotatable connectors of the attachment device. The arm may comprise an electrical connector 906 configured to connect to the attachment device. Although an electrical connector is shown, other connectors can be used such as fiber optics or optical connectors, for example. The arm may also comprise a contact sensor 908 that senses contact of the attachment device with the arm.

The circuitry of the arm and the attachment device can be configured in one or more of many ways to facilitate connection of the attachment device to the arm. Alternatively or in combination, the attachment device can be configured to comprise a consumable device such as a single use device. In many embodiments, the contact sensor is coupled to circuitry configured to rotate the rotatable connectors on the arm in response to the contact sensor engaging the attachment device. When the contact sensor engages the attachment device, the rotatable connectors rotate back and forth through a predetermined range of motion in order to allow a mating connection of the rotatable connector on the arm with the rotatable connector on the attachment device. In many embodiments, the rotatable connector on the arm comprises a plurality of hexagonal sockets and the attachment device comprises a plurality of hexagonal cross-section protrusions to engage the sockets of the arm. Alternatively, the sockets and protrusions can be reversed such that the sockets are provided on the attachment device and the protrusions are provided on the arm or combinations thereof. Once the rotatable connector engages the rotatable connector of the attachment device, the circuitry within the arm can detect movement with sensors located on the attachment device and stop rotation of the rotatable connectors upon completion of the coupling of the arm to the attachment device.

Figure 8M:
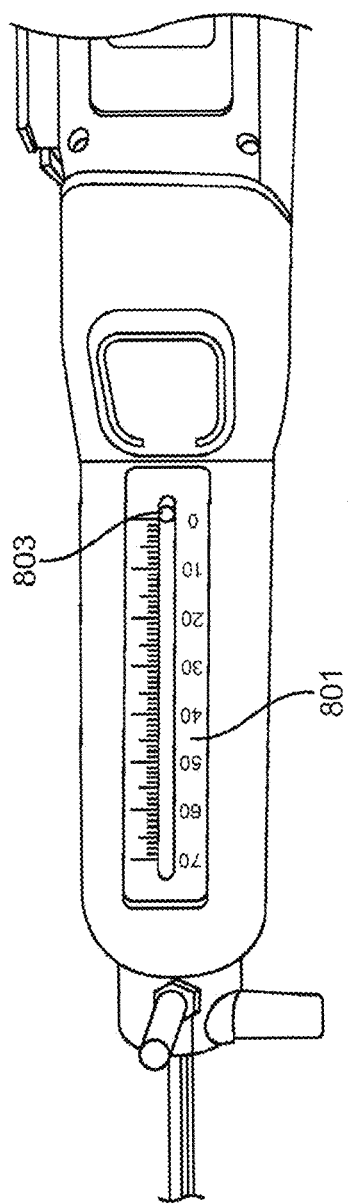
FIG. 8M shows a view of an upper side of the attachment device in accordance with some embodiments.

FIG. 8M shows a view of an upper side of the attachment device 800 in accordance with embodiments. The upper side of the attachment device can be located opposite the side having the rack and pinion, for example. The attachment device may comprise a measurement scale 801 and an indicator 803 such as an LED to indicate the location of the energy source on the carrier probe comprising the treatment probe. In many embodiments, the indicator is mounted on the internal linkage that moves axially in order to treat the patient. This LED indicator on the probe can inform the user the location of the treatment probe. The measurement scale may comprise one or more of many units and generally comprises a one-to-one scaling with motion of the probe tip. The measurement scale can be in units such as centimeters, millimeters or other units of length, for example.

Figure 8N:
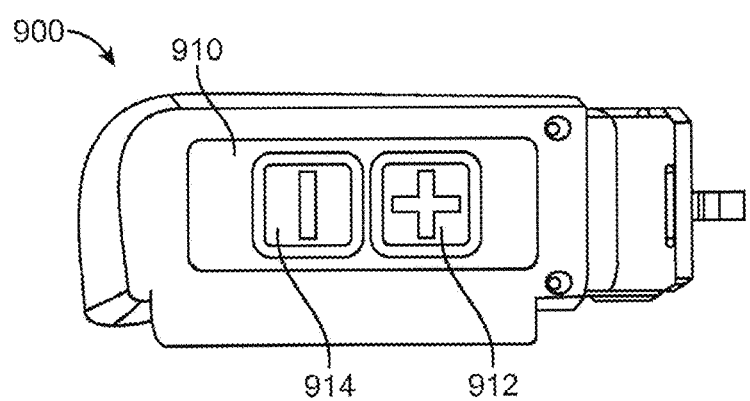
FIG. 8N shows a component of the arm in accordance with some embodiments.

FIG. 8N shows a component of the arm 900 in accordance with embodiments. The component of the arm may comprise an attachable component of the arm comprising a user input device 910. The user input device may comprise a first input 912 to increase an intensity of the energy source and a second input 914 to decrease an intensity of the energy source. For example, when the energy source comprises a liquid stream, the increase in the intensity of the energy source may comprise an increased flow rate of the energy source and/or an increased pressure of the energy source.

The decreased intensity of the energy source may comprise a decreased flow rate or a decreased pressure of the energy source and combinations thereof, for example.

FIG. 8O2 and FIG. 8O1 show internal structures of the arm components shown in FIG. 8N. FIG. 8O1 shows circuitry 916 of a lower portion of the component. The circuitry can be coupled to the connector 906 that couples to the attachment device. The circuitry may comprise circuitry as described herein and may comprise one or more of many known circuit components such as a processor, memory, such as random access memory, and a gate array, such as a field programmable gate array, for example. The circuitry may comprise one or more of many known components used to control motors. FIG. 8O2 shows motors 918 of the arm in accordance with embodiments. The motors may comprise known motor components capable of driving surgical instruments. The motors may comprise shafts extending to protrusions of the rotatable connector as described herein. The motors can engage the attachment device when the attachment device is connected to the arm.

The circuitry coupled to the connector as shown in FIG. 8O1 can be used to control the motors in order to position the energy source at an intended axial location and rotation angle about the axis. The circuitry may comprise one or more instructions to transmit signals to encoders located on the attachment device in order to measure an angular location of the probe rotated about the axis. The rotation of the energy source about the axis can be fed back to the circuitry and the circuitry can drive the energy source to a plurality of locations in accordance with instructions of a treatment table as described herein. By locating the circuitry and the motors at a reusable location on the arm, the cost and complexity of the attachment device comprising the handpiece can be decreased substantially.

Figure 8P:
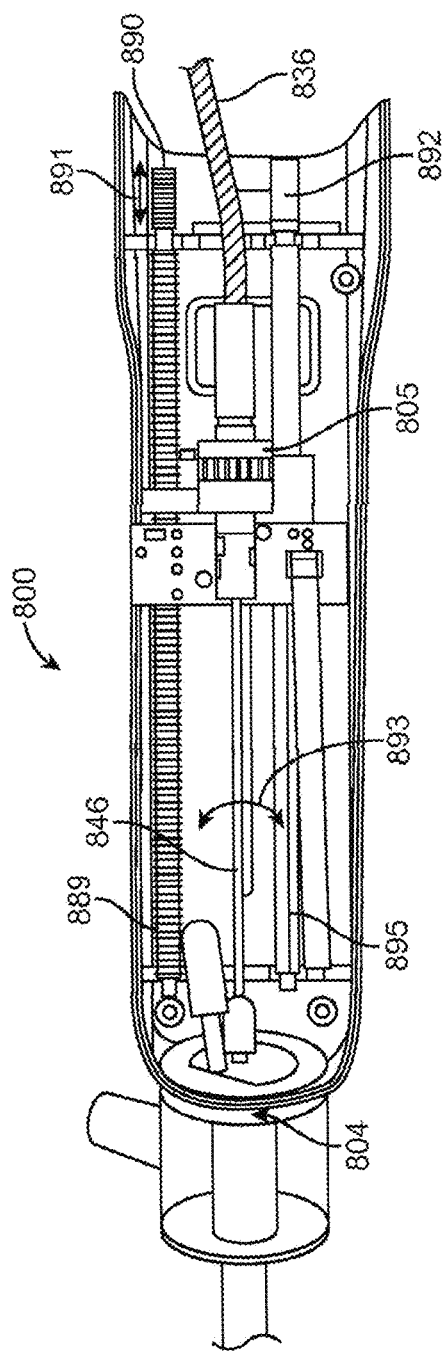
FIG. 8P shows the linkage of the attachment device in accordance with some embodiments.

FIG. 8P shows the linkage 804 of the attachment device 800 in accordance with embodiments. The linkage shown in FIG. 8P may comprise one or more components configured to direct the energy source to a desired location and angle on the distal end of the carrier 846 comprising the treatment probe. The carrier that carries the energy source near the distal end is coupled to the linkage so as to control the position and angle of the energy source on the end of the carrier. The carrier may comprise a hypo tube, for example, and the energy source may comprise one or more of many energy sources as described herein. For example, the energy source may comprise a nozzle formed in a material comprising a jewel. The jewel on the hypo tube can receive high pressure fluid from the cable 836. The carrier is connected to a flexible conduit that receives energy with a medium such as high-pressured saline along a flexible high pressure tube. The carrier connects to the linkage such that the carrier translates and rotates in response to commands from the circuitry.

The linkage comprises a first rotating connector 890 to control a Z axis position along the elongate axis of the carrier and a second rotatable connector 892 to control an angle of the energy source with respect to the elongate axis. The first rotatable connector 890 can be rotatably connected to a plurality of threads 889. Rotation of the threads can drive the linkage proximally and distally as indicated with arrow 891. The threads when rotated can induce the carrier 846 to move proximally and distally as shown. As the carrier moves proximally and distally, the second rotatable connector 892 can slide along an elongate structure such as a hexagonal structure 895. The sliding of the carrier in the axial direction can be provided for a range of treatment, for example, up to about 7 millimeters. The second rotatable connector 892 can be rotated so as to induce rotation of the carrier. For example, rotation of the second rotatable connector can cause the angular rotation of the carrier as shown with rotational arrow 893. Rotation of the second rotatable connector can rotate a gear 805 of the linkage that is coupled to the carrier 846. The gear of the linkage can be concentric with the carrier so as to induce rotation of the carrier about an elongate axis of the carrier. The second rotatable connector can comprise a second gear that is concentric to the rotatable connector in order to induce rotation of the gear that is concentric with the carrier. The linkage may comprise an idler gear, for example, between the first gear and the second gear in order to induce angular rotation of the energy source with respect to the elongate axis of the carrier.

Figure 8Q:
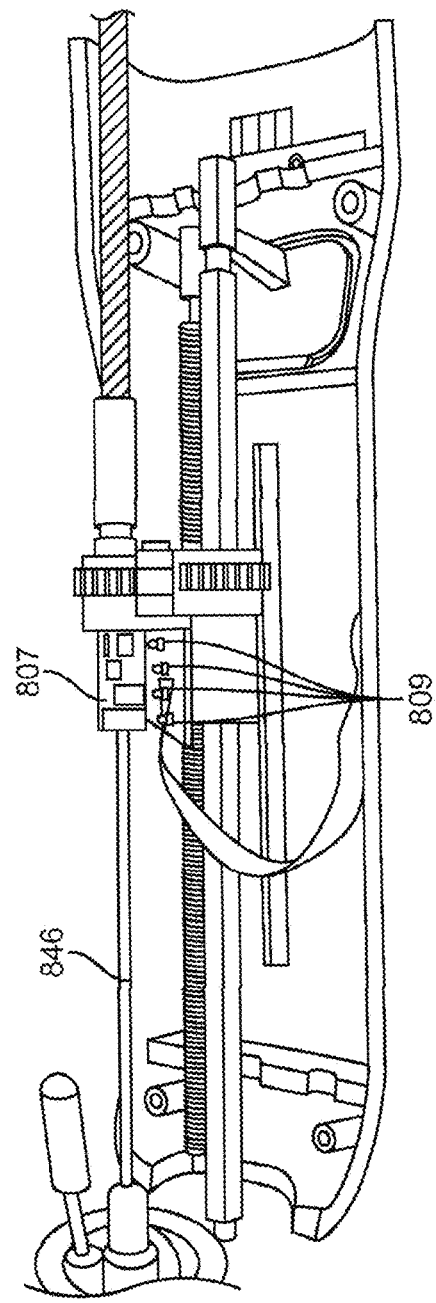
FIG. 8Q shows an encoder mounted on the proximal end of the carrier.

FIG. 8Q shows an encoder 807 mounted on the proximal end of the carrier 846. The encoder on the proximal end of the carrier can allow accurate rotational positioning of the angle of the energy source. The carrier can be rotated to a target position in response to signals measured from the encoder. The encoder on the proximal end of the carrier may comprise one or more of many known encoders. In many embodiments, the encoder comprises a Gray encoder configured to provide quadrature measurements. The encoder can be provided on the face of the carrier, for example, with an annular structure extending from the carrier so as to provide an accurate surface to affix the encoder to. Also, the photo detectors 809 can be arranged in a line extending along the direction of the carrier probe axis. This can facilitate measurements of the angle of the energy source and can allow the detectors to lie on a plane of a printed circuit board. The encoder can extend on a face of the carrier probe and the carrier probe may comprise a removable carrier treatment probe. Removable carrier treatment probe can extend into the seal as described herein. In many embodiments, the encoder comprises an alignment structure that can be aligned with the energy source carried on the distal tip of the probe to ensure accurate alignment during manufacturing. For example, the encoder may comprise a plurality of edge transitions in which each edge extends in an axial direction. One or more of the edges can be preconfigured so as to align with an angle of the energy source extending from the elongate axis of the probe. For example, the energy source can extend in a radial direction from the axis at the same angle as the edge extends radially from the probe or is located along an angle extending radially from the probe.

FIG. 8R1 shows an encoder 807 in accordance with embodiments. As shown with the encoder, each of the edges 811 corresponds to an angular reference with respect to the probe. For example, a zero degree reference 813 is shown. The zero degree reference is aligned with the energy source extending from the distal end of the carrier.

FIG. 8R2 shows a table 815 showing coordinate references for different transitions measured with a plurality of photo detectors. These positions can give an absolute position of the probe within a certain range. The circuitry as described herein can be configured to interpolate within the position shown in FIG. 8R2. The interpolation can be performed in one or more of many ways. For example, the motors may comprise stepper motors to provide interpolation. Alternatively, the motors may comprise encoders within the motors that can be used to provide the interpolation.

White regions of the table 815 correspond to the steel tube portions of the encoder, while black regions correspond to the black plastic tube portions of the encoder. The steel tube and the black plastic tube can form a plurality of rows distributed along the longitudinal axis of the encoder, each row extending about the circumference of the encoder. Each row can be aligned with a photodetector. For each photodetector A (distal), B, C, and D (proximal), rotational positions of the encoder corresponding to the white regions can correspond to an "on" or "1" binary code, whereas rotational positions of the encoder corresponding to the black regions can correspond to an "off" or "0" binary code.

The configuration of the encoder and the photodetectors in FIGS. 8Q, 8R1, and 8R2 is provided by way of example only, and many other configurations are possible. For example, while FIGS. 8Q, 8R1, and 8R2 show an encoder comprising 4 rows with each row aligned with one of 4 photodetectors, an encoder may have any number of rows aligned with any number of photodetectors in any appropriate configuration. The encoder may comprise one or more additional rows and additional photodetectors aligned with each additional encoder row, to increase the resolution of the encoder and thereby provide more finely tunable positional adjustment of the motors and hence the carrier.

FIG. 8S shows aspiration ports 817 on the distal end 819 of the support 806 in accordance with embodiments. The distal end of the support comprises a plurality of ports 817 to aspirate material from the surgical site. The plurality of ports can be sized to receive tissue resected with the energy source 848. The ports can be positioned at predetermined locations so as to provide a visual guide to the user. For example, the aspiration ports can be located at one centimeter intervals such that the user can readily determine the size and location of tissue at the target site. The user can also evaluate the accuracy and verify the accuracy of the probe during use, for example. The support may comprise a plurality of ports in number from two to about 10, for example. The plurality of ports can be located on an underside of the support facing the carrier 846. The concave shape of the support can improve alignment and provide a space to receive the probe. The aspiration ports on the distal end of the support can be fluidically coupled to the aspiration port (826 in FIG. 8A) on the proximal end of the support near the hub with a channel extending from the port to the plurality of ports, for example. The carrier of the energy source can slide toward the distal end of the support during treatment. The ports can provide a reference structure to determine the location of the carrier with respect to the energy source and can be helpful during treatment to facilitate alignment. The plurality of ports on the distal end of the support can be seen with ultrasound, for example, and can be seen with the endoscope having the field of view as described herein, for example. The plurality of ports can be located between the ball-shaped portion on the distal end and the fixed portion of the tube. As described herein, the carrier probe can be advanced to the distal end of the support and retracted. As shown in FIG. 8S, the carrier of the energy source is shown in a retracted position. The coupling structure 814 is also shown retracted that couples the endoscope to the elongate tube 808. The proximal portion 812 of the tube is shown with the distal portion 810 of the tube having been received therein such that a portion of the irrigation ports 824 is covered with a proximal portion of the tube. The coupling 814 as described herein can be used to advance the elongate tube and the endoscope as described herein. The carrier comprising the energy source can be moved independently of the endoscope in the tube and the coupling, for example. In at least some embodiments, this independent motion can be helpful for treatment. Alternatively or in combination, the coupling can be positioned over the energy source to act as a shield for users of the system from the energy source. For example, when the system is initially set up, the coupling can be slid over the energy source in order to block the energy source. In many embodiments, the coupling comprises sufficient mechanical strength to withstand the energy source and the energy source is configured to resect tissue and also not to destroy the coupling when the coupling is positioned over the energy source.

Figure 8T:
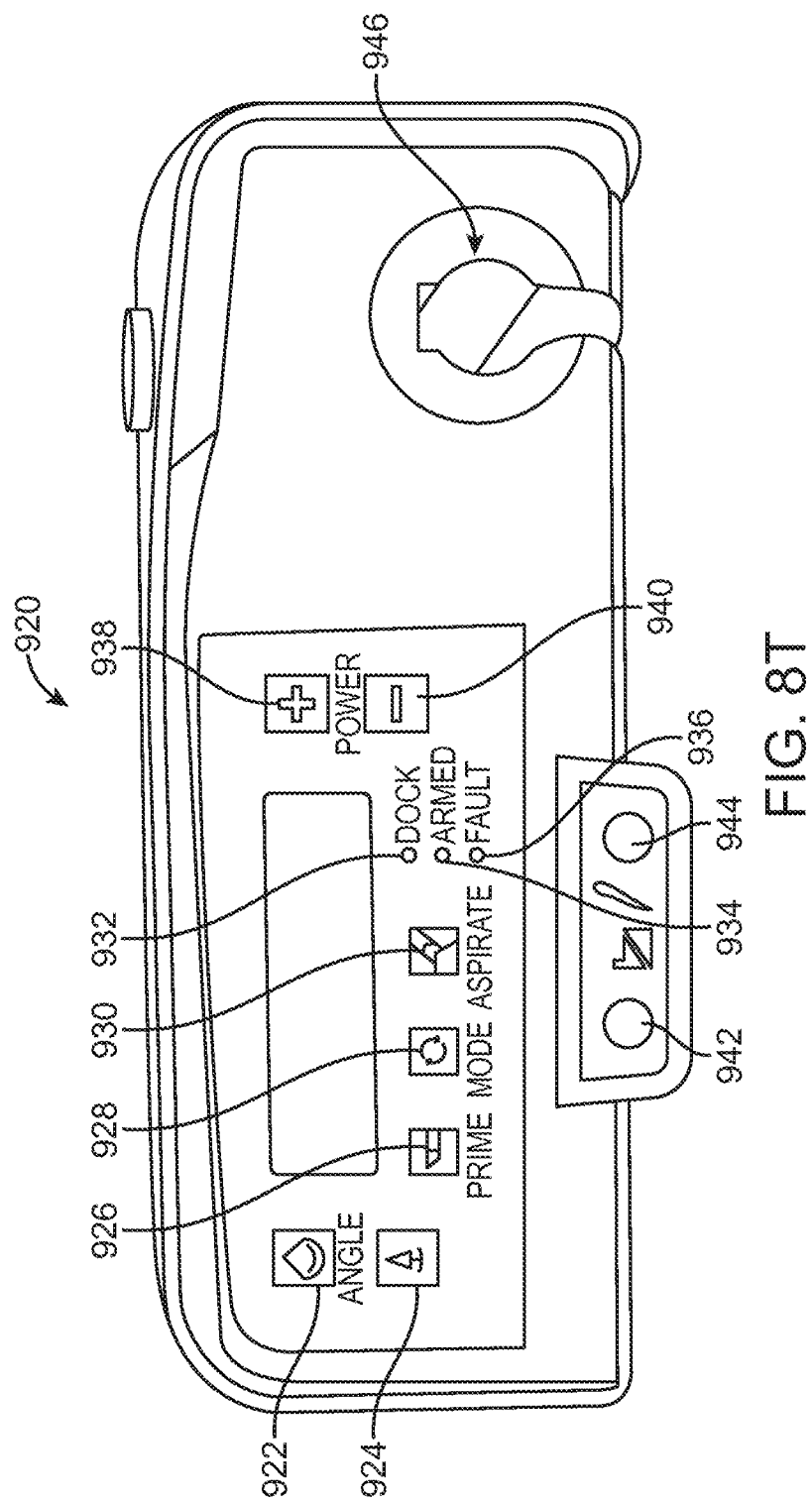
FIG. 8T shows a console in accordance with some embodiments.

FIG. 8T shows a console 920 in accordance with embodiments. The console comprises a plurality of inputs and a plurality of outputs of a user interface that allows the user to program the system for treatment. The console comprises an angle input 922 to increase an angle and a second angle input 924 to decrease an angle. The console comprises a prime input 926 to prime a pump. The console comprises a mode input 928 to set a mode. The console comprises an aspiration input 930 to aspirate. The console comprises outputs such as a dock configuration 932, an arm state 934 and a fault state 936. The power can be increased or decreased to the energy source as shown with the plus 938 and the minus 940. Inputs for a foot pedal 942 and a hand control 944 are shown. The foot pedal may comprise a standard commercially available foot pedal and the hand control may comprise a plus and minus control on the arm as described herein. The high pressure tube can be attached to a channel or connector 946 coupled to a high pressure pump.

Figure 9A:
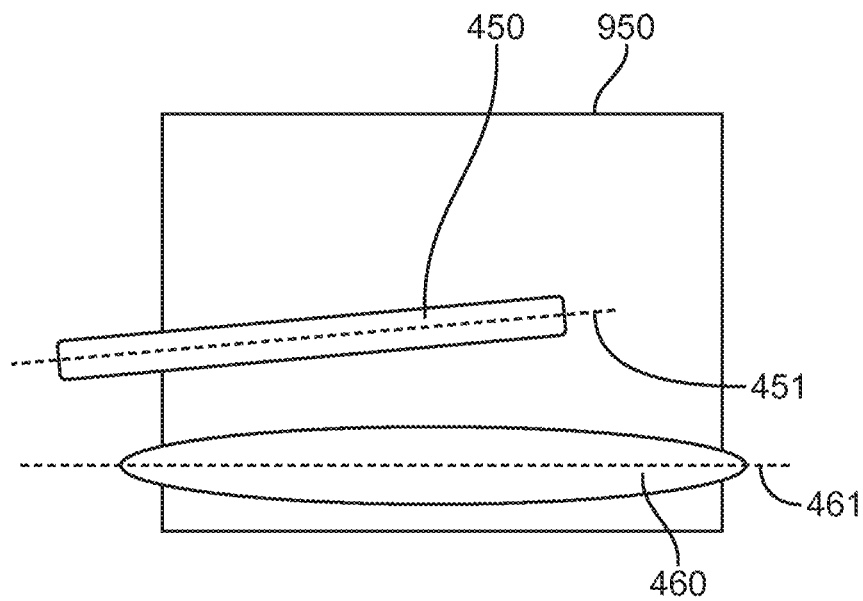
FIGS. 9A and 9B show side and top views, respectively, of alignment of a treatment probe axis with a sagittal plane of an imaging probe, in accordance with some embodiments.
Figure 9B:
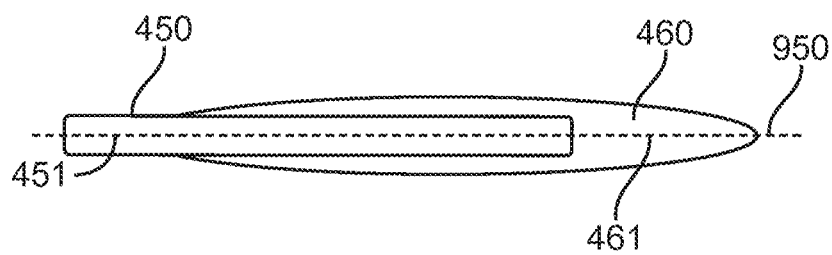

FIGS. 9A and 9B show side and top views, respectively, of alignment of a treatment probe axis with a sagittal plane of an imaging probe. FIG. 9A shows a treatment probe 450 that is inclined relative to an imaging probe 460. The imaging probe comprises an elongate axis 461 that provides a reference for the images. In many embodiments, the imaging probe comprises an elongate axis. The imaging probe may comprise an ultrasound probe having an elongate axis that at least partially defines a sagittal image plane 950. In many embodiments, the imaging probe comprises a sagittal image field of view, and the treatment probe 450 is substantially aligned with the sagittal plane of the imaging probe when the treatment probe is within the field of view of the sagittal image.

Although reference is made herein to a trans-rectal ultrasound (TRUS) imaging probe, the imaging probe may comprise one or more of many known probes such a non-TRUS probe, an ultrasound probe, a magnetic resonance probe, and endoscope or fluoroscopy, for example.

The user can use images of the treatment probe obtained with the imaging probe to align the treatment probe with the imaging probe. In axial mode, the treatment probe can appear distorted when the imaging probe is not sufficiently aligned with the treatment probe. The distortion of the treatment probe can depend on the cross-sectional shape of the treatment probe. For example, a disc shaped cross-sectional profile may appear as a distorted crescent shape in axial mode. In sagittal imaging mode, only a portion of the elongate probe extending through the sagittal field of view will appear in the image. The user can be prompted to align the probes until sufficient alignment is obtained in order to view the treatment probe, for example with inhibited distortion of the treatment probe in the axial mode and with a view of the elongate treatment probe along a substantial axial distance of the probe, e.g. 5 cm, in the sagittal image.

In many embodiments, as shown in FIG. 9B, the elongate axis 451 of the elongate treatment probe 450 is substantially aligned with the sagittal image plane 950 when a substantial portion of the elongate treatment probe is visible in the sagittal image, e.g. 5 mm.

Figure 9C:
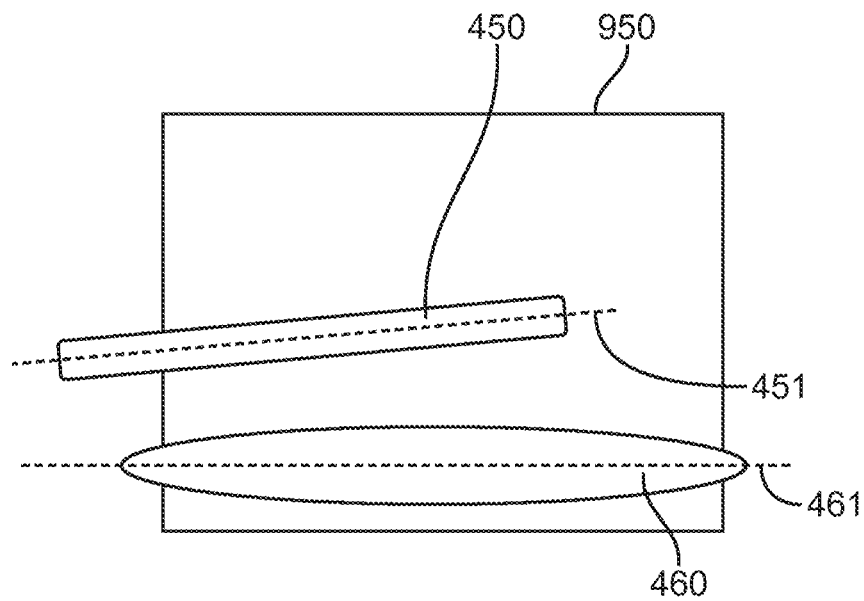
FIGS. 9C and 9D show side and to views, respectively, of a treatment probe traversing a sagittal image plane field of view, in accordance with some embodiments.
Figure 9D:
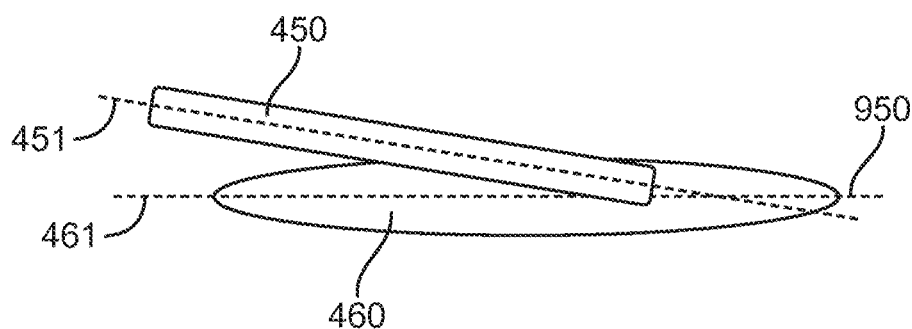

FIGS. 9C and 9D show side and top views, respectively, of a treatment probe 450 traversing a sagittal image plane

950 field of view. The user can be prompted to improve alignment to a configuration similar to FIGS. 9A and 9B, for example.

There can be residual alignment errors corrected with software instructions of the processor in response to images of the treatment probe measured with the imaging probe. In many embodiments, the elongate axis of the treatment probe can appear rotated in the images. The system software can be configured to measure the rotation and rotate the images. For example, users can be trained to see sagittal images in which the axis of the imaging probe is used as a reference. To plan treatments, however, the users may better visualize the treatment when the elongate axis of treatment probe appears horizontally on the user screen, or vertically, for example. In many embodiments, the software measures an angle of rotation of the treatment probe in the image such as a TRUS image and rotates the image in response to the rotation of the treatment probe. For example, the system software may measure an angle of one degree of rotation and rotate the image accordingly such that the rotation angle appears to be zero degrees to the user.

Figure 10A:
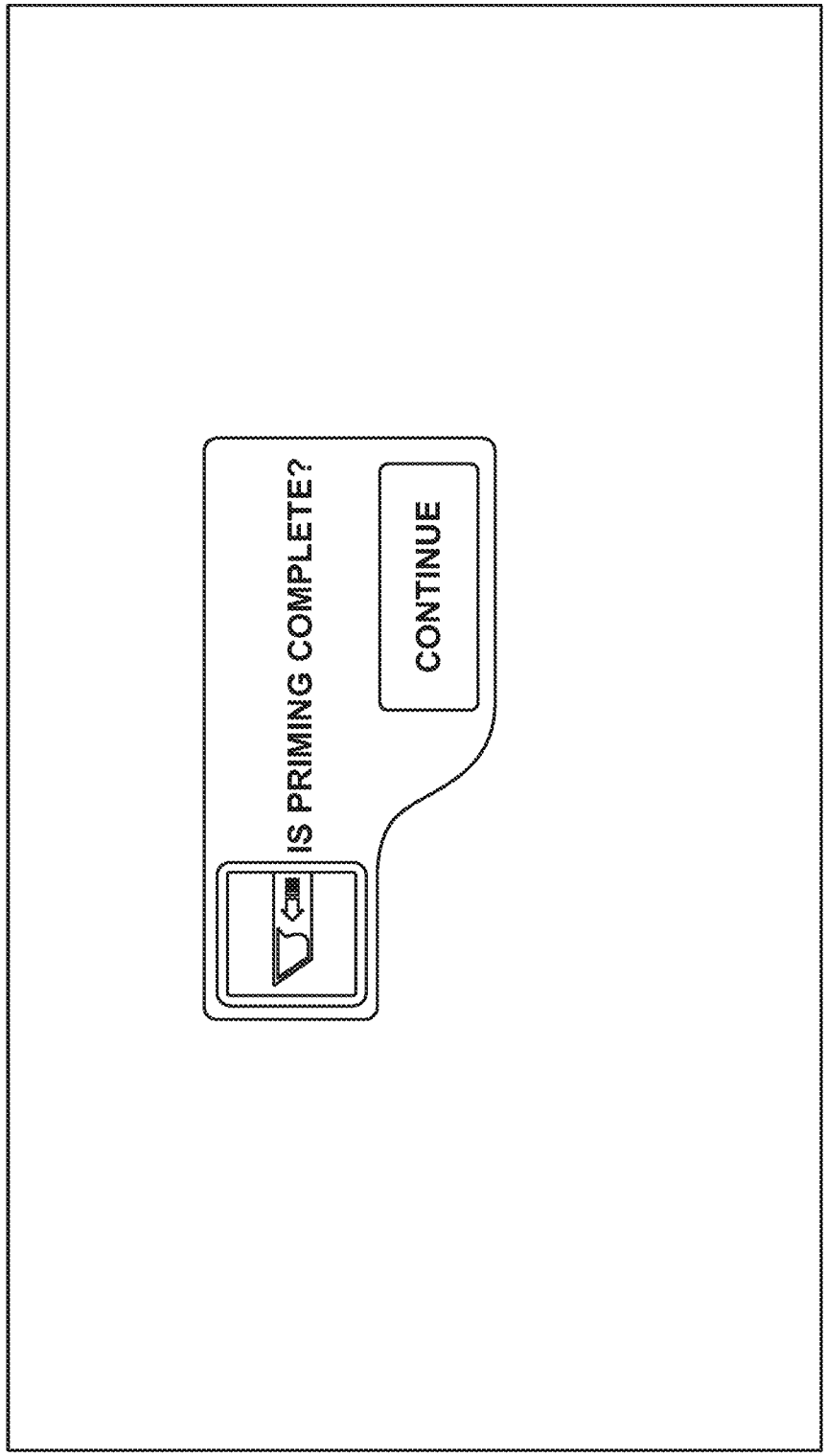
FIGS. 10A-10T show treatment screens of an apparatus, in accordance with some embodiments.
Figure 10B:
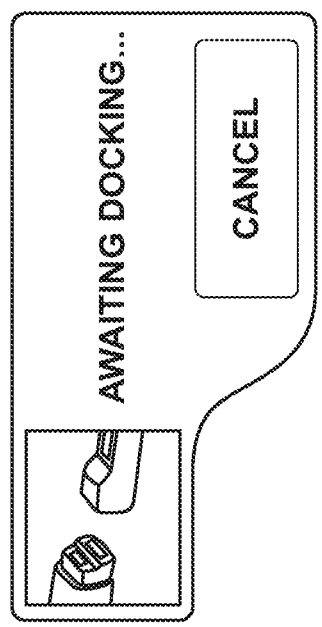
Figure 10C:
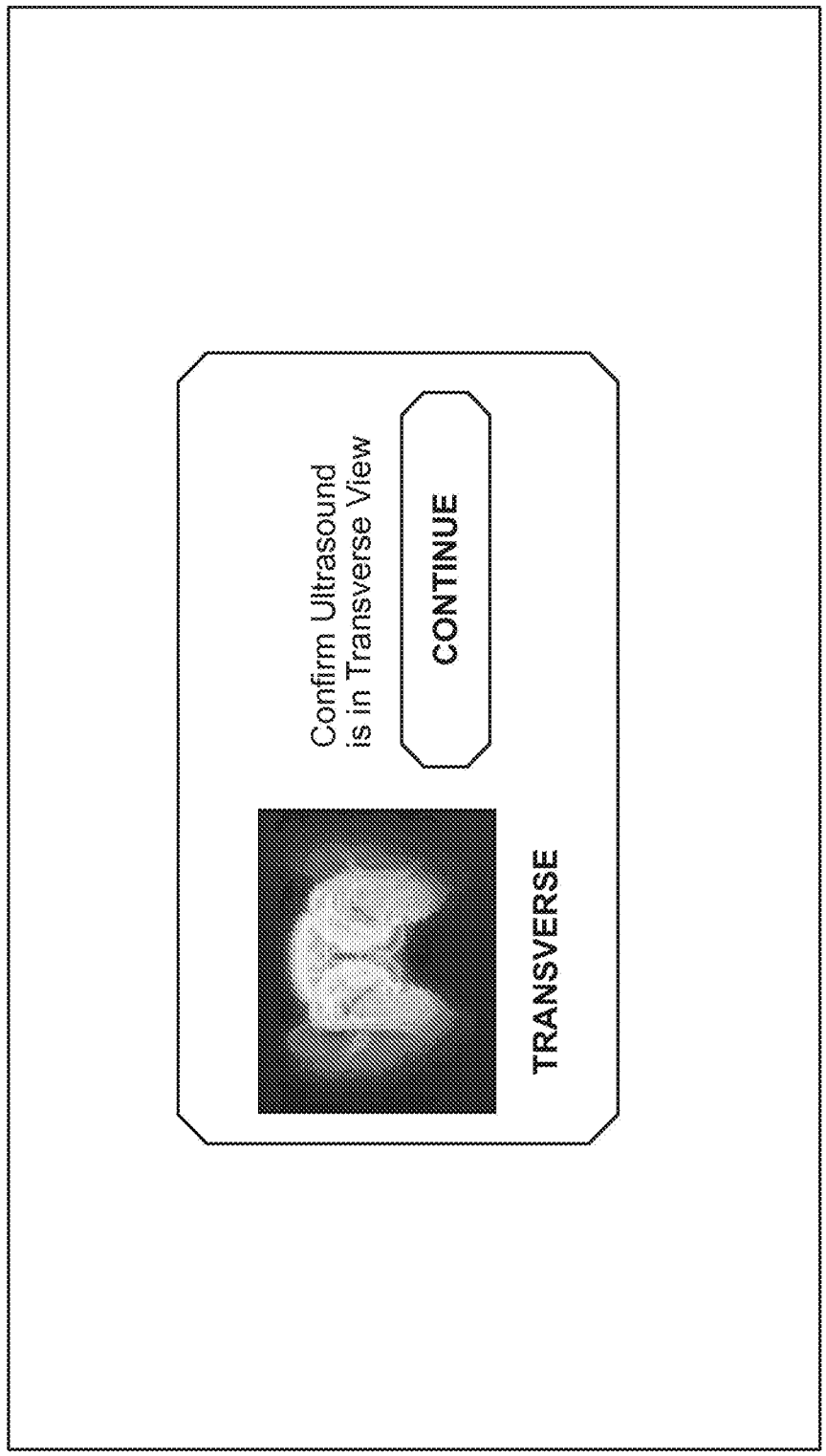
Figure 10D:
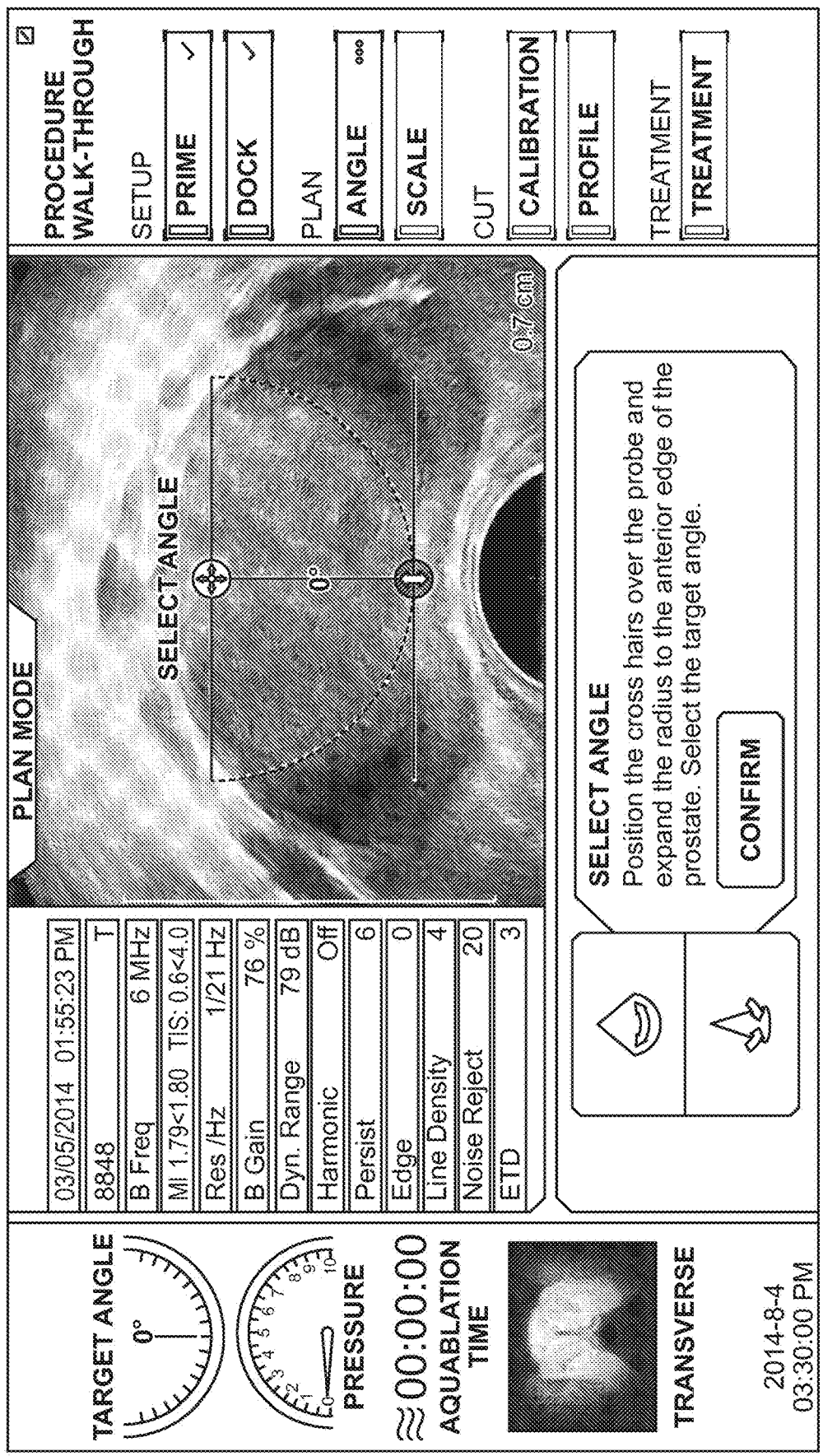
Figure 10E:
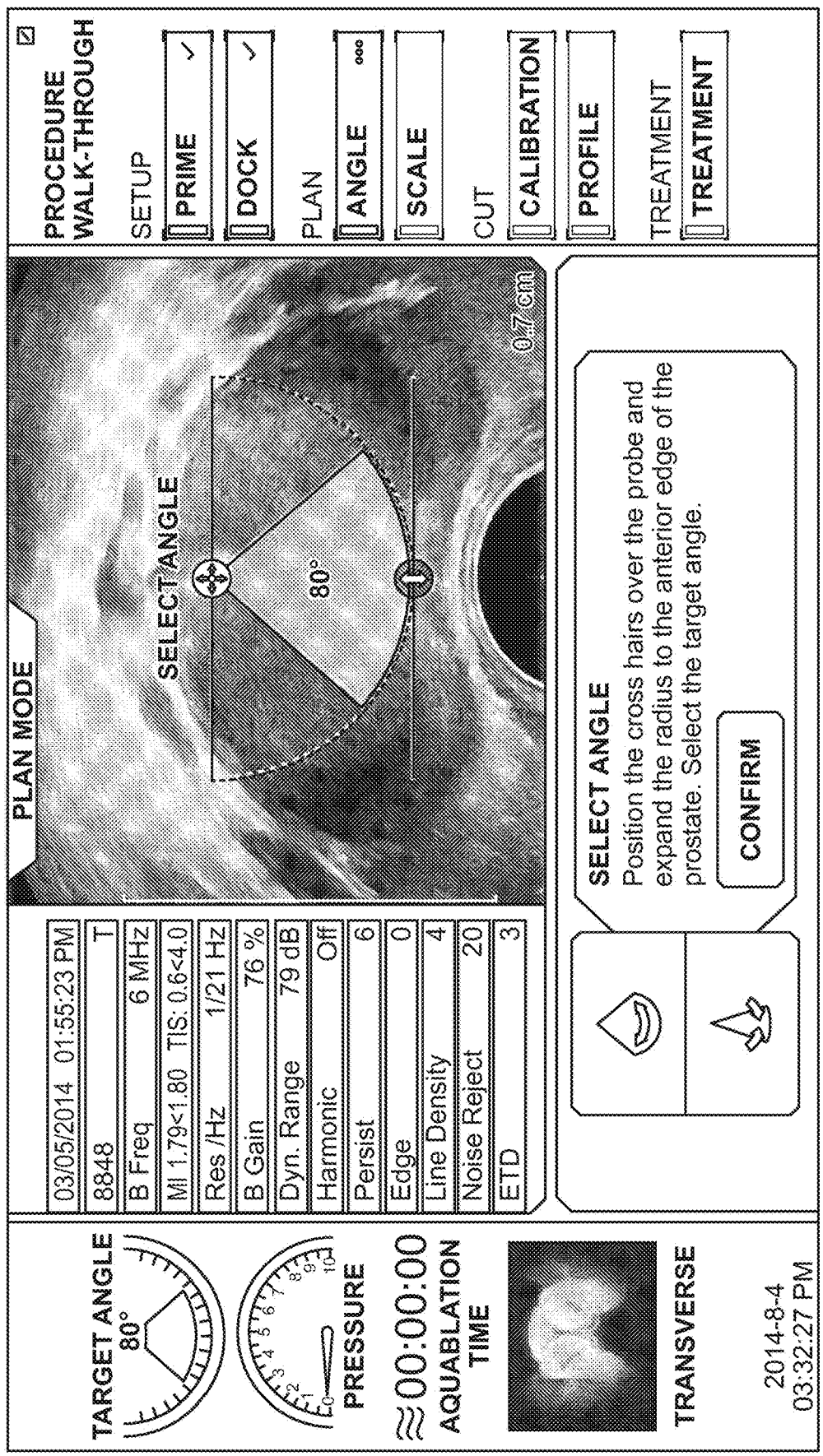
Figure 10F:
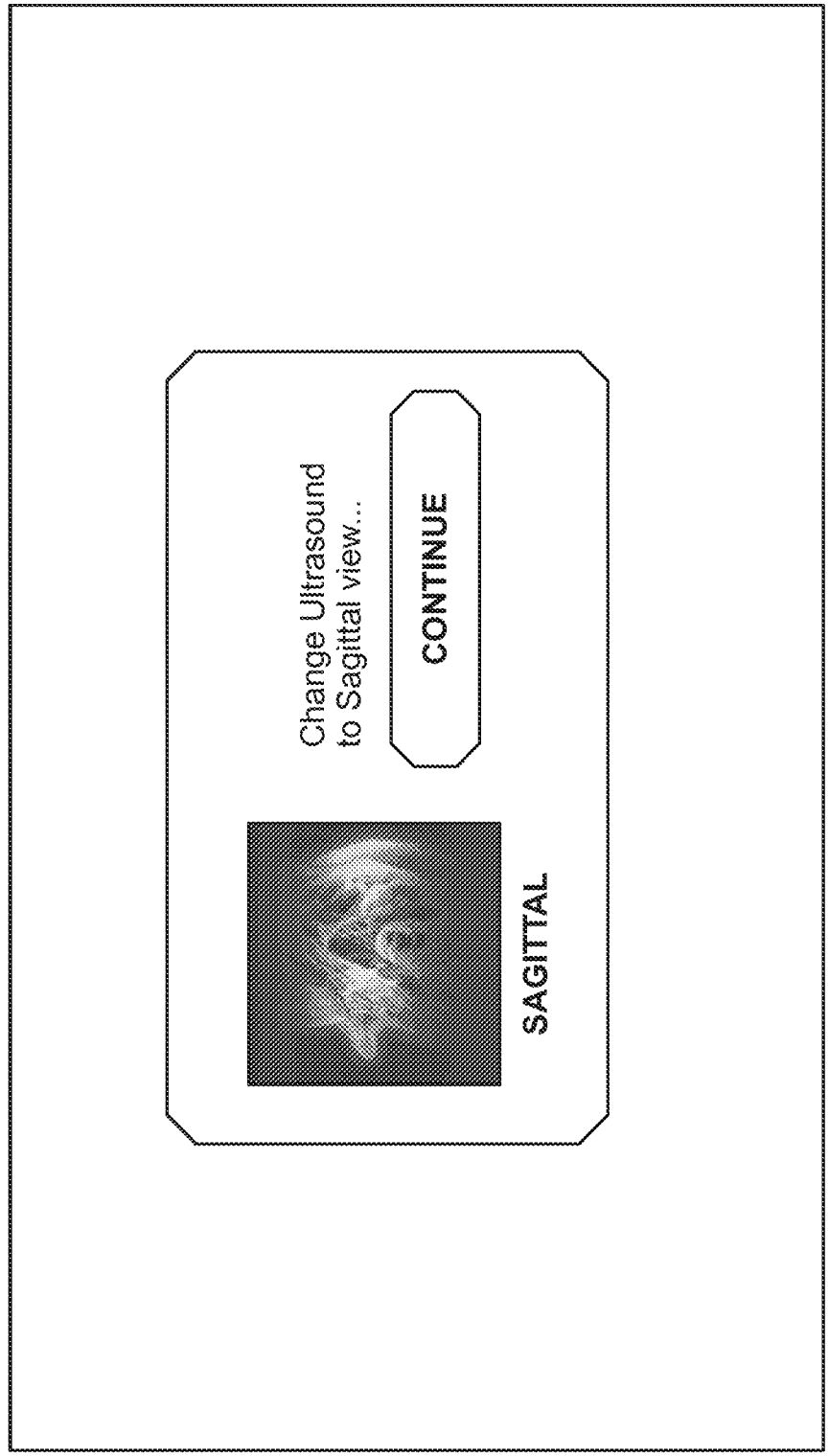
Figure 10G:
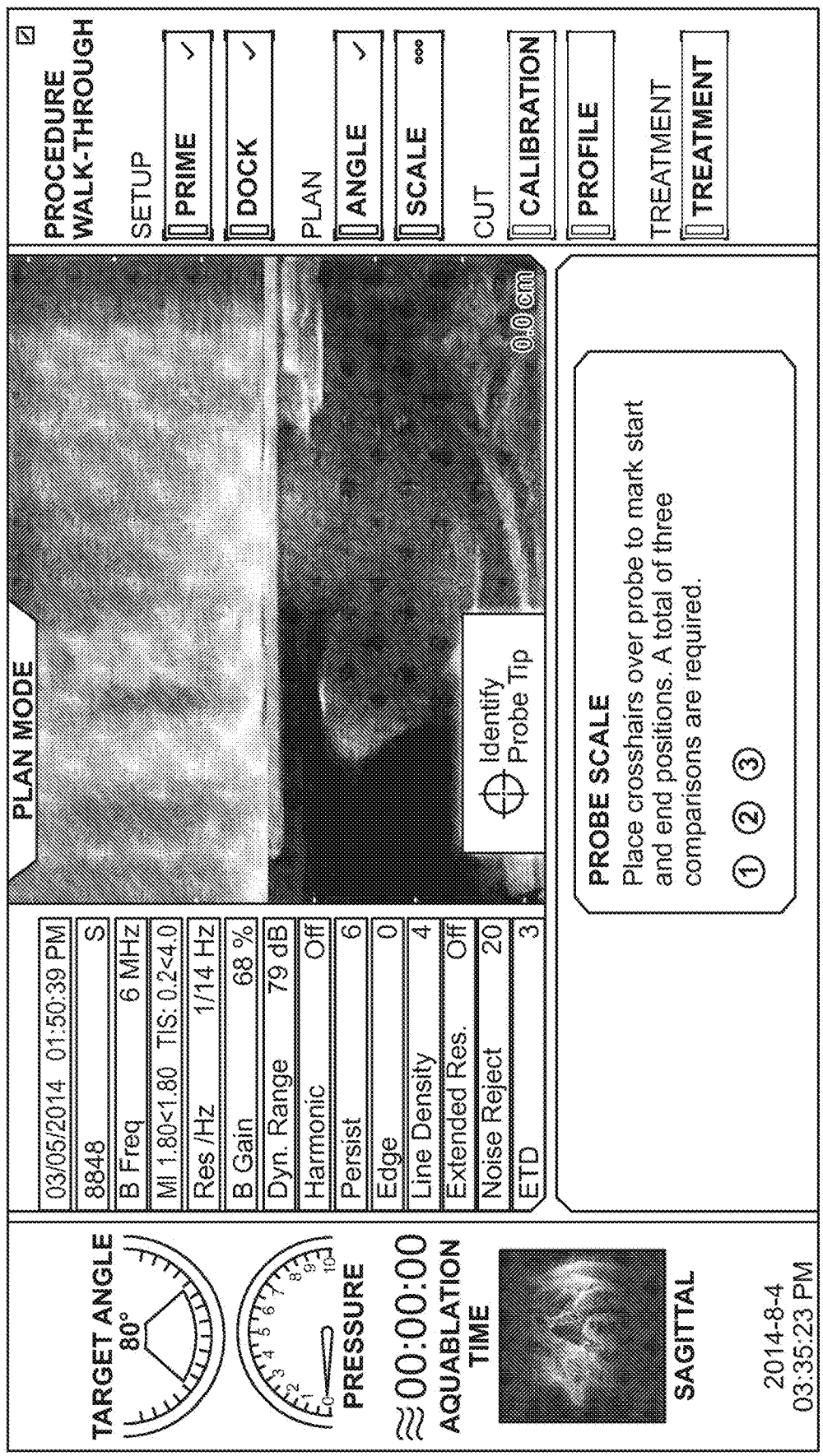
Figure 10H:
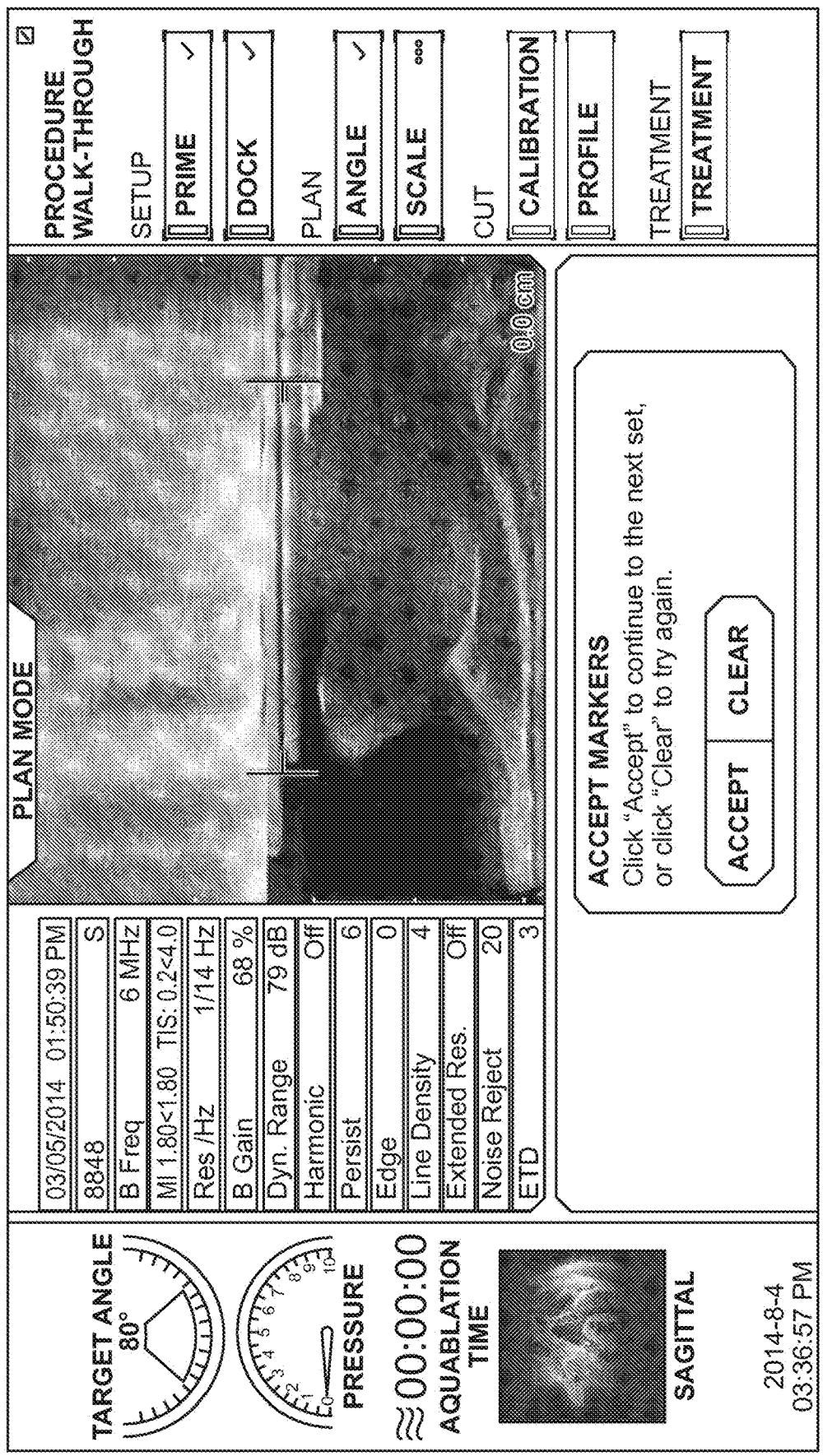
Figure 10I:
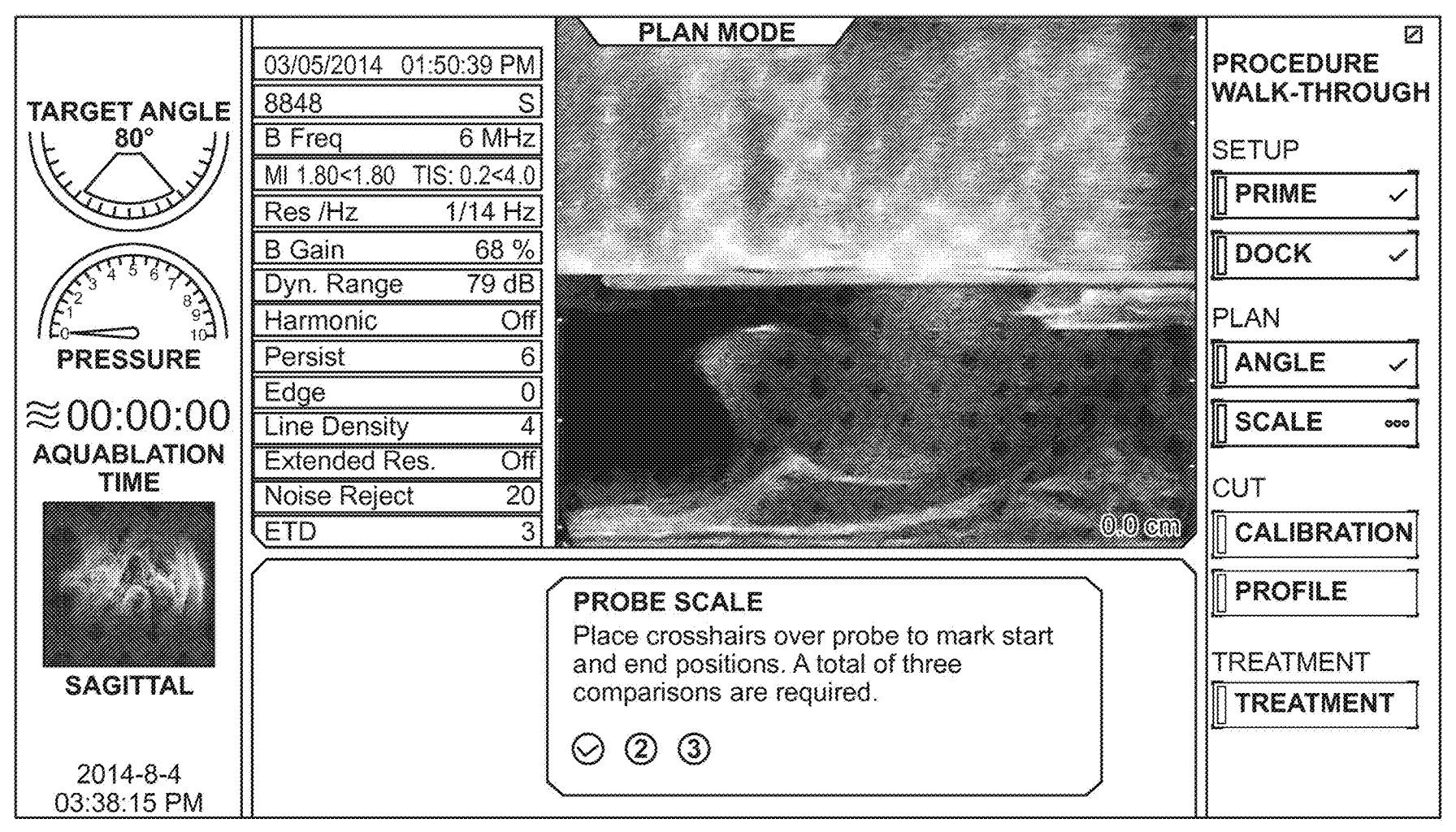
Figure 10J:
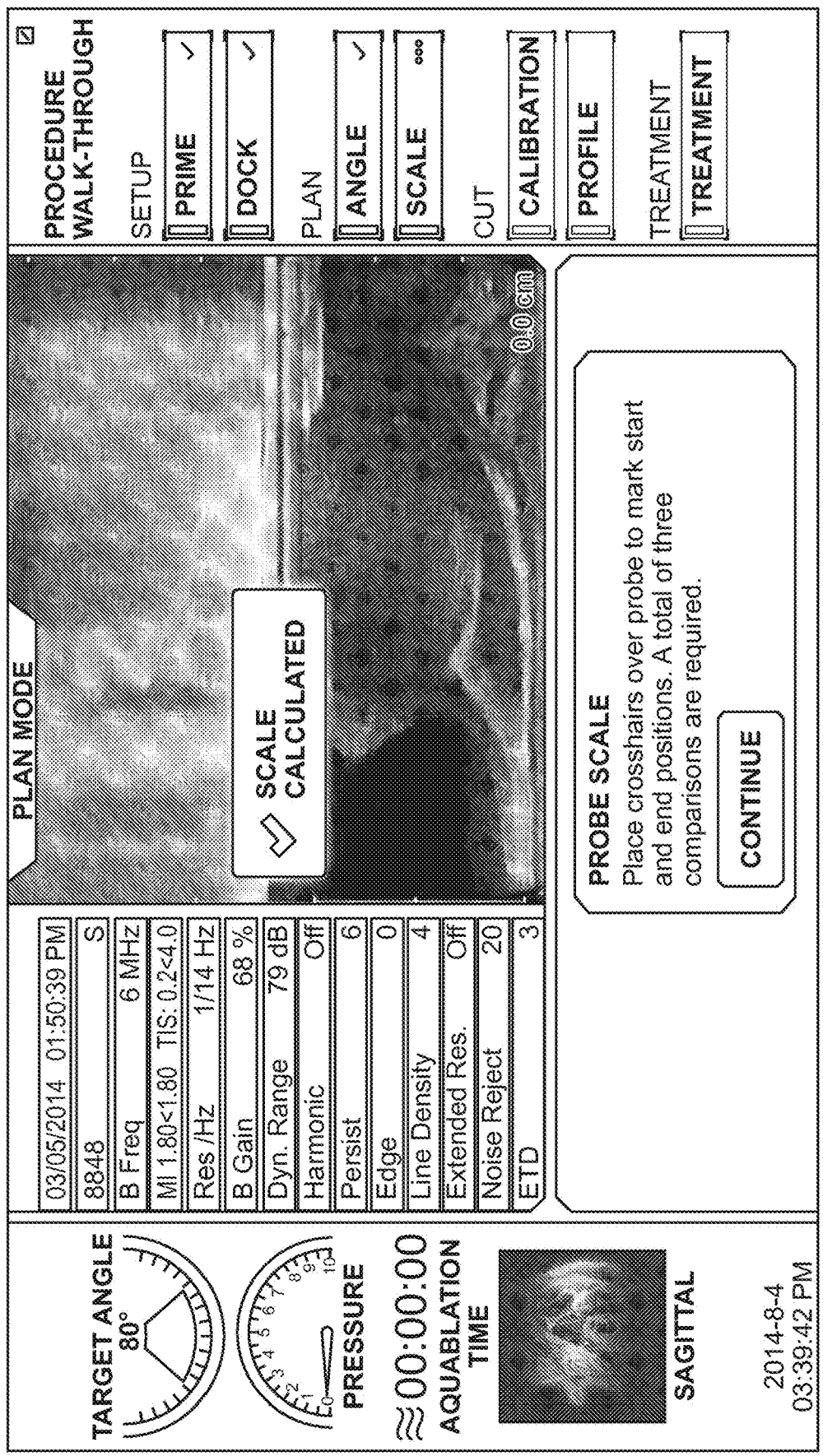
Figure 10K:
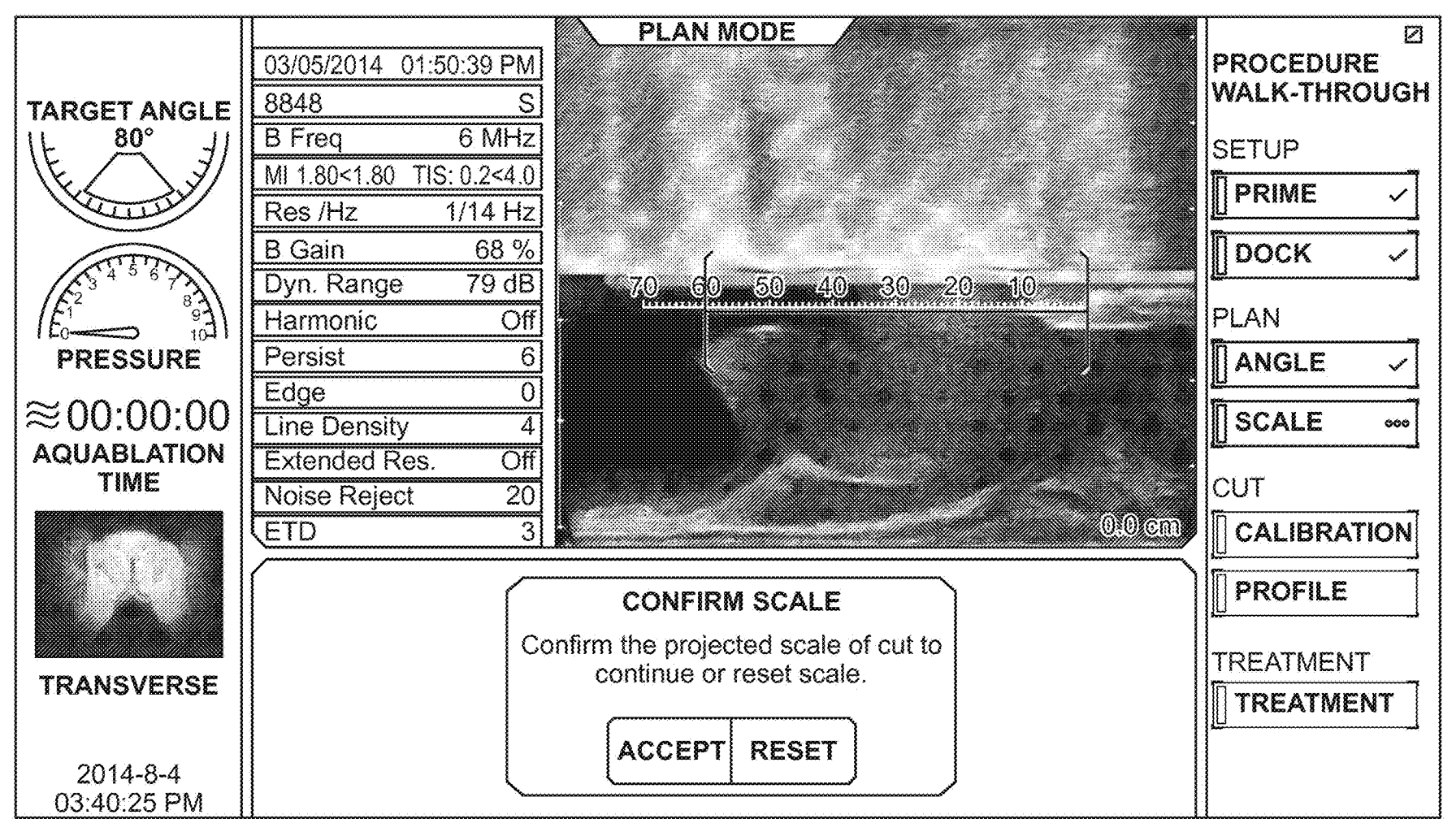
Figure 10L:
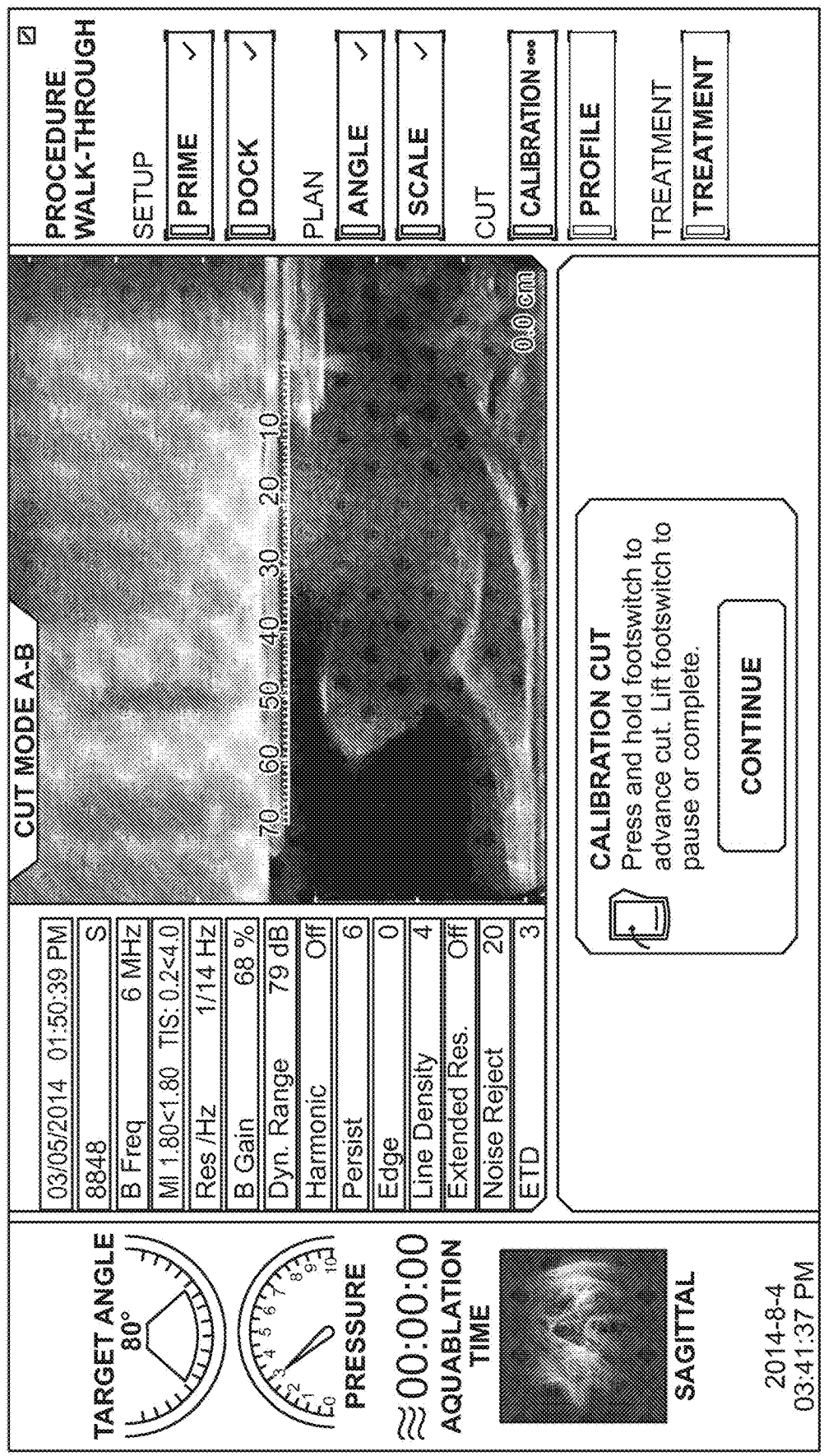
Figure 10M:
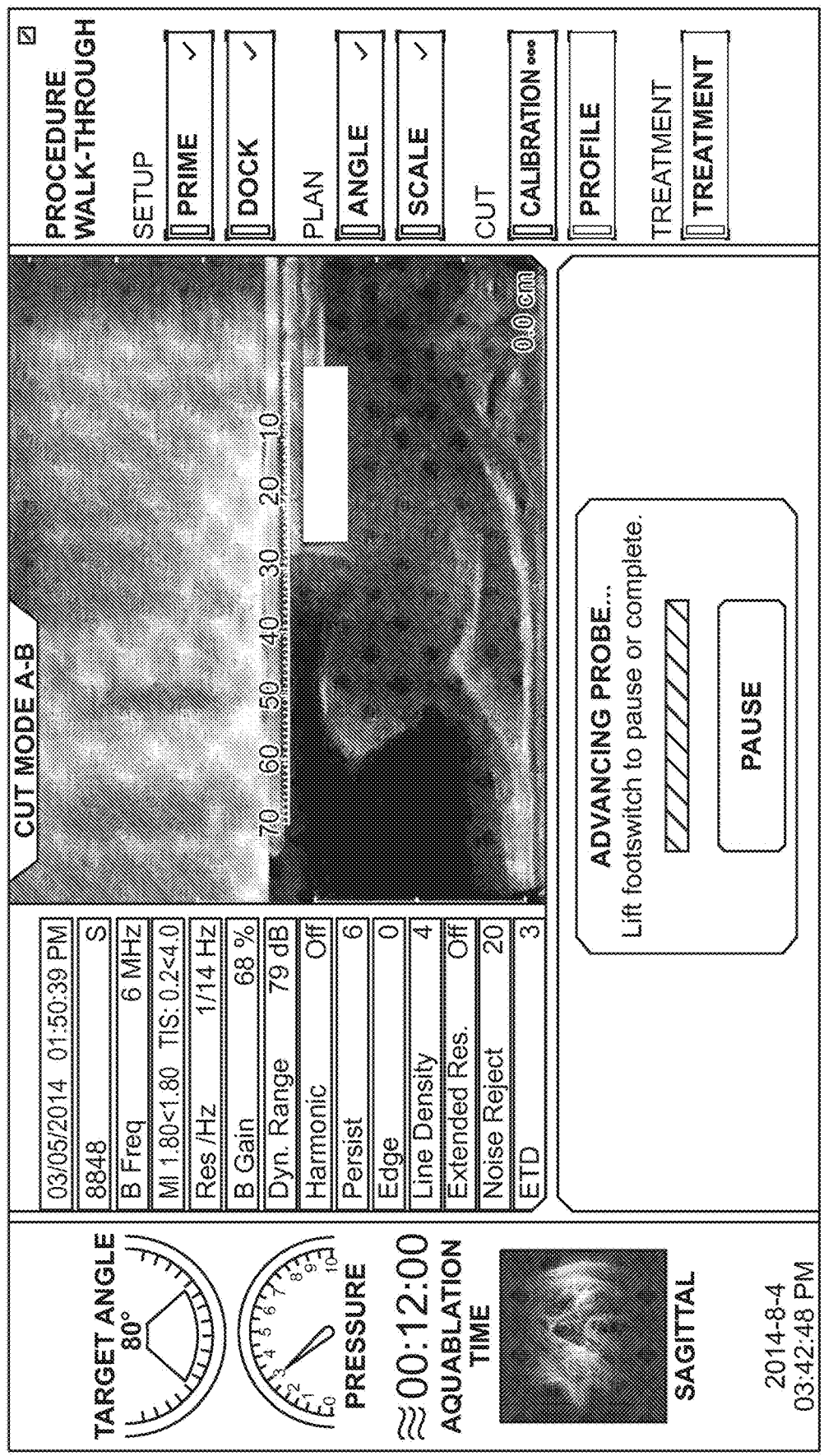
Figure 10N:
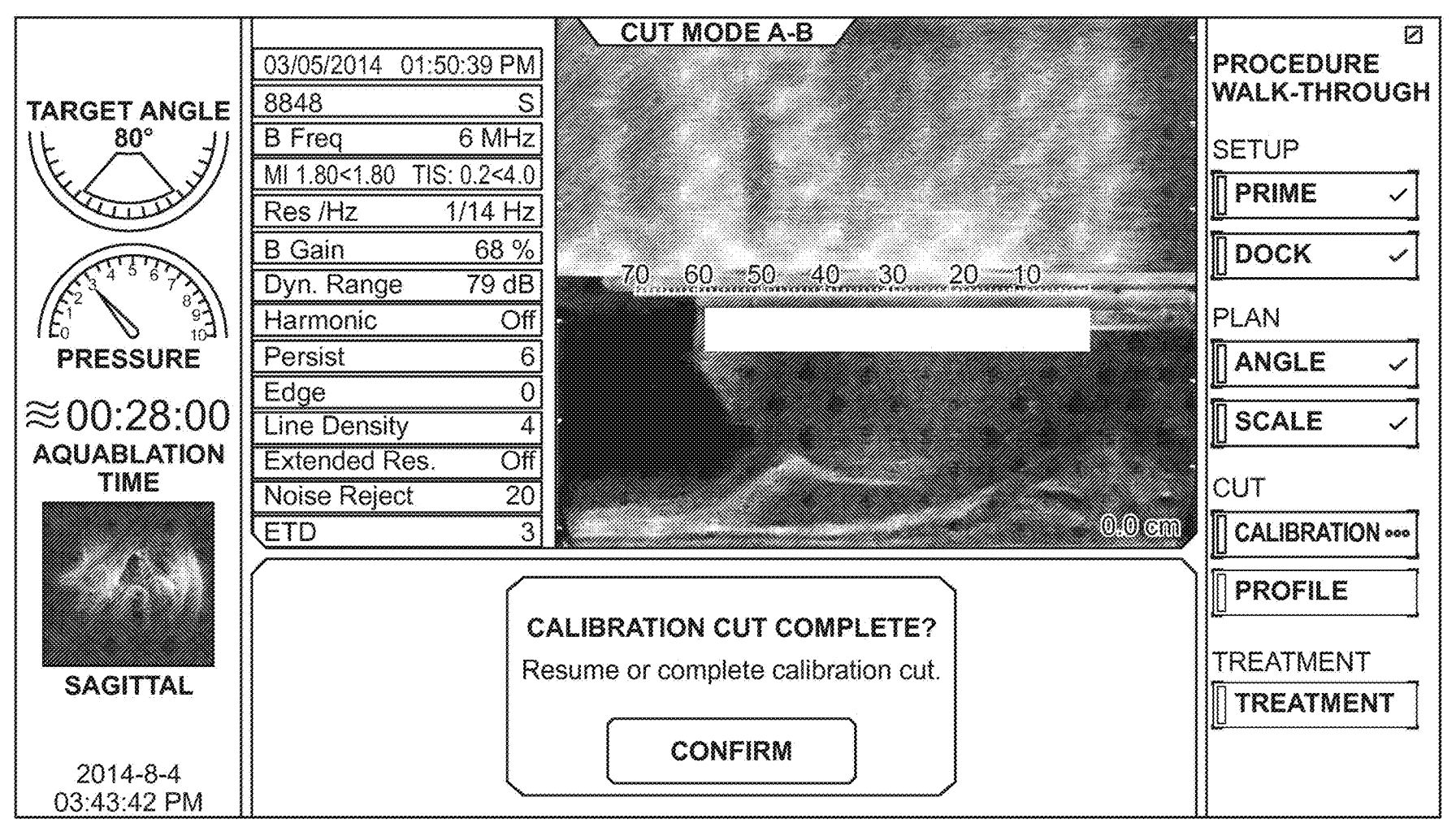
Figure 10O:
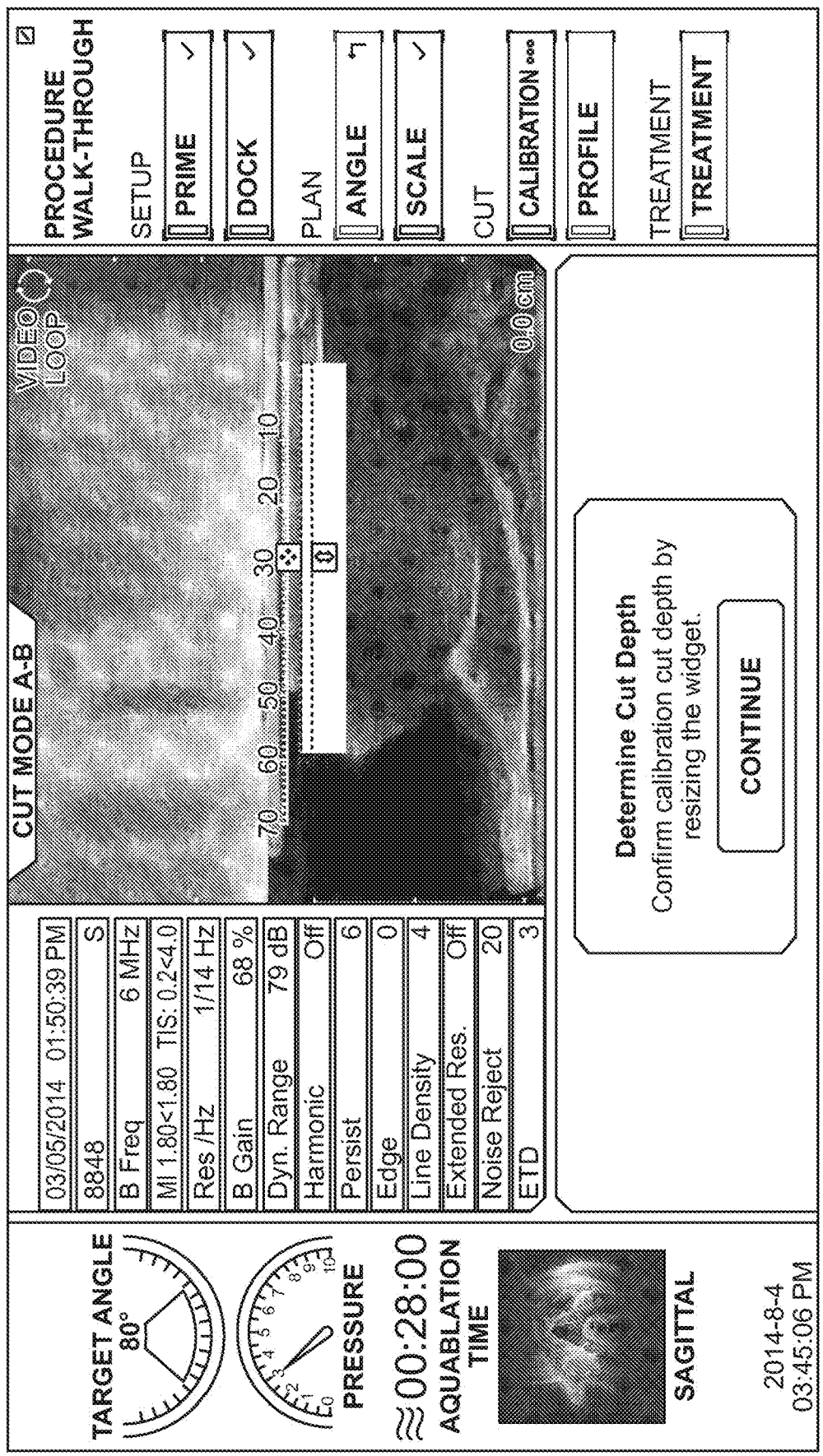
Figure 10P:
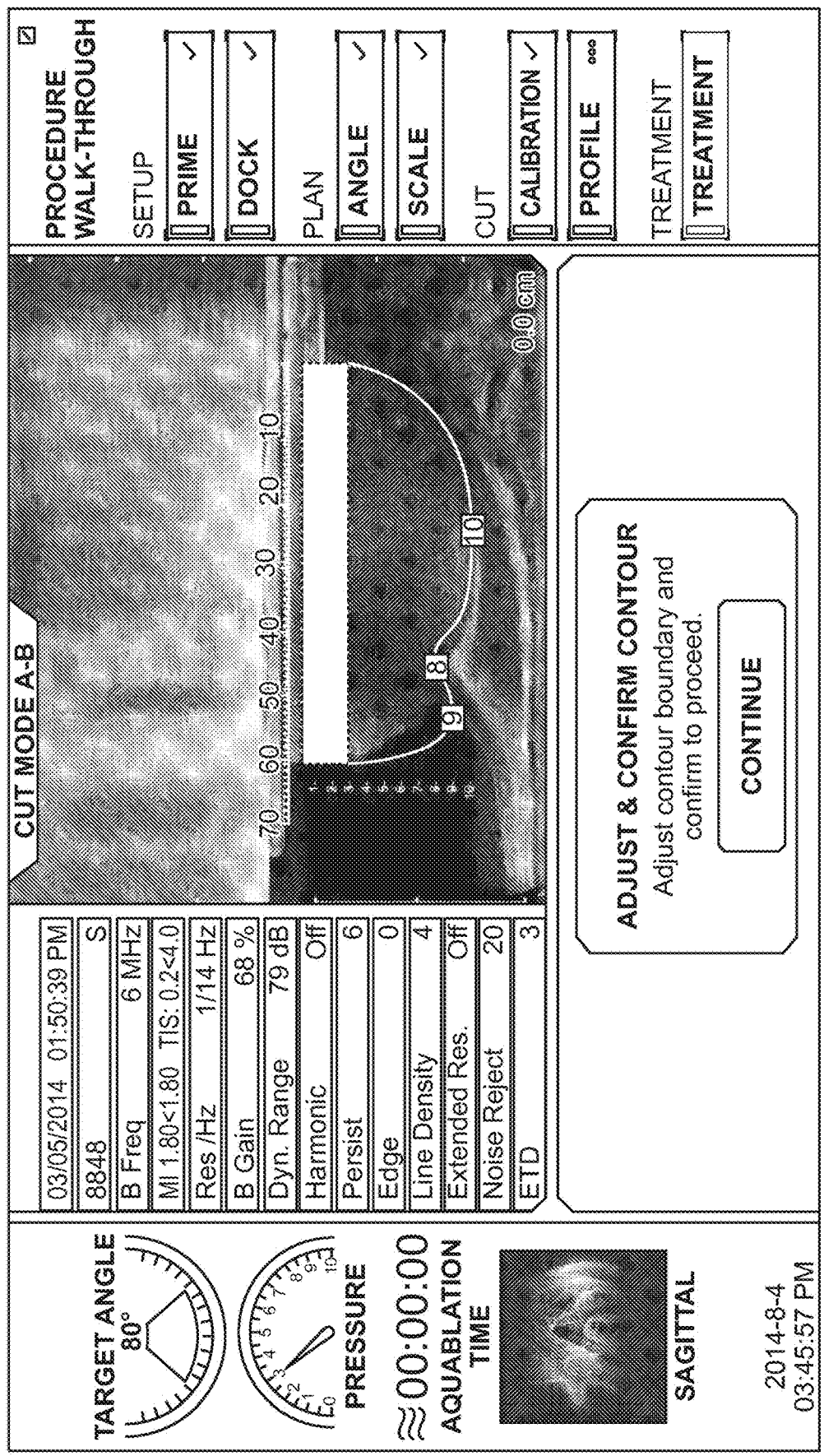
Figure 10Q:
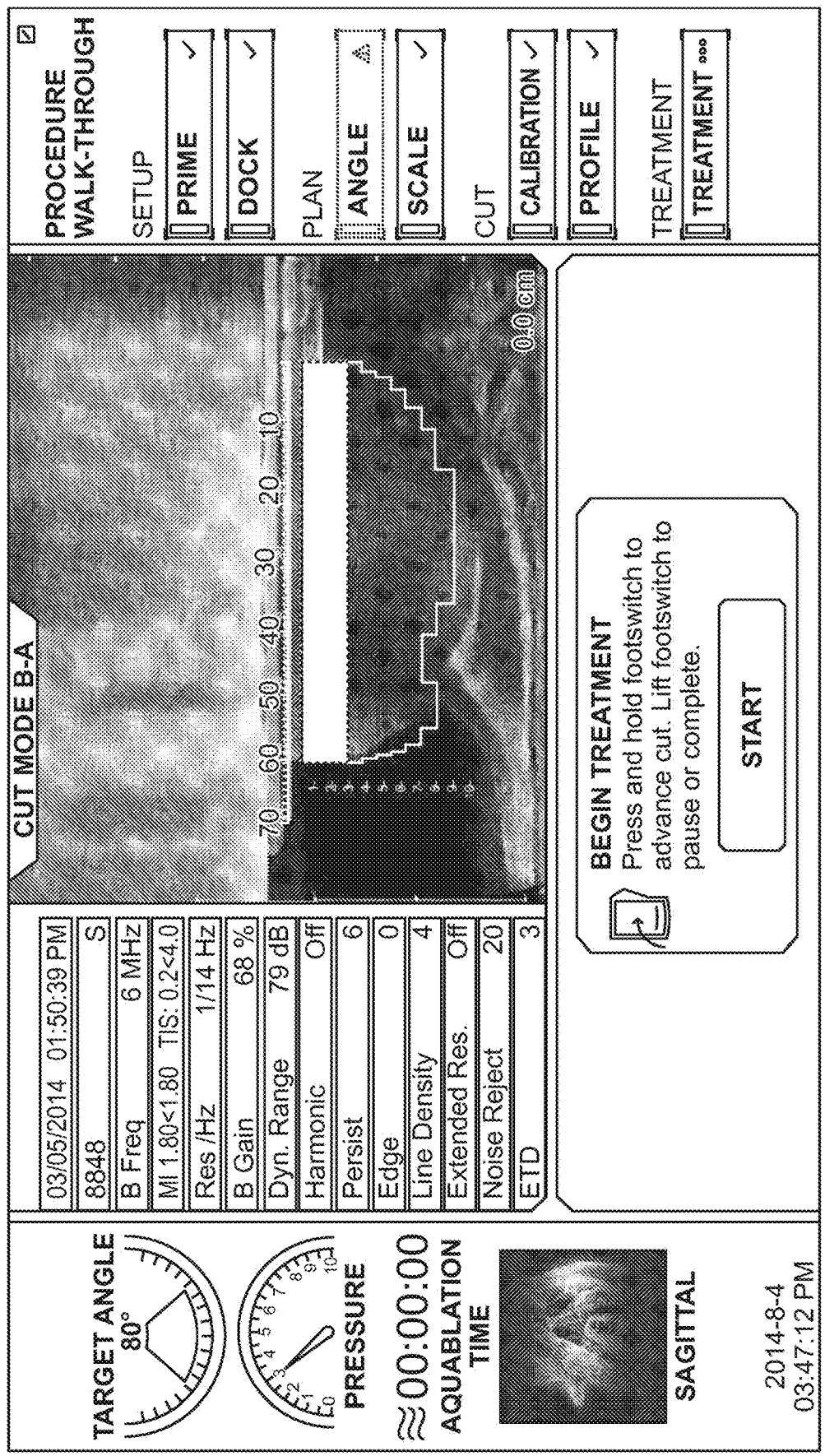
Figure 10R:
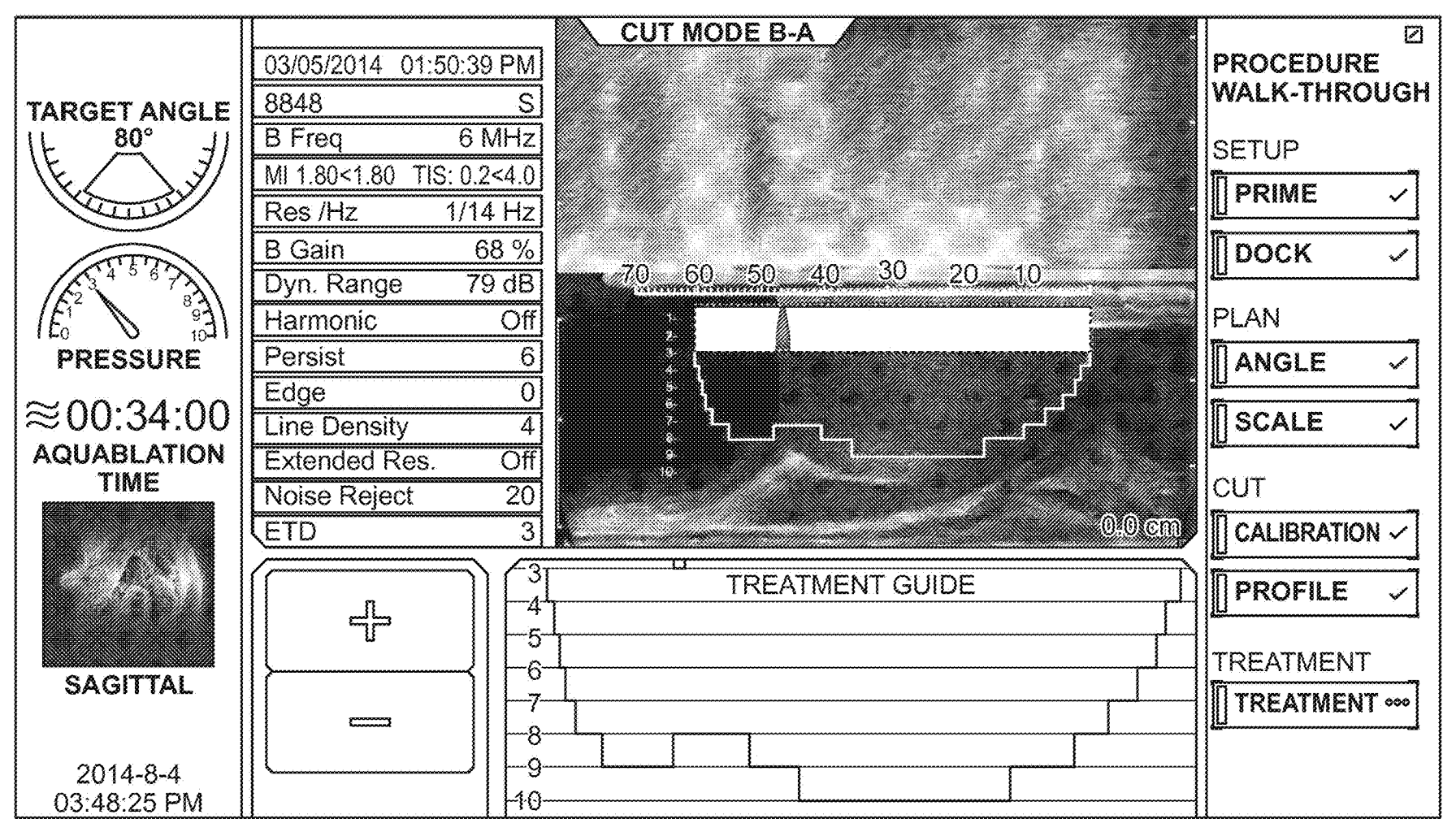
Figure 10S:
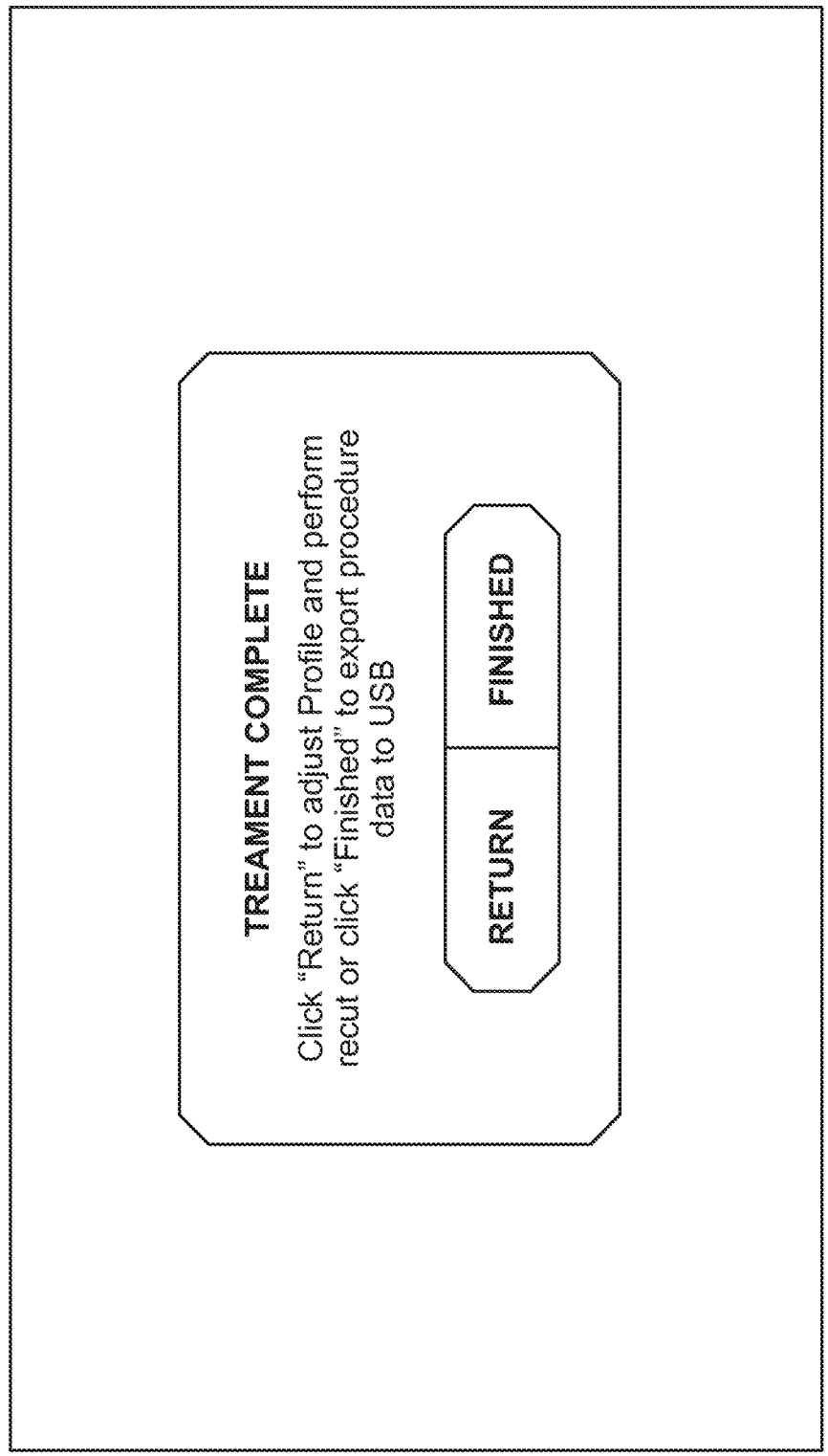
Figure 10T:
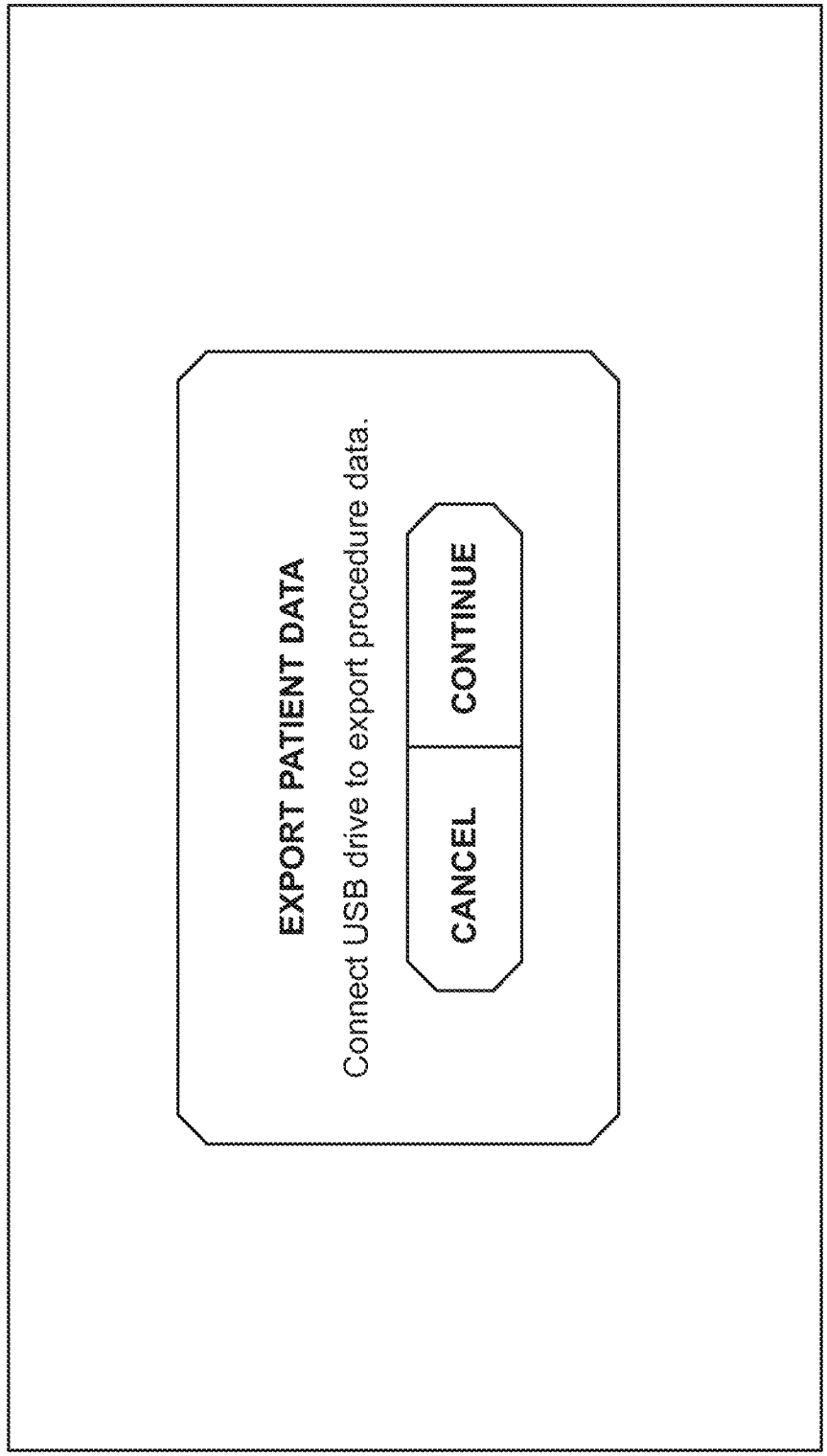

FIGS. 10A-10T show treatment screens of an apparatus, in accordance with embodiments.

FIG. 10A shows a priming verification screen in accordance with embodiments. The priming verification screen comprises a user input for the user to hit a continue button upon completion of the priming. The priming is performed in order to prime the pump. It can be used to provide the energy source such as the fluid stream. While the reference is made to a pump, the energy source could comprise another energy source or an alternative energy source such as an electrical energy source for example. Upon completion of the priming, the user hits continue.

FIG. 10B shows an awaiting docking screen in accordance with embodiments. With FIG. 10B, the user is prompted to dock the system. The system can be docked by placing an attachment onto the arm as described herein. Once the attachment has been docked to the arm, the system automatically advances to the next step.

In many embodiments during the docking step, rotating couplings of the arm are provided in order to align the couplings of the arm with the attachment comprising the hand pieces described herein.

FIG. 10C shows a prompt for the user to confirm that the ultrasound is in transverse view. The screen can provide an ultrasound image of a transverse view in order to orient the user and confirm that the ultrasound probe is in a proper transverse view. Once the user has looked at the ultrasound system and confirmed that the ultrasound is in transverse view, the screen of the user interface provides a continue button for the user to provide input. Upon inputting continue, the user is prompted with the next screen.

FIG. 10D shows an angle select input screen. The select angle input screen allows the user to select a treatment angle. The input screen comprises a plurality of icons; the first icon showing an increased angle, and the second icon showing a decreased angle. The user uses an input device such as a cursor and a mouse to click on the appropriate icon to increase the angle. For example, if the user desires to increase the angle, the user clicks on the icon comprising the outwardly extending arrows in order to increase the treatment angle. Once a treatment angle has been selected, the user can input confirm by hitting the confirm button. Selecting the angle in the transverse view allows the user to adjust the treatment angle to the patient anatomy. The treatment angle can be within a range from about 1 degree to 180 degrees for example. In many embodiments, the treatment angle is within a range from about 10 degrees to about 170 degrees.

FIG. 10E shows an angle selected in accordance with embodiment. In FIG. 10E, a selected angle of 80 degrees is shown for example. Once the user has selected a desired angle, the user can hit the confirm button to move onto the next user input screen.

FIG. 10F shows a prompt for the user to change the ultrasound to a sagittal view. Upon changing the ultrasound to the sagittal view, the user can hit the continue button with an input device such as a mouse or touch screen display. The input shown to the user can show an icon showing a sagittal ultrasound view to orient the user with respect to the sagittal view.

FIG. 10G shows a probe scale user input screen. The probe scaling user input screen can be used to set the scale of the probe in relation to the ultrasound image. The probe can be seen in the upper right hand corner of the sagittal image. The cross hairs can be placed over a movable mark to identify the probe. In many embodiments, the user is prompted to identify the probe tip by placing the cross hair over the probe tip. When the user has placed the cross hair over the probe tip, the instrument receives a command from the input that the probe tip has been identified.

When the probe tip has been identified, the instrument advances the carrier probe to a distal location.

FIG. 10H shows the carrier probe tip advanced to a distal location. The carrier probe tip can be seen with a marker identifying the end of the carrier probe tip. The user can be prompted to identify the carrier probe tip in the second configuration. As shown in FIG. 10H, the first position of the carrier probe tip which is a proximal location as shown with a marker, and the second location of the carrier probe tip which is a distal location as shown with a second marker.

While the carrier can be configured in one or more of many ways to perform the calibration and image guided definition of the treatment as described herein, in many embodiments, a probe comprising a support as described herein is used.

Referring again to FIG. 10G, the probe tip can be seen in a proximal location with the elongate support extending distally a substantial difference. As can be seen in FIG. 10H, the probe tip extends a substantial distance which is closer to the distal end of the elongate support as described herein.

When the user is satisfied with the markers, the user can hit an accept input in order to accept the marks. If the user is not happy with the marks shown in the image, the user can hit the clear button to repeat the step and identify proper marks on the probe in the first and second positions.

As shown in FIG. 10I, the calibration of the probe is repeated. The user input screen shows a probe scale icon which is used to identify the scaling on the probe, and the user again places the cross hairs over the probe to mark the start and end positions. A total of three comparisons may be required in accordance with some embodiments. Upon successful completion of setting the probe scale for a plurality of times, the scale can be calculated.

FIG. 10J shows a user input screen in which the user is informed that the scale has been calculated. The user is then prompted to hit a continue button to advance to the next screen.

FIG. 10K shows the screen shown on the display in order to confirm the scale. A radical can be shown overlaid on the ultrasound image with the scale determined with the calibration. For example, as shown in FIG. 10K, the scale can extend a distance of 70 millimeters. A calibration and the marks used can also be shown with the radical shown on the display. For example, the proximal mark and the distal mark can be shown on the display. When the distance between the proximal location and the distal location comprises about 60 millimeters, the display can show the marks at a zero location and a 60 millimeter location for example. The radical shown on the ultrasound image is presented to the user, and the user has the opportunity to accept or reset the scale. If the user chooses to reset the scale, the user is prompted to set the scale again. If the user accepts and confirms the scale, the user is allowed to advance to the next screen.

FIG. 10L shows a screen showing a calibration cut in accordance with embodiments. The calibration cut can be performed in order to verify accurate calibration of the system with an initial treatment prior to completing the treatment. The display screen shows a prompt to the user with instructions. The user is prompted to perform the calibration cut. The user can be informed to press and hold the foot switch to advance the cut and to lift the foot switch to pause or to complete the treatment. As shown in FIG. 10L, a radical is shown overlaid with the treatment probe. The treatment carrier probe comprising the nozzle can be initially aligned at a zero reference, for example, over the verumontanum as described herein. The jet can be released from the nozzle and the jet can be visualized with ultrasound as described herein or other imaging modalities, such as the endoscope for example.

FIG. 10M shows a calibration cut advancing in accordance with embodiments. FIG. 10M shows the image of the calibration cut in real time on the screen. The probe is automatically advanced and the user is instructed to lift the foot switch to pause or to complete the treatment, and a display window indicates that the probe is advancing. The probe can advance in accordance with the treatment profile programmed into the apparatus as described herein. The cut can be shown to extend approximately half way through the treatment for example with reference to FIG. 10M, although the real images shown in real time with the user can be provided in relation to the scale. The image of the organ such as the prostate being resected as shown in FIG. 10M can help the user determine that the system is accurately set to complete the treatment with tissues that are initially less sensitive to variability in treatment.

FIG. 10N shows the calibration cut near a distal end of the cut. As shown on the ultrasound image, the jet comprising the cool flame has advanced to a position of approximately 60 millimeters from the zero reference point. As shown in the real time image, the tissue is substantially resected with the target calibration cut. The screen provides the user with an input to confirm the treatment, and the user can indicate the calibration cut is complete by hitting the confirm button. The user is prompted to resume or complete the calibration cut. When the user confirms that the calibration cut is complete, the user is then provided with the next input screen.

FIG. 10O shows a determine cut depth user interface screen, in accordance with embodiments. The determine cut depth input of the user interface shown on the display allows the user to set the cut depth. As the scaling of the ultrasound image to the treatment probe has been performed previously, the pixel coordinate references of the image can be used to set additional references, such as coordinate references of the treatment profile. The user is prompted with a plurality of lines in order to indicate the cut depth. A first icon showing a vertical arrow in which a first vertical arrow is pointing up and a second vertical arrow is pointing down, the user is allowed to slide an image overlay onto the cut profile to allow the user to approximately estimate the depth of the calibration cut. The user may also be provided with another input screen that allows the user to further adjust the calibration cut measurement. Once the user has confirmed the cut depth, the user is prompted to proceed to the next user input screen. In many embodiments, the system comprises a plurality of thresholds to determine if the calibration cut depth is within appropriate machine boundaries. For example, too shallow of a cut can prompt a warning to the user and too deep of a cut can prompt a similar warning to the user.

The user interface screen may comprise several values that are available to the user. For example, a pressure and a time can be shown to the user along with a target angle. A user may also be shown with the steps of a procedure to complete the procedure, such as setup steps such as priming the pump and docking as described herein. Planning can include an angle and a scale, and the cut can comprise the calibration cut and a profile and the treatment can comprise a treatment profile for example.

FIG. 10P shows an adjustable profile in accordance with embodiments. FIG. 10P shows a treatment profile shaped to the anatomy of the user. With the ultrasound image of the prostate or other organ shown to the user, the user can select a plurality of locations to adjust the treatment. For example, as shown in FIG. 10P, the treated organ may comprise an enlarged prostate. The enlarged prostate may extend beyond a bladder neck for example or into the bladder neck as indicated with the numeral 9. The narrow restriction of the bladder neck shown at FIG. 8 can be adjusted according to the anatomy of the user and the measurement profile. And FIG. 10 can show, for example, anatomy of the prostate near the capsule and the user can adjust the cut profile accordingly. The user is allowed to adjust and confirm the contour. The user is provided with an adjust and confirm contour menu and instruction. The user is told to adjust the contour boundary and confirm to proceed. When the user has confirmed the treatment profile shown on the ultrasound image, the user hits the continue button in order to proceed.

FIG. 10Q shows a begin treatment screen. The begin treatment screen allows the user to begin the treatment. The user is instructed to hit start in order to start the treatment, and the user is instructed to press and hold the foot switch to advance the cut. Lifting this foot switch can pause the treatment. Alternatively, the user can complete the treatment. The cut profile which is fit based on the profile provided by the user is shown to the user. The target cut profile can comprise an approximation of the intended profile provided by the user. While the cut profile of the flame can be configured in many ways, in many embodiments the power of the jet can be increased so that the distance of the white flame and the cavitation as described herein can extend to a desired target distance.

Working relation to embodiments as indicated that a flow rate of the jet can provide a radial cut distance that can be substantially, linearly related to the flow rate of the fluid going into the jet. In many embodiments, the surgical site is irrigated with saline and a fluid stream comprising saline is released with high pressure to form a plurality of shedding pulses as described herein. As the distance of the white cool flame is substantially related to the cutting distance, the user can be provided with visual input as to the cut depth profile. As the cut depth profile changes, the flow rate of the fluid from the jet can be changed so as to correspond to the cut depth profile.

The cut depth profile shown in FIG. 10Q comprising steps may correspond to steps of varying flow rate. For example, the flow rate can be set with arbitrary integer values from 0 to 10 and a calibration cut performed with a flow rate of 3 on the arbitrary scale. Based on the user's anatomy and the cut profile, the system software can determine that a flow rate of 9 is appropriate for the deepest cut, and a flow rate of 8 can be performed near the bladder neck, for example. Near the proximal and distal ends of the cut, the flow rate can increase, for example, from a value of about 3 near the distal end of the cut to a value of about 8 corresponding to tissue in the bladder neck. And the flow rate can decrease, for example, to about 3. As the treatment probe comprising the jet is drawn proximally, the power of the pump can decrease corresponding to the cut profile. For example, the flow rate of the pump in arbitrary units can be decreased from about 8 to a value of about 3 near the proximal end of the cut.

FIG. 10R shows the treatment proceeding with the treatment nozzle carried on the probe being drawn proximally. The drawing of the energy source on the carrier probe proximally can reset tissue as shown in FIG. 10R and other figures. The treatment probe continues to be drawn proximally with rotation and oscillation of the probe tip until a pre-determined volume of tissue has been removed. This removal of the pre-determined volume of tissue in accordance with the cut profile can provide very accurate tissue removal. In many embodiments, delicate structures of the prostate, such as the capsule and nerves can be avoided, for example. In many embodiments, the screen that the user sees can comprise additional screens that may be helpful. For example, a treatment guide window can be provided that shows the position of the energy source on the carrier in relation to the axis of the treatment. The elongated axis of the treatment can extend, based on the program for example, from about 0 to 6 millimeters. As the energy source is drawn proximally, an indicator can be shown on the screen showing the current location of the treatment. This indicator shown on the screen can and should, in many embodiments, correspond to the indicator on the hand piece as described herein. This redundant information allows the user to verify that the instrument is performing correctly.

As described and shown herein, the user can be shown a series of steps that have been completed on the screen, for example, on the right hand side. For example, the user can be shown the current step as the treatment and the user can also be shown several preceding steps. The preceding steps may comprise setup steps, such as priming and docking as described herein. The preceding steps may comprise planning, such as setting the angle and the scale as described herein. And the previous steps may comprise defining the cut profile or parameters related to cutting, such as calibration and definition of the cut profile.

FIG. 10S shows a treatment complete screen. Upon completion of the pre-programmed treatment, the user is presented with the treatment complete screen, and the user has the option of returning to adjust the profile and perform additional resection of tissue, or to input finished and move to the next screen FIG. 10T show shows an export data screen. The user is prompted to export data. The processor may comprise instruction to export the procedure data to a non-volatile memory.

The treatment can be stored in one or more of many ways. For example, the treatment can be stored on a non-volatile memory, such as a flash drive. Alternatively or in combination, the attachment device as described herein may comprise a non-volatile memory to store the treatment. The treatment parameters stored may comprise measured sense parameters, such as the pressure of the treatment, a flow rate of the treatment, and locations of the probe during the treatment. The stored treatment parameters may also comprise a treatment table for example. And the treatment table can provide useful information. For example, when compared to the measured locations of the probe during the treatment in order to verify that the treatment has been performed in accordance with the treatment table. When the user hits the next screen, the user is prompted to move on to the next stage.

The user interface screens of FIGS. 10A to 10T are shown as an example of a series of screens in accordance with embodiments. A person of ordinary skill in the art will recognize many variations based on the teachings provided herein. For example some of the screens can be removed. Other screens can be added. Some of the screens can be combined. Some of the screens may comprise subs-screens. Further the screens may be presented in a different order.

In many embodiments, other alignment screens can be provided. For example, the user can be asked to identify an axis of the treatment probe in order to identify a reference axis of the treatment. The user could be asked to identify marks of the treatment probe, for example, in order to determine translational alignment of the treatment probe axis shown on the image with the mapped treatment shown on the screen.

Figure 11:
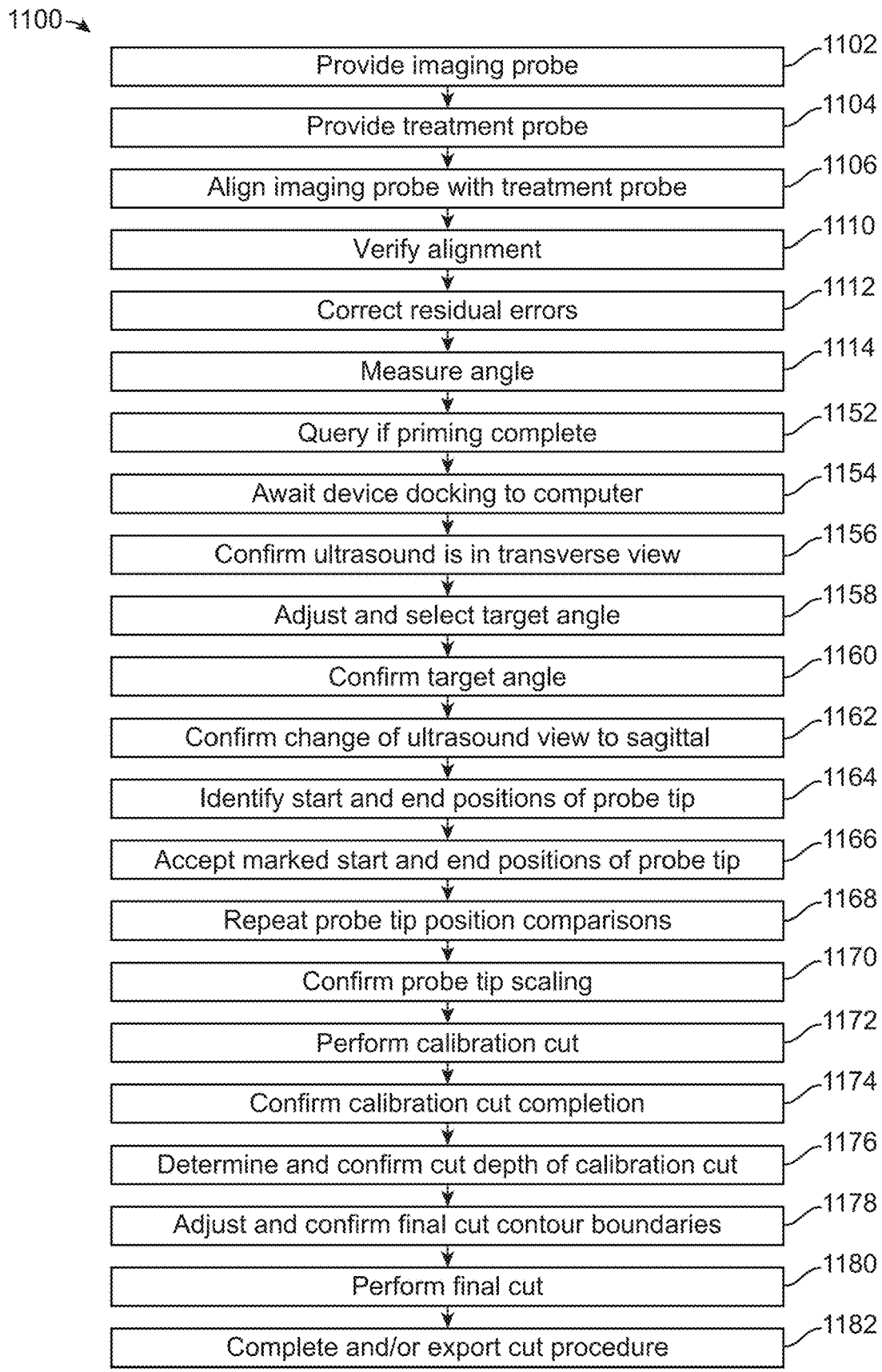
FIG. 11 shows a method a treating a patient, in accordance with some embodiments.

FIG. 11 shows a method 1100 of treating a patient in accordance with many embodiments.

With a step 1102, an imaging probe is provided having an imaging probe axis.

With a step 1104, a treatment probe is provided having a treatment probe axis.

With a step 1106, an imaging probe axis is aligned with treatment probe axis.

With a step 1110, alignment of treatment probe axis along sagittal plane of imaging probe is verified.

With a step 1112, residual errors are corrected.

With a step 1114, an angle of the treatment probe axis relative to the imaging probe with the imaging probe is measured.

With a step 1116, an image of the patient with the probe inserted therein is rotated in response to the angle.

With a step 1152, the user interface may query the user if the priming of the treatment probe has been completed.

With a step 1154, the user interface may await the docking of the treatment probe with the computer operating the user interface.

With a step 1156, the user interface may confirm with the user that the ultrasound imaging device is imaging the subject in a transverse view. Upon such confirmation, the main menu screen of the user interface may be shown.

With a step 1158, the user interface may allow the user to select the target angle of the treatment probe when performing the cutting procedure. The target angle may be varied between 0 and 180 degrees.

With a step 1160, the user interface may confirm with the user the selected cutting angle.

With a step 1162, the user interface may confirm with the user that the ultrasound imaging device is imaging the subject in a sagittal view.

With a step 1164, the user interface may facilitate the scaling or calibration of the treatment probe by asking the user to identify the start and end positions of the probe tip as the probe tip is advanced from a retracted position as shown by the ultrasound image. The start and end positions may be identified by the placement of start and end markers, respectively, on the image display portion of the user interface.

With a step 1166, the user interface may confirm with the user the marked start and end positions of the probe tip as acceptable.

With a step 1168, the user interface may repeat the identification and acceptance of start and end positions of the probe tip. In many embodiments, these steps, e.g., steps 1166 and 1168, are repeated three times to verify calibration of the probe tip.

With a step 1170, the user interface may confirm with the user the scaling or calibration of the probe tip.

With a step 1172, the probe tip may perform a calibration cut. The user interface may provide instructions on activating the probe tip to perform the calibration cut. Alternatively or in combination, the user interface may provide a menu or sub-menu to operate the treatment probe to perform the calibration cut. The display portion of the user interface may show the sagittal view of the target tissue as the calibration cut is performed. The treatment probe may be paused and un-paused during the cutting process.

With a step 1174, the user interface may confirm with the user that the calibration cut has been completed.

With a step 1176, the user interface may allow the user to determine and confirm the cut depth of the calibration cut. The user interface may provide markers for the user to drag and place at the cut location and the probe location to confirm cutting depth.

With a step 1178, the user interface may allow the user to adjust and then confirm the contour boundaries of the final cut. The user interface may provide one or more markers for the user to drag and place at desired contour boundary points to modify the contour boundary as desired.

With a step 1180, the treatment probe tip may perform the final cut. The user interface may provide instructions on activating the probe tip to perform the final cut. Alternatively or in combination, the user interface may provide a menu or sub-menu to operate the treatment probe to perform the final cut. The display portion of the user interface may show the sagittal view of the target tissue as the final cut is performed. The treatment probe may be paused and un-paused during the cutting process.

With a step 1182, the treatment may be completed and the user interface may provide an option to repeat and/or modify a treatment and/or export the history, parameters, and other information of the performed treatment to a storage medium, such as a USB drive, a local data storage device, or a cloud-based storage, for example.

The steps of method 1100 can be combined with the screens of FIGS. 10A-10T.

Although the above steps show method 1100 of operating a treatment probe in accordance with many embodiments, a person of ordinary skill in the art will recognize many variations based on the teaching described herein. The steps may be completed in a different order. Steps may be added or omitted. Some of the steps may comprise sub-steps. Many of the steps may be repeated as often as beneficial to the treatment.

For example, steps associated with the performance of a calibration cut (e.g., corresponding to the screens of FIGS. 10L-10O, and/or steps 1172-1176 of method 1100) may be omitted. If there is sufficient data of system performance to provide an accurate correlation between system power and penetration depth of the resultant cuts, the calibration steps may not be necessary, and the system may be configured to proceed directly to the treatment cut.

One or more steps of the method 1100 may be performed with circuitry as described herein, for example, one or more of a processor or a logic circuitry of the systems described herein. The circuitry may be programmed to provide one or more steps of the method 1100, and the program may comprise program instructions stored on a computer readable memory or programmed steps of the logic circuitry such as with programmable array logic or a field programmable gate array, for example FIG. 11 shows a method in accordance with embodiments. A person of ordinary skill in the art will recognize many variations and adaptations in accordance with the teachings disclosed herein. For example, steps of the method can be removed. Additional steps can be provided. Some of the steps may comprise sub-steps. Some of the steps can be repeated. The order of the steps can be changed.

The processor as described herein can be configured to perform one or more of the steps of the method of FIG. 11, and to provide one or more of the user interface screens as described herein. In many embodiments, the processor is configured to perform at least a portion of one or more of the steps in response to user input shown on a display, and the processor may comprise instructions to generate and display the user interface screens as described herein.

The processors can be further configured to record each performed step of the methods described herein with respect to FIGS. 10A-10T and 11. A separate record of use may be kept for each user or operator of the system, wherein all operator inputs provided during each step of the methods can be recorded. The operator records may be configured to be inaccessible for modification by operators (e.g., recorded as read-only files, stored in a restricted access database, backed up to a remote server, etc.). Recordation of all operator inputs and steps performed can provide enhanced operator accountability, and provide useful reference data for system improvements and/or troubleshooting.

EXPERIMENTAL

Figure 12:
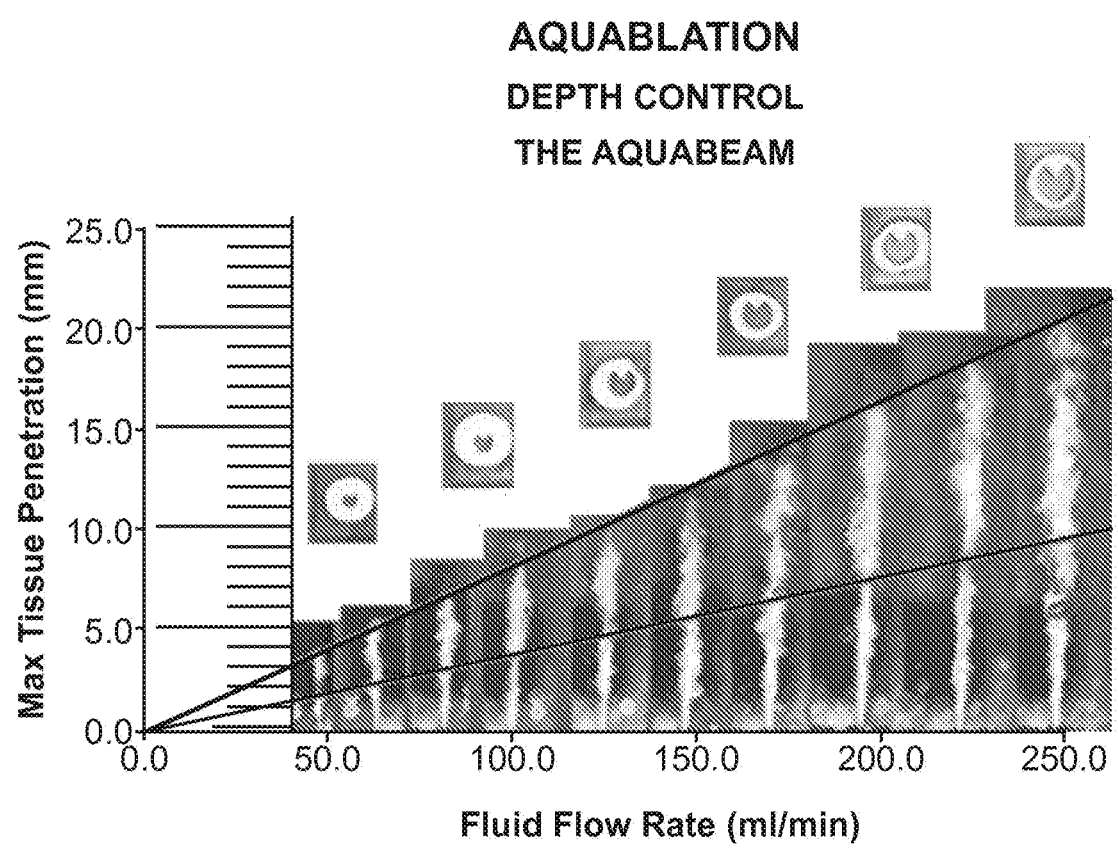
FIG. 12 shows maximum tissue penetration depth of cutting and flow rate through a nozzle in accordance with some embodiments.

FIG. 12 shows maximum tissue penetration depth of cutting and flow rate through a nozzle in accordance with embodiments. The maximum penetration depth corresponds substantially to the length of the cavitation bubbles of the jet comprising the "cold" aqua-ablation flame. The maximum tissue penetration depth of ablation corresponds directly to the flow rate and in many embodiments is linearly related to the flow rate.

The inset of FIG. 12 shows cut potato as a model of prostate BPH, in accordance with embodiments. The maximum penetration depth of potato corresponds closely to the maximum cut depth of BPH. The potato is shown cut with 10 different flow settings corresponding to rates within a range from about 50 ml/min to about 250 ml/min with a nozzle and rotating probe as described herein. The maximum penetration depth ranges from about 4 mm at 50 ml/min to about 20 mm at about 250 ml/min.

In many embodiments, the cavitation cloud growth and length comprise a function of flow rate, which is proportional to the injection pressure and vice versa, for an appropriately configured nozzle as described herein. As the pressure increases, the maximum erosive radius appears to increase linearly, which is shown as the maximum penetration depth of FIG. 12.

High velocity cavitating jets can be created by using a known high pressure pump to force the water through a nozzle in either a continuous or pulsatile flow. Despite the flow type produced by a pump, the cavitation phenomenon will be pulsatile due to the unsteady nature of vapor cavities and the cavity formation will be pulsatile even in a continuous flow jet as described herein. Without being bound to a particular theory, it is believed that both pulsatile and continuous flow waterjets will result in equivalent amounts of material erosion over a given amount of time. In many embodiments, nozzle geometry is configured to provide the flow dynamics and cavitation process as described herein. In many embodiments, the nozzle is configured to inhibit tight constriction at the waterjet exit, which can be related cavitation can occur inside the nozzle itself. In many embodiments, the sharp corners cause the water to separate from the wall and converge towards the nozzle centerline, further constricting the waterjet pathway while simultaneously reducing frictional effects caused by the nozzle wall. This results in an increased velocity along with the corresponding pressure drop and the vapor cavities formation. Vapor cavity formation will impact the overall flow dynamics as their eventual collapse results in turbulence and can affect erosion depth. A person of ordinary skill in the art can conduct experiments to determine appropriate nozzle geometry and flow rate to provide tissue removal as described herein without undue experimentation.

Aqua-Ablation

Submerged waterjet cutting as described herein has the capability to take advantage of the cavitation phenomenon to treat patients with Benign Prostatic Hyperplasia (BPH). The jet removes the excess soft tissue growth seen in BPH through the pressure pulses and microjets caused by collapsed vapor cavities. The waterjet direction can be manipulated by changing the location and orientation of the device's nozzle, either by translating the nozzle along the anterior-posterior direction or by rotating the nozzle up to 180 degrees, for example.

As vapor cavity formation and its erosive strength is a function of both injection pressure and the flow dynamics, the depth of material can be controlled by configuring the pressure as well as nozzle geometry. A greater injection pressure will result in a faster exit velocity. As discussed herein, the nozzle geometry can further increase the velocity depending on the constriction and will affect the degree of pressure drop as the waterjet exits through the Venturi effect. These factors can result in longer distances the cavitation clouds can grow to and travel before collapsing and releasing pressure pulses and microjets. The nozzle geometry and pressure settings of the aqua-ablation system have been optimized to give the user precise control and ensure the cavitating jet removes only the desired benign tissue growth.

The images provided herein show the how tissue erosion depth is a function of pressure, in accordance with embodiments. The images show the smaller cavitation cloud length and corresponding tissue resection depth for a lower injection pressure as compared with other images.

In many embodiments, aqua-ablation as described herein is capable of removing the excess tissue growth, e.g. BPH, with inhibited removal and damage of arteries and veins. The pressure pulses and microjets caused by cavitation exceed the threshold energy required to erode the soft tissue growth, and may cause minimal damage to other structures like vessels which have a much higher threshold energy. Repeated and concentrated pressure pulses and microjets may cause fatigue stress on the vasculature and result in bleeding, but the aqua-ablation system algorithm and treatment instructions as described herein are configured designed to inhibit such damage.

In many embodiments, generation of harmful emboli are inhibited. Vapor cavity formation may benefit from a minute nucleus of air already present in the blood stream, for example. Cavitation can result in the growth of the nucleus without any additional air being introduced into the system. Furthermore, the cavity will collapse once the local jet pressure exceeds the vapor pressure, such that the air pockets may reduce back to their original nucleus size. In many embodiments, embolus formation is inhibited as cavitation depends on and can be limited to micro amounts of air native to the saline solution surrounding the urethra, and the vapor cavities quickly dissipate as the jet pressure begins to rise.

Aqua-ablation as described herein takes advantage of this phenomenon. The naturally self-limiting erosive radius and unique ability to precisely ablate tissue with a low damage threshold energy while minimizing damage to nearby structures with a more dense cellular structure, such as arteries, make aqua-ablation as described herein a useful surgical tool for treating BPH. Coupled with the nearly isothermal property of cavitation as described herein, which can mitigate collateral damage and provide improved healing and an improved safety profile.

Figure 13:
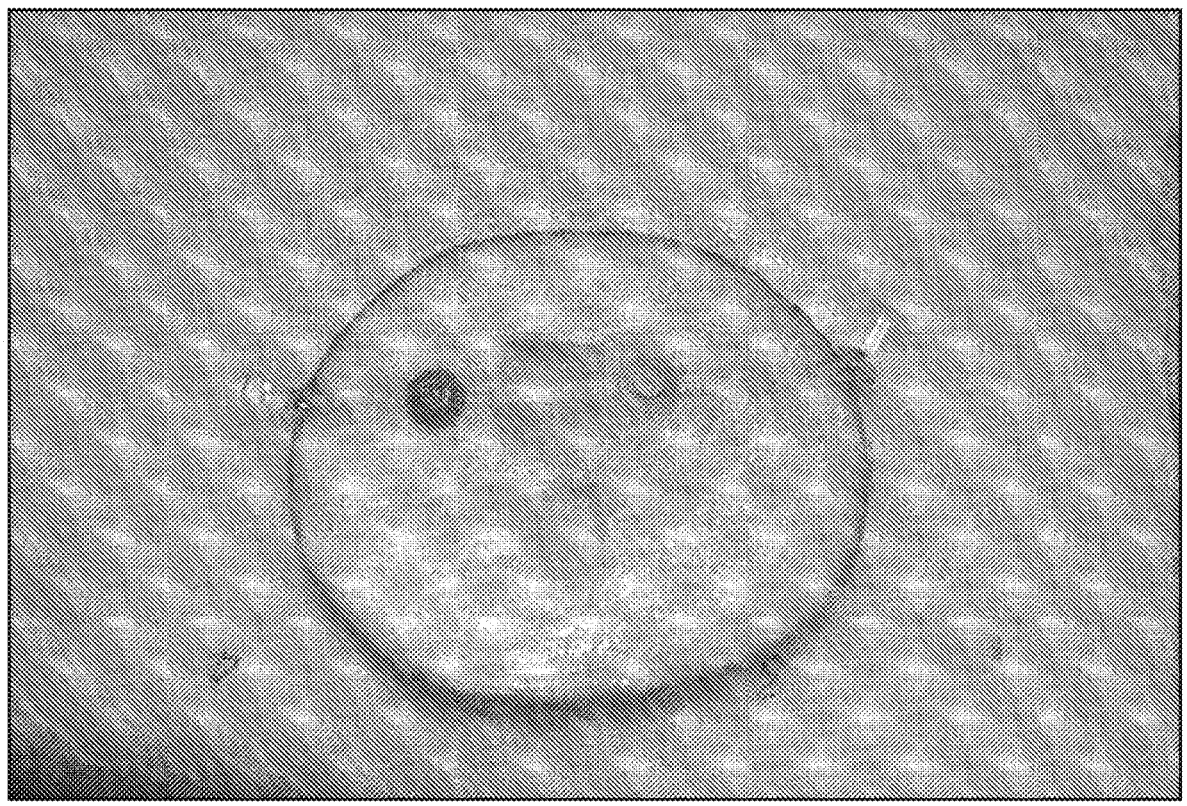
FIG. 13 shows selective removal of potato with a porcine blood vessel positioned over the incision of the potato as a model for selective removal of tissue in accordance with some embodiments.

FIG. 13 shows selective removal of potato with a porcine blood vessel positioned over the incision of the potato as a model for selective removal of tissue. The porcine blood vessel was placed on the potato prior to the incision, such that the porcine blood vessel was exposed to the water jet with cavitation in order to remove the potato. Aqua-ablation resected the soft potato tissue model, which is a close proxy for the benign tissue growth seen in BPH, without causing severe damage to the porcine vessel.

Figure 14:
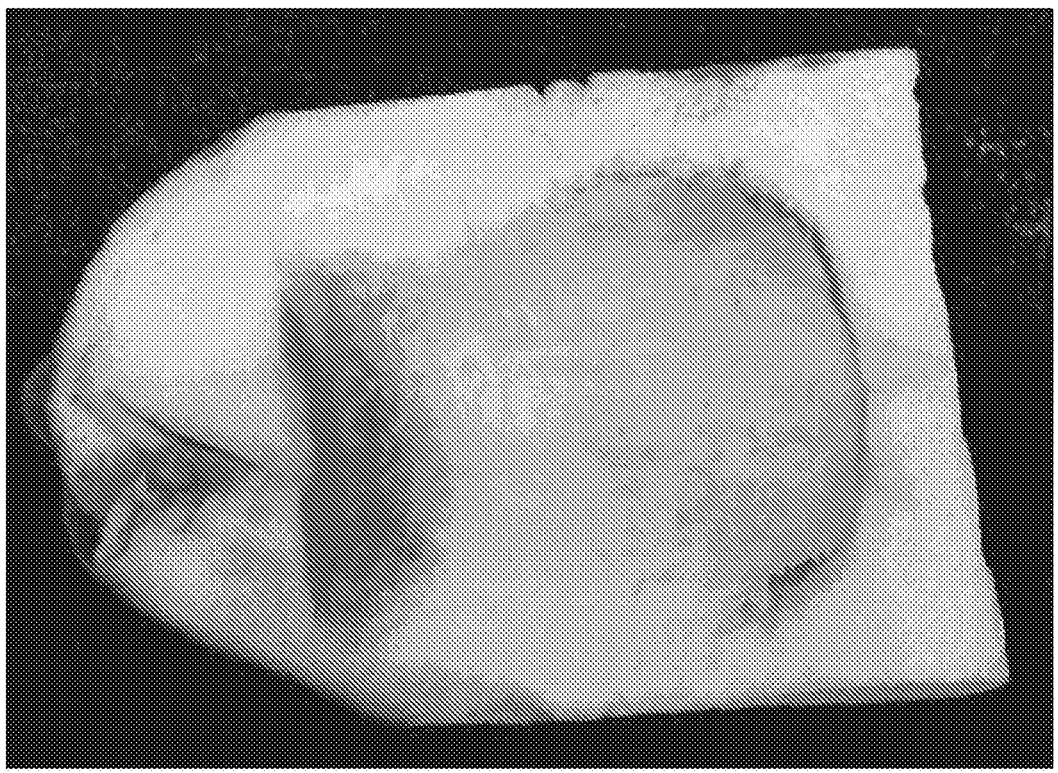
FIG. 14 shows a potato treated with a predetermined treatment profile and treatment table based on user input in accordance with some embodiments

FIG. 14 shows a potato treated with a predetermined treatment profile and treatment table based on user input.

Artificial Intelligence and Machine Learning.

The present disclosure provides several examples of patient and surgical robotics data and machine learning that can be used to train a machine learning algorithm, and any type of patient data and surgical robotics data as described herein can be used. For example, tissue ablation parameters such as the pressure and nozzle type can be used, in combination with the type of tissue to be ablated such as capsular tissue or BPH or cancerous tissue. Additional parameters include the treatment planning profiles, such as the radius, angle and longitudinal position of the cut profile. This can be combined with real time imaging from the imaging devices such as ultrasound probes, TRUS probes, endoscopes, cytoscopes, and optical images. The images may comprise images of tissue structures such as the urethra, bladder neck and verumontanum. The images may comprise a portion of the surgical instrument such as the rotating and oscillating probe as described herein. The images can be processed with image segmentation, for example, to determine the location of the tissue structure, and the surgical instrument. The artificial intelligence software instructions can be configured to automatically identify the tissue structures and surgical instruments and determine the relative locations of each. The data can be vectorized and input into the machine learning classifier, for example.

The imaged tissue structure may comprise any tissue structure as described herein, for example with reference to FIG. 5B, and may comprise the bladder, capsular vessels, the capsule, nerves, BPH, and capsular tissue for example.

The sensor data, position data, and recorded treatment positions may comprise any of the sensor data, position data, and recorded treatment positions as described herein, for example with reference to the components and sensors and elements of FIGS. 3A, and 10A to 10R. The recorded data may comprise data of the energy source, the pump, the infusion/flushing, the insufflation, the endoscope, the balloon inflation, the aspiration, the light source, the arm lock, the arm controller, the linkage, each of the angle sensors, the patient support, or the base, for example.

The treatment data may comprise set up data, for example with reference to FIGS. 8A to 8T, such as the position of the probe relative to a plurality of structures that allow a user such as a physician to adjust the endoscope independently of other components of the device. In many embodiments, the endoscope is coupled to an endoscope carriage or linkage as described herein with sensors configured to determine the position of the endoscope on the carriage during set up. The endoscope carriage can be advanced and retracted in order to move the distal end of the endoscope connected to the coupling proximally and distally, and these positions recorded during set up.

The treatment data may comprise any data and images of the planned treatment as described herein, for example with reference to FIGS. 10A to 10S. The treatment data may comprise the target angle, the planned cut tissue profile, the pressure, and other parameters as described herein The treatment data may comprise set up data related to alignment of the surgical treatment probe with the imaging probe, for example with reference to FIGS. 9A to 9B and 10A to 10S. For example, alignment of a treatment probe axis with a sagittal plane of an imaging probe as described herein can be recorded and used as input. The inclination of the elongate axis of the treatment probe relative to the elongate axis of the imaging probe as described herein can be used as input. The recorded images may comprise images from the imaging probe, which comprises a sagittal image field of view, in which the treatment probe as described herein is substantially aligned with the sagittal plane of the imaging probe when the treatment probe is within the field of view of the sagittal image, for example. The set up data may comprise priming data, docking data, angle data, scale data, calibration data, cut profile data, corresponding times of one or more of these, and planned treatment time, for example.

The planned data can be modified with the artificial intelligence or machine learning as described herein. For example, the planned and modified tissue removal profiles can be shown on the display overlaid on an image of the tissue as described herein.

Figure 15:
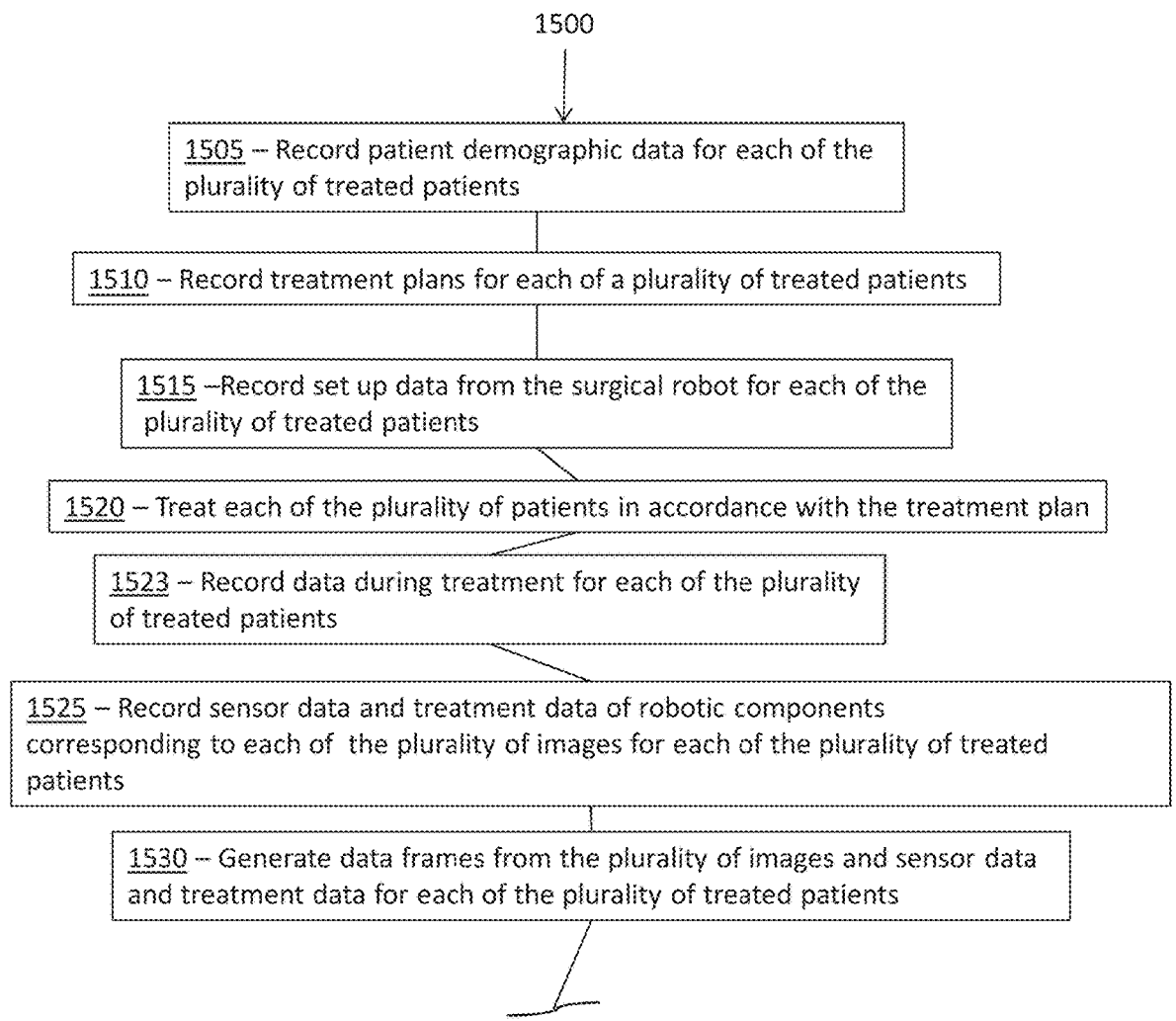
FIG. 15 shows a method of treating a patient with artificial intelligence or machine learning, in accordance with some embodiments.
Figure 15:
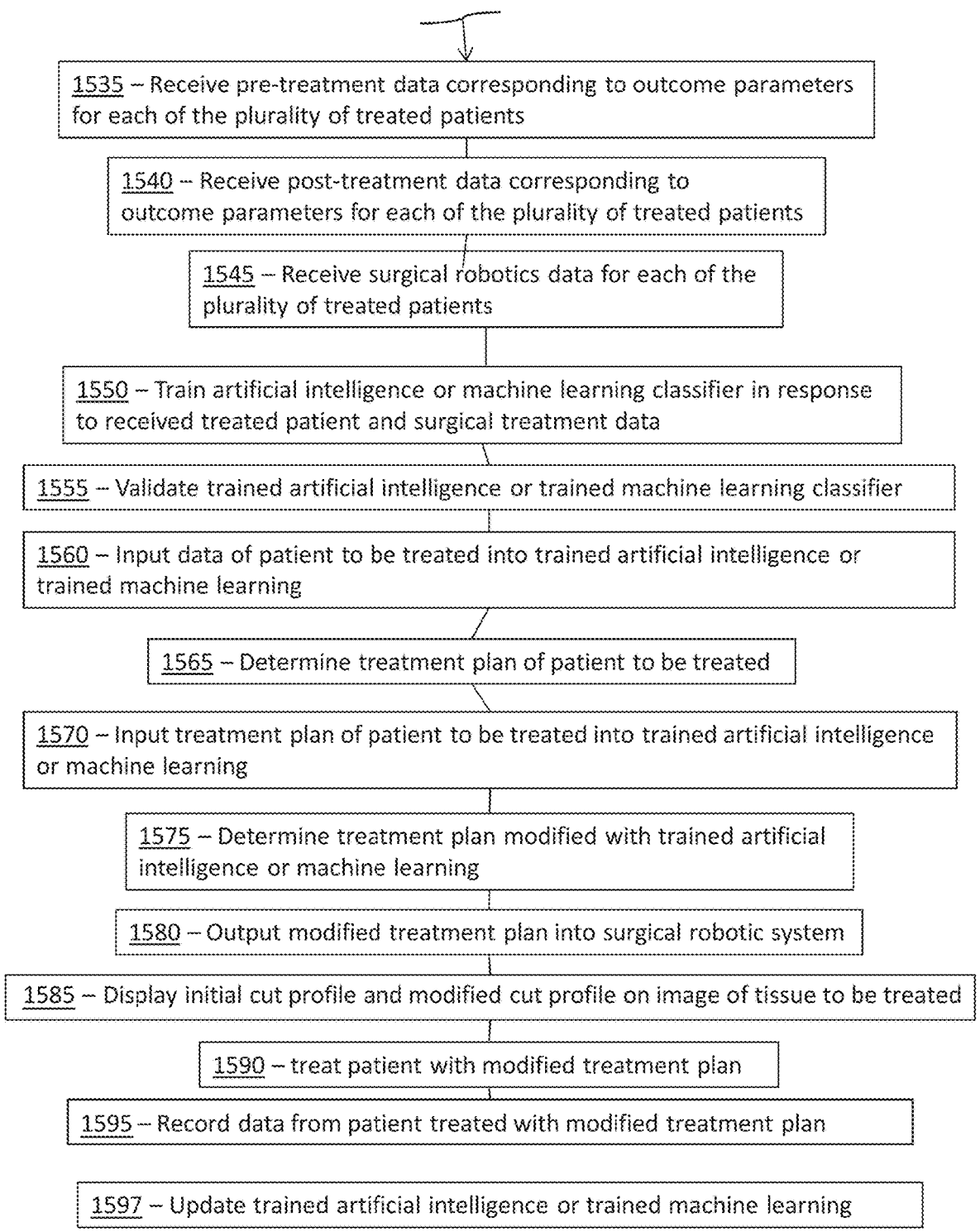

FIG. 15 shows a method 1500 of treating a patient with artificial intelligence or machine learning in accordance with some embodiments. While the method can be performed in many ways, in some embodiments, patient data are received for each of a plurality of treated patients. The data for each of the plurality of treated patients comprises one or more of patient demographic data, a cut profile of tissue to be removed, an actual profile of tissue removed, a target volume of tissue to be removed, an actual volume of tissue removed, or a ratio of an amount of tissue targeted for removal to an amount removed. Surgical robotics data is received for each of the plurality of treated patients. The surgical robotics data comprises a plurality of treatment parameters recorded during treatment, a treatment time, a set up time, an imaging time, a time a treatment probe moves, a plurality of locations and orientations of a treatment probe, a plurality of images of tissue, a plurality of images of the tissue each comprising the treatment probe, or an intensity of an energy source to remove tissue. A treatment plan of a patient to be treated is output in response to the patient data and the surgical robotics data At a step 1505 patient demographic data is recorded for each of the plurality of treated patients. The patient demographic data for each of the plurality of patients and the patient to be treated comprises one or more of patient age, weight, sex, or body mass index.

At a step 1510 treatment plans are recorded for each of a plurality of treated patients. The treatment plan may comprise any of the treatment plans as described herein.

At a step 1515 set up data is recorded from the surgical robot for each of the plurality of treated patients. The set up data may comprise any of the set up data as described herein.

At a step 1520 each of the plurality of patients is treated in accordance with the treatment plan. The patients may be treated with any one or more surgical method steps as described herein.

At a step 1523 data is recorded during treatment for each of the plurality of treated patients. The recorded data may comprise images of each of the plurality of patients. The recorded data may comprise sequential images, e.g. movies, of any of the images as described herein.

The plurality of treatment parameters recorded during treatment comprises a measured treatment time, a measured set up time, a measured imaging time, a measured time the treatment probe moves, a measured intensity of the energy source to remove tissue, a plurality of recorded positions of the treatment probe, a plurality of recorded images of the tissue during treatment, a plurality of recorded orientations of the treatment probe, a plurality of tissue images corresponding to each of the plurality of recorded positions and orientations. The plurality of treatment parameters recorded during treatment comprises a plurality of sequentially arranged data frames, each of the plurality of sequentially arranged data frames comprising an image of the tissue, an image of the treatment probe positioned in relation to the tissue being treated, a position of the treatment probe, an orientation of the treatment probe, or an energy of the treatment probe and optionally wherein each of the plurality of sequentially arranged data frames corresponds to a substantially fixed time interval between said each of the plurality of frames.

At a step 1525 sensor data and treatment data of robotic components is recorded, in which the data corresponds to each of the plurality of images for each of the plurality of treated patients. The intensity of the energy source comprises a water jet intensity, an optical beam intensity, a radio frequency energy intensity, an ionizing radiation intensity, a stereotactic radiation intensity, or an ultrasonic energy intensity.

At a step 1530 data frames are generated from the plurality of images and sensor data and treatment data for each of the plurality of treated patients. The data frames may comprise image frames corresponding to fixed intervals, such as one second between frames. Alternatively or in combination vectorized data can be generated from the image frames.

At a step 1535 pre-treatment data is received in which the pre-treatment data corresponds to outcome parameters for each of the plurality of treated patients.

At a step 1540 post-treatment data is received, in which the post-treatment data corresponds to outcome parameters for each of the plurality of treated patients.

At a step 1545 surgical robotics data is received for each of the plurality of treated patients.

At a step 1550 artificial intelligence processor instructions or a machine learning classifier is trained in response to received treated patient and surgical treatment data. The artificial intelligence processor instructions may comprise one or more of machine learning, search and mathematical optimization, artificial neural networks, statistics, probability, support vector machine learning, clustering of data groups, image classification, image segmentation. The machine learning processor instructions may comprise one or more of decision tree learning, association rule learning, artificial neural networks, deep learning, inductive logic programming, support vector machines, clustering, Bayesian networks, reinforcement learning, representation learning, similarity and metric learning, sparse dictionary learning, genetic algorithms, rule based machine learning or a learning classifier system.

At a step 1555 the trained artificial intelligence or trained machine learning classifier is validated.

At a step 1560 data of the patient to be treated is input into trained artificial intelligence or trained machine learning classifier.

At a step 1565 the treatment plan of patient to be treated is determined.

At a step 1570 the treatment plan of patient to be treated is input into trained artificial intelligence or machine learning classifier.

At a step 1575 treatment plan modified in response to the trained artificial intelligence or the machine learning classifier. The adjustment to the treatment plan of the patient to be treated may comprise an adjustment to one or more of a cut profile of tissue to be removed, an actual profile of tissue removed, a target volume of tissue to be removed, an actual volume of tissue removed, a treatment time, a set up time, an imaging time, time a treatment probe moves, an intensity of an energy source to remove tissue, or a ratio of an amount of tissue targeted for removal to an amount removed. The cut profile may comprise a plurality of locations comprising a plurality of angular coordinates about a treatment axis, a plurality of corresponding axial coordinates along the axis, and a plurality of radial distances from the axis. The adjustment to the cut profile may comprise an adjustment to the plurality of angular coordinates about the treatment axis, the plurality of corresponding axial coordinates along the axis, or the plurality of radial distances from the axis.

At a step 1580 the modified treatment plan is output and received as input into the processor of the surgical robotic system.

At a step 1585 the initial cut profile and modified cut profile are displayed on an image of tissue to be treated. An initial cut profile overlaid on an image of tissue to be resected on a display and to display an adjusted cut profile on the image of the tissue to be treated, for example.

At a step 1590 the patient is treated with the modified treatment plan.

At a step 1595 data from patient treated with modified treatment plan is recorded At a step 1597 the trained artificial intelligence or trained machine learning classifier is updated in response to the patient treated with the modified treatment plan.

One or more steps of the method 1500 may be performed with circuitry or processor instructions as described herein, for example, one or more of a processor or a logic circuitry of the systems described herein. The circuitry may be programmed to provide one or more steps of the method 1500, and the program may comprise program instructions stored on a computer readable memory or programmed steps of the logic circuitry such as with programmable array logic or a field programmable gate array, for example.

FIG. 15 shows a method in accordance with embodiments. A person of ordinary skill in the art will recognize many variations and adaptations in accordance with the teachings disclosed herein. For example, steps of the method can be removed. Additional steps can be provided. Some of the steps may comprise sub-steps. Some of the steps can be repeated. The order of the steps can be changed.

Digital Processing Device

In some embodiments, the platforms, systems, media, and methods described herein include a digital processing device, or use of the same. In further embodiments, the digital processing device includes one or more hardware central processing units (CPUs) or general purpose graphics processing units (GPGPUs) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxec®, Google TV®, Google Chromecast®, Amazon Fire®, and Samsung® HomeSync®. Those of skill in the art will also recognize that suitable video game console operating systems include, by way of non-limiting examples, Sony® PS3®, Sony® PS4®, Microsoft® Xbox 360®, Microsoft Xbox One, Nintendo® Wii®, Nintendo® Wii U®, and Ouya®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tape drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Figure 16:
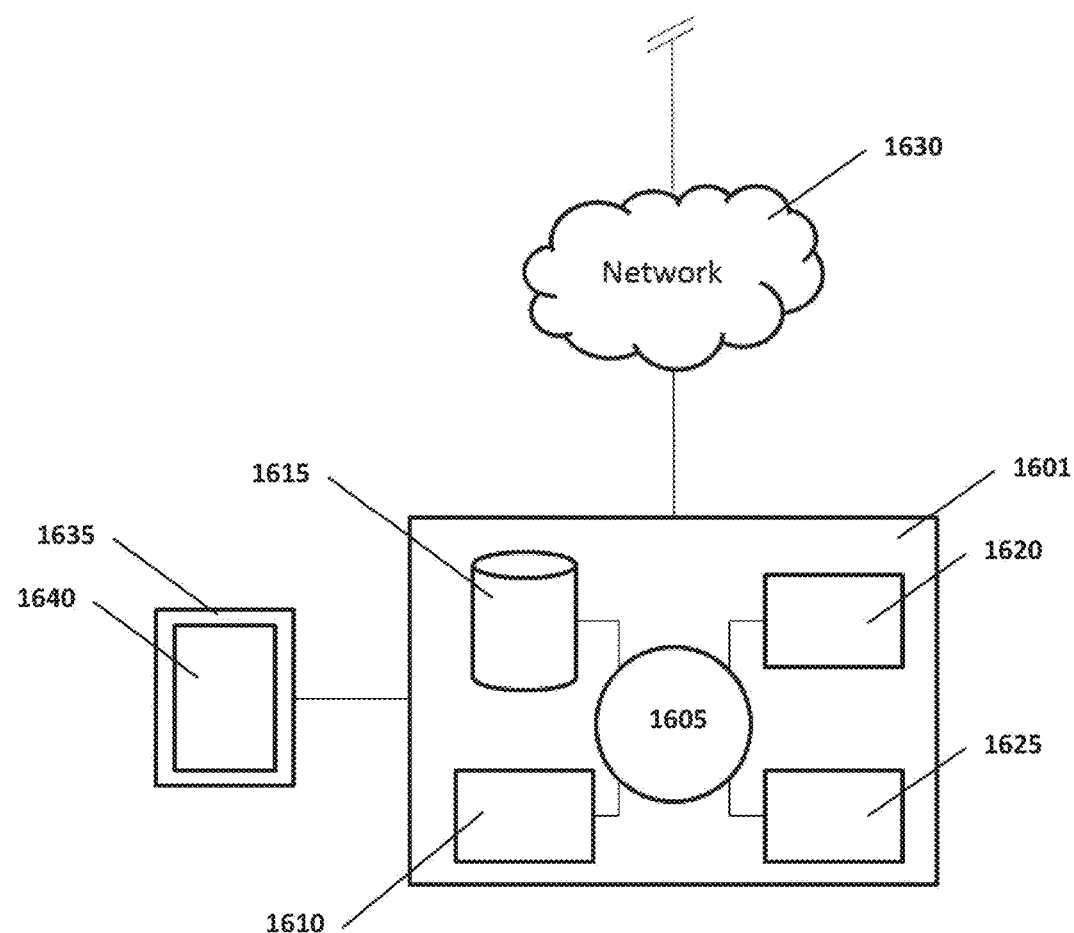
FIG. 16 shows a processor system, in accordance with some embodiments.

Referring to FIG. 16, in a particular embodiment, an exemplary digital processing device 1601 is programmed or otherwise configured to use artificial intelligence or machine learning to set up, plan or perform a surgical robotics procedure. The device 1601 can regulate various aspects of the machine learning and artificial intelligence of the present disclosure, such as, for example, determination of a cut profile in response to data 1640 of a patient to be treated and data 1635 from previously treated patients and previous surgical procedures as described herein. In this embodiment, the digital processing device 1601 includes a central processing unit (CPU, also "processor" and "computer processor" herein) 1605, which can be a single core or multi core processor, or a plurality of processors for parallel processing. The digital processing device 1601 also includes memory or memory location 1610 (e.g., random-access memory, read-only memory, flash memory), electronic storage unit 1615 (e.g., hard disk), communication interface 1620 (e.g., network adapter) for communicating with one or more other systems, and peripheral devices 1625, such as cache, other memory, data storage and/or electronic display adapters. The memory 1610, storage unit 1615, interface 1620 and peripheral devices 1625 are in communication with the CPU 1605 through a communication bus (solid lines), such as a motherboard. The storage unit 1615 can be a data storage unit (or data repository) for storing data. The digital processing device 1601 can be operatively coupled to a computer network ("network") 1630 with the aid of the communication interface 1620. The network 1630 can be the Internet, an internet and/or extranet, or an intranet and/or extranet that is in communication with the Internet. The network 1630 in some cases is a telecommunication and/or data network. The network 1630 can include one or more computer servers, which can enable distributed computing, such as cloud computing. The network 1630, in some cases with the aid of the device 1601, can implement a peer-to-peer network, which may enable devices coupled to the device 1601 to behave as a client or a server.

Continuing to refer to FIG. 16, the CPU 1605 can execute a sequence of machine-readable instructions, which can be embodied in a program or software. The instructions may be stored in a memory location, such as the memory 1610. The instructions can be directed to the CPU 1605, which can subsequently program or otherwise configure the CPU 1605 to implement methods of the present disclosure. Examples of operations performed by the CPU 1605 can include fetch, decode, execute, and write back. The CPU 1605 can be part of a circuit, such as an integrated circuit. One or more other components of the device 1601 can be included in the circuit. In some cases, the circuit is an application specific integrated circuit (ASIC) or a field programmable gate array (FPGA).

Continuing to refer to FIG. 16, the storage unit 1615 can store files, such as drivers, libraries and saved programs. The storage unit 1615 can store user data, e.g., user preferences and user programs. The digital processing device 1601 in some cases can include one or more additional data storage units that are external, such as located on a remote server that is in communication through an intranet or the Internet.

Continuing to refer to FIG. 16, the digital processing device 1601 can communicate with one or more remote computer systems through the network 1630. For instance, the device 1601 can communicate with a remote computer system of a user. Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants.

Methods as described herein can be implemented by way of machine (e.g., computer processor) executable code stored on an electronic storage location of the digital processing device 1601, such as, for example, on the memory 1610 or electronic storage unit 1615. The machine executable or machine readable code can be provided in the form of software. During use, the code can be executed by the processor 1605. In some cases, the code can be retrieved from the storage unit 1615 and stored on the memory 1610 for ready access by the processor 1605. In some situations, the electronic storage unit 1615 can be precluded, and machine-executable instructions are stored on memory 1610.

Non-Transitory Computer Readable Storage Medium

In some embodiments, the platforms, systems, media, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or extensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™ JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome WebStore, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Web Browser Plug-In

In some embodiments, the computer program includes a web browser plug-in (e.g., extension, etc.). In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB .NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of patient information and surgical information as described herein. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based.

The patient data for each patient can be stored on a database as described herein, and used as inputs to train the classifier. The patient data may comprise several fields and images for each patient, and may comprise a library of treatments. The patient data may comprise values of safety and efficacy parameters for each patient as described herein.

Exemplary Artificial Intelligence, Classifiers, Neural Networks and Associated Inputs and User Interfaces The efficacy and durability of the patient treatment can be measured in many ways. The durability of treatment may correspond to the stability of an efficacy parameter over time. For example, the durability parameter may correspond to patency of the urethra and urinary flow rate of the patient over time post-surgery. Although many metrics of patient efficacy can be used, in some embodiments, the International Prostate Symptom Score ("I-PSS") is used to determine efficacy of the procedure. The questionnaire can be provided to patients before and after the treatment, and the results used to train an algorithm as described herein. The I-PSS score has 7 questions, each with graded answers on a scale of 1 to 5. These graded answers can be used an input to train the algorithm. The questions include, Incomplete Emptying, Frequency, Intermittency, Urgency, Weak Stream, Straining and Nocturia. "Incomplete Emptying" refers to a sensation of the bladder not being empty. "Frequency" refers to how often the subject has to urinate less than every two hours. "Intermittency" refers to how often the subject has stopped urinating and started again several times during a urination. "Urgency" refers to how often the subject has found it difficult to postpone urination. "Weak Stream" refers to how often the subject has had a weak urinary stream. "Straining" refers to how often the subject has had to strain to start urination. Nocturia refers to how many times the subject got up at night to urinate. The total of these values can be added to determine an overall score with 1-7: mild, 8-19: moderate, and 20-35: severe. The total can be used as input to the algorithm such as a classifier or neural network as described herein.

Other tests can be used, such as the American Urological ("AUA") Symptom index.

Another input to the algorithm can be patient results related to sexual function following prostate surgery, such as the International Index of Erectile Function abbreviated questionnaire ("IIEF-5"). The IIEF-5 has five questions related to sexual function, and the answers range from a value of 1 to 5, with 1 being very low and 5 being very high. The questions are directed to confidence, firmness, stability, and subject satisfaction with erections. The IIEF-5 scores can be combined to provide a total score. The individual values and/or the total scores can be used as input into the algorithm as described herein in order to train one or more of a classifier or a neural network.

Additional parameters that may be used include one or more of return to work time, uroflow data, catheterization time, catheter tension, Foley catheter tension, or catheter tensioning device method. In urological procedures such as prostate surgery it can be helpful to place a catheter such as a Foley catheter in the patient to maintain urological flow. Work in relation to the present disclosure suggests that tensioning the catheter placed in the urethra of the patient can decrease bleeding and maintain placement of the catheter. As catheterization can be somewhat uncomfortable for the patient, it can be helpful to decrease catheterization time, while maintaining patency of the urethra and decreasing bleeding. As many types of catheter tensioning can be used, it can be helpful to receive as input the type of catheter tensioning used. Examples of catheter tensioning include weights, springs, tape and other approaches that can be used to tension the catheter.

The input patient data may comprise one or more biomechanical parameters from the tissue of the patient, such as one or more of tissue strain, tissue elasticity, tissue tensile strength, tissue elongation, tissue modulus, or tissue homogeneity. These measurement can be made for each patient and used an input. For example and ultrasound probe can be used to measure these parameters and these parameters may comprise components of an ultrasound probe. For example the ultrasound probe can be configured to measure the tissue with one or more of low-frequency vibration, step, freehand, physiological displacement, radiation force (e.g. displacement, impulse, shear wave and acoustic emission) or pulse-echo or Doppler ultrasound. The ultrasound probe to measure tissue parameters may comprise a component of the TRUS probe as described herein.

Alternatively or in combination, these biomechanical tissue parameters can be determined and provided as input such physical palpation with measuring tools. In some embodiments, these values can be determined with a look up table. For example, the demographic parameters such as the age of the patient and tissue biomechanical parameters for each patient can be input into the classifier, and used to generate a look up table for tissue parameters in response to patient demographic data.

The image of the patient used as input may comprise one or more of tissue margin identification, tissue plane identification, tissue differentiation detection, fluoroscopy, CT scan imaging, magnetic resonance imaging, radioactivity detection, or radiopaque imaging, for example. In some embodiments the image comprises a fluorescence image of tissue of the patient. The fluorescence image may comprise image of the tissue marked with a fluorescent antibody configured to bind to cancerous tissue in order to identify cancerous tissue in the image, for example.

The input patient data may comprise an identification of cancerous tissue in one or more images of the patient.

In some embodiments, the processor is configured with instructions for the user to select one or more parameters used to determine one or more of a safety parameter value, an efficacy parameter value or a proposed tissue resection profile. This can be helpful to accommodate specific preferences based on user experience, for example if a physician believes that particular demographic parameter or another parameter is not helpful in planning a treatment or predicting outcomes.

In some embodiments, the processor is configured with instructions for a user to plan a surgery on a first display remote from a surgery system, store parameters for the planned surgery, and provide parameters to a processor operatively coupled to a display of a surgical system. This can be helpful for a user to preplan a surgery. For example, surgeon can pre-plan a patient treatment and at location remote from the surgical size, and have the parameters of the planned treatment loaded onto the surgical system to decrease preparation time at the surgical site.

In some embodiments, the user is provided with guidance in response to the patient data. The user can select visualization or preplanning reports considering differing approaches of differing recommended treatment plans based on individual or grouped artificial intelligence "AI" approaches. The user can take into consideration differing algorithms' strengths in predicting outcomes, such as risk, recovery, sustainability, length of procedure, specific patient characteristics, or physician characteristics.

In some embodiments, the user select data to use with a selected algorithm, for example. This can allow the user to consider outcome likelihood odds and risks for differing scenarios and with a desired outcome versus risk, for example.

Although reference is made to a rotating and translating treatment probe, the methods, apparatus and artificial intelligence programs disclosed herein are well suited for combination with many types of robotic surgical procedures. The robotic system may comprise a processor operatively coupled to a linkage such as a robotic arm. For example, the surgical system may comprise a robotic arm, such as a 5 to 7 degree of freedom robotic arm with an end effector. The robotic arm may comprise joint states that can be recorded, along with images of the surgery. The end effector may comprise the energy source as described herein to remove tissue to a tissue resection profile. The end effector can be present in images that are stored as described herein. One or more of the images, linkage states, resection profiles or patient data such as demographic data can be recorded in a database comprising a library of patient procedures as described herein, and this database used to train the classifier as described herein. The trained classifier can receive as input data from an individual patient and the output of the classifier used to determine the treatment parameters. The treatment for an individual patient can be planned with a user interface as described herein.

The treatment parameters and safety and efficacy data can be used to train one or more of a classifier or neural network as described herein, for example with reference to FIG. 15. Once trained the classifier and/or neural network can be used to provide information on a display to assist a robotics system user such as a surgeon to determine an appropriate tissue resection or cut profile.

The information shown on the display may comprise a safety parameter and an efficacy parameter, for example. The system user can adjust the tissue resection profile to provide an appropriate balance between the safety parameter and the efficacy parameter. The safety parameter may comprise a likelihood of erectile dysfunction, for example a predicted IIE-5 score at a time post-surgery, for example one year post surgery. The efficacy parameter may comprise a likelihood of retreatment at a time in the future, for example 5 years in the future. The efficacy parameter may comprise a predicted I-PSS score at a time in the future, for example a predicted I-PSS score five years in the future.

Displaying these profiles with associated parameters can be helpful for the physician to plan the treatment in accordance with a treatment plan that is acceptable to the patient. For example, some patients may be averse to retreatment and be willing to accept some sexual dysfunction. Alternatively, some patients can be averse to sexual dysfunction and more willing to receive retreatment.

In some embodiments, as part of the treatment planning the physician can present the target safety and efficacy parameters to the patient on a display of a computer, and the patient can digitally sign and accept the parameters. For example, the display can show a predicted I-PSS score at 5 years to the patient and a predicted IIEF-5 score to the user at one year, and the user can digitally sign and accept these parameters. The target parameters can be shown on a display with the image of the prostate and the digital signature of the patient. This data can be stored on a processor as described herein, and provided to the physician on the display as part of the treatment planning process as described herein. This data can also be stored as part of the records for the patient, for example as electronic medical records ("EMR").

Figure 17A:
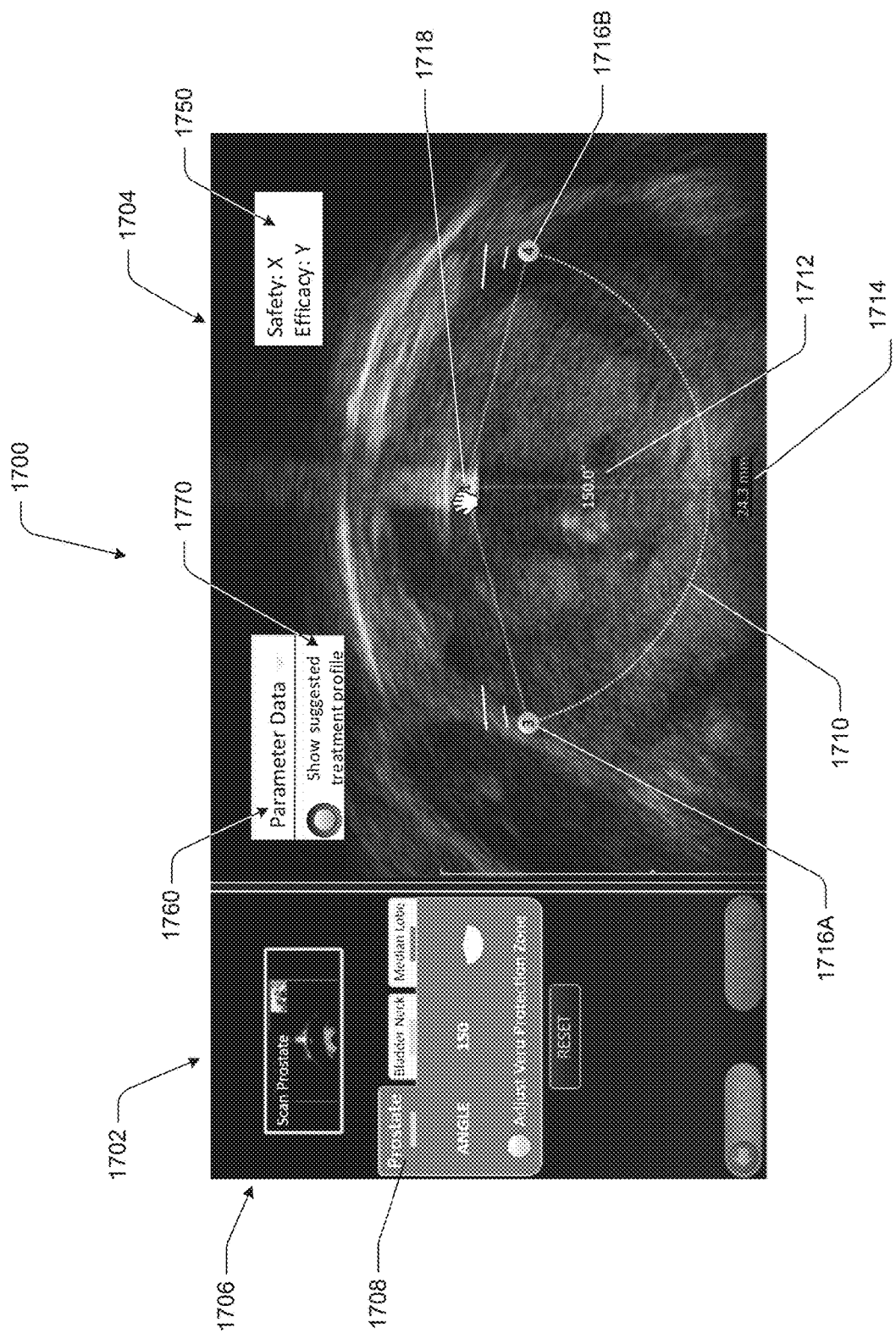
FIGS. 17A to 17C show user interface screens of an apparatus, in accordance with some embodiments.

With reference to FIG. 17A, a sample user interface 1700 is illustrated that is usable with the devices and methods described herein. The user interface 1700 may comprise two main areas, such as the instruction area 1702 and the control area 1704. Of course, the illustrated user interface 1700 layout is exemplary, and any suitable layout or arrangement of information and control inputs can be utilized without departing from the scope hereof.

In the instruction area 1702, a user of the system may be reminded and/or prompted as to the procedural step next in a series of steps. For example, as illustrated, the instruction area 1702 indicates that an imaging device, such as a TRUS probe, is scanning the prostate in a scan window 1706. The scan window 1706 may display an area of the anatomy that is being scanned, or that should be scanned for the current procedural step, as will be described hereinafter. The provided view is a transverse view of the prostate.

An anatomy selection window 1708 provides a user the ability to choose the portion of anatomy for which to establish a working profile. As illustrated, the user has selected "Prostate" as the portion of anatomy to set a working profile for.

A safety and efficacy parameter window 1750 shows values of one or more safety or efficacy parameters as described herein for the subject in response to the resection profiles and ultrasound images. For example, the efficacy values X may comprise one or more of a target efficacy value or an efficacy value determined in response to the resection profile and structures of the image. For example, the window 1750 may display a target efficacy value determined for the patient in consultation with the patient, and a predicted efficacy value generated in response to the resection profile and the image. The window 1750 may display a target safety value determined for the patient in consultation with the patient, and a predicted safety value generated in response to the resection profile and the image. These values can be determined in real time in response to the resection profiles shown on the display and structure of the ultrasound images. The safety parameter may comprise a value X, and the efficacy parameter may comprise a value Y. As the user adjust the resection profiles, the values of X and Y shown on the display can change. The processor can be configured with instructions to generate an initial resection profile in response to the ultrasound images and the targeted safety and efficacy values that may have been previously agreed upon by the patient and physician. This initial resection profile can be provided on the display and adjusted by the user.

As the portion of anatomy is selected, an image may be displayed that corresponds to the selected portion of anatomy. For example, a real-time image may be displayed that is captured by an in situ imaging system. In some instances, a TRUS probe will be placed in proximity to a patient's prostate and will provide real-time imaging of the area. In the control area 1704 of the user interface 1700, a user will be able to specify an area to be treated. The system is programmed with defaults that aid a user in selecting an appropriate treatment plan. For example, where the user has selected the prostate, as illustrated, the control window 1704 initially displays an arc 1710 having an angle 1712 and a radius 1714. The arc 1710 defines a tissue resection profile, in which an area of treatment within the arc 1710 is treated and the area outside the arc 1710 is excluded from treatment. Arc control handles 1716a, 1716b are provided and allow a user to control each leg of the arc 1710 to adjust the angle 1712. A display shows the selected angle 1712 and can be used to precisely adjust the angle 1712 to define an appropriate treatment area. The resection profile shown on the display initially may comprise a profile determined in response to desired safety and efficacy values. A vertex 1718 of the arc 1710 shows the placement of a treatment probe. In some cases, a treatment probe provides for energy delivery to treat the affected area. In some cases, the treatment probe is rotated about its longitudinal axis in order to direct the treatment energy as described herein. Accordingly, the treatment area will resemble an arc 1710 having a radius 1714 commensurate with the energy intensity. As the arc control handles 1716A,B are adjusted to define the tissue resection profile and the treatment area, the settings are stored for later use during the procedure and to control the degrees of rotation of the treatment probe during the resection with energy delivery.

The user interface 1700 may comprise a user input 1760 for the user to select parameters of the model used to determine the values of the one or more of the safety and efficacy parameters as disclosed herein. This selection of the parameters can allow the user to pick parameters that may be more helpful than others, and to remove parameters that may be less helpful than others for a particular patient. For example, if a user believes that a parameter such as age is less helpful for predicting outcomes, the user can deselect that parameter as input to the classifier model used to predict the outcome. Alternatively, if the user believes that age is a helpful parameter, the user can select age as a parameter to be used as input to the classifier model.

The user interface 1700 may comprise a user input 1770 for the user to select data to be shown on the display. The data shown on the display may comprise visualization data for example. In some embodiments, the user can select whether to show a suggested treatment profile on the display overlaid with the planned treatment profile the patient after user adjustment. This can be helpful to the user to determine how far the planned treatment profile for the patient deviates from the profile suggested by the algorithm. The user can select additional types of visualization data to be shown on the display. For example, the user can select a planned trajectory of the energy source for the treatment.

Figure 17B:
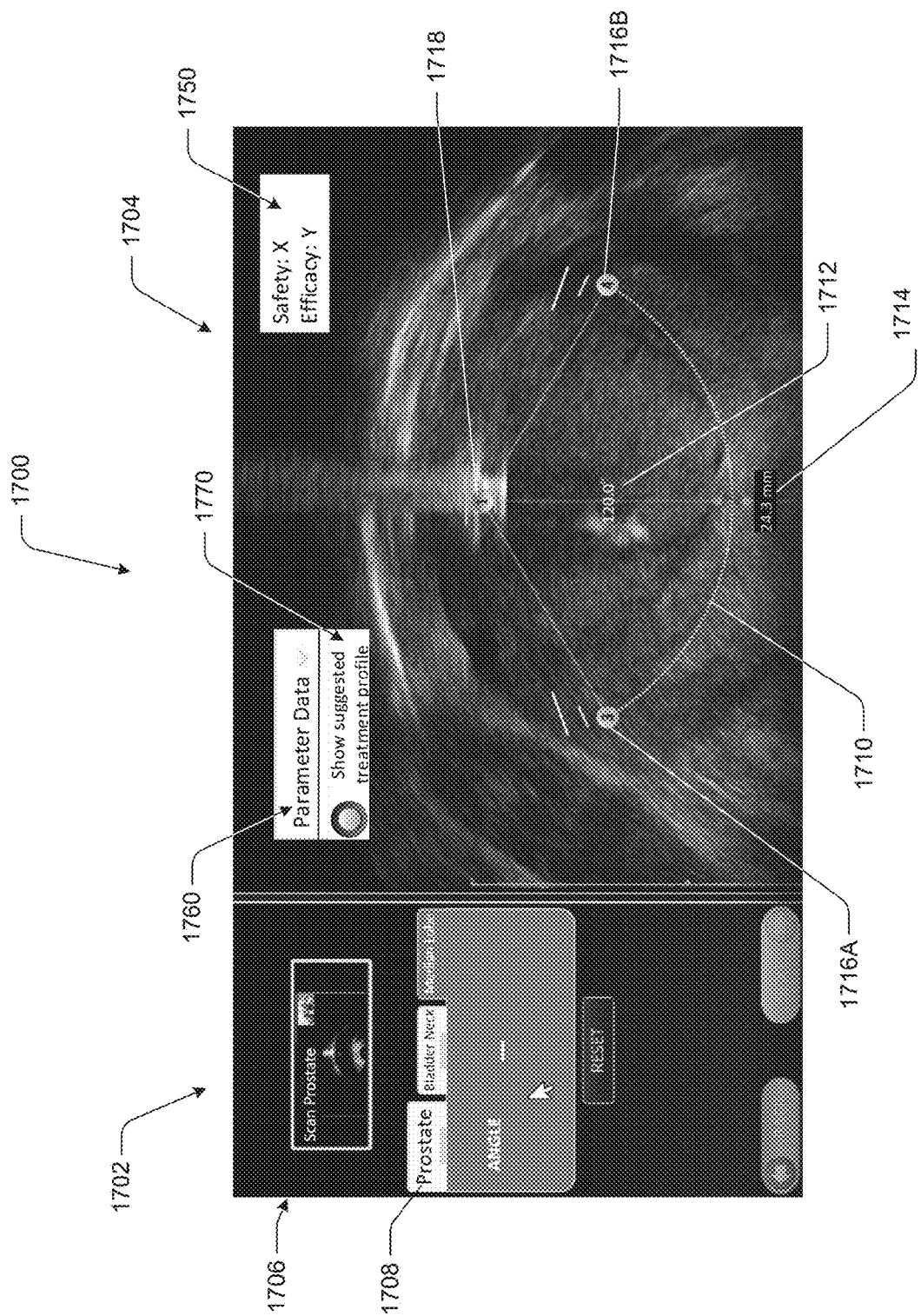

With reference to FIG. 17B, the user interface 1700 shows that a different portion of anatomy has been selected in the anatomy selection window 1708 within the instruction area 1702. As shown, the Median Lobe has been selected as the treatment area within the anatomy selection window 1708 and the control area 1704 has been updated to show imaging associated with the Median Lobe anatomy. As before, the control area 1704 overlays a display of the resection profile defined with the treatment boundary comprising an arc 1710. The arc 1710 is customizable by a user to manipulate the arc control handles 1716 A, B and in some instances, by specifying the radius 1714. The arc 1710 defines resection profile and the area of treatment and can provide different resection profiles and treatment areas for different anatomical areas. For instance, as shown, the instruction area 1702 allows a user to select between the Prostate, the Bladder Neck, and the Median Lobe within the anatomy selection window 1708. The window 1750 can display the safety parameter X and the efficacy parameter Y, and these values can change in real time as the user adjusts the resection profile.

Similar to the Prostate setup, when the Median Lobe anatomy is selected, an image of the treatment area is shown within the control area 1704, such as by a TRUS probe properly located to image the anatomical feature of interest, and a user is able to specify a treatment area for this anatomical feature. The plurality of resection profiles and corresponding treatment areas established by the user can be fed into a computer which may save the treatment plans for execution by a surgeon, whether human or robotic.

Figure 17C:
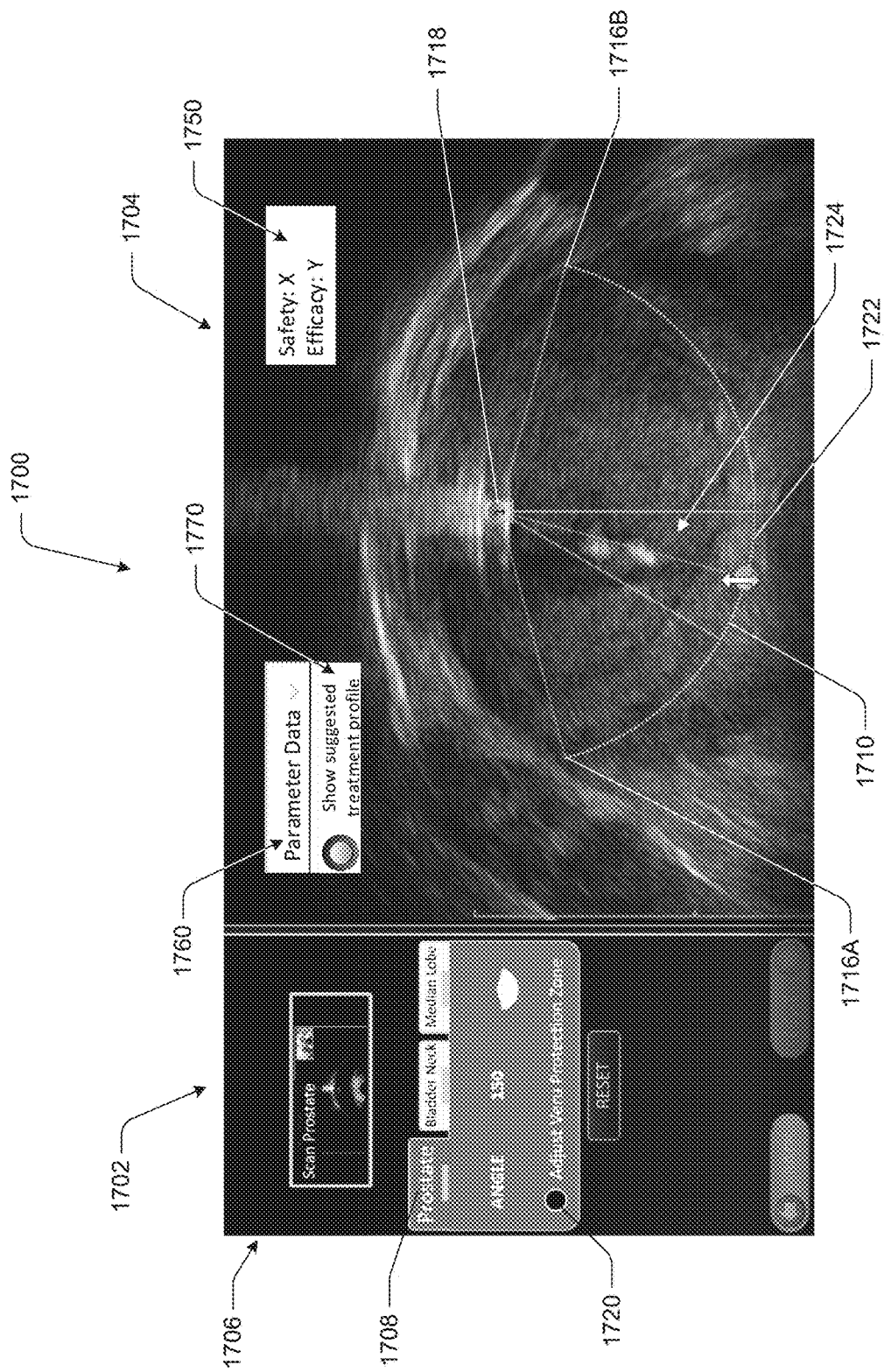

With reference to FIG. 17C, the user interface 1700 is shown. As illustrated, in the anatomy selection widow 1708, the Prostate is selected and the control area 1704 shows real-time imaging data of the selected anatomy. The anatomy selection window 1708 further has been updated to select the option labeled "Adjust Veru Protection Zone" 1720. This refers to a treatment plan designed to protect the verumontanum ("veru") from aggressive resection. The veru protection zone can be configured in many ways, and may comprise a butterfly cut profile, for example. Although reference is made to a veru protection zone, the protection zone may comprise one or more protection zones to protect a delicate tissue structures such as a tumor or retina of an eye, for example.

As shown, once the "Adjust Very Protection Zone" 1720 radio button has been selected, a new overlay appears over the control area 1704 and defines a veru arc 1722, which is a portion of the arc 1710. The veru arc 1722 shares the vertex 1718 and may share the radius 1714 length with the arc 1710.

The veru arc 1722 comprises a treatment profile that defines an area that is associated with a veru protection zone 1724. In prostate surgery, there can be a risk/reward tradeoff between the efficacy of the procedure and male sexual function as described herein. The aggressiveness of the prostate resection treatment is related to proximity to the verumontanum. If tissue is resected closer to the veru, the effectiveness of the prostate treatment for benign prostatic hyperplasia can increase. However, the risk of male sexual dysfunction may also increase. The window 1750 providing safety and efficacy parameters can be helpful to the user to adjust the treatment profile for the patient to correspond to the targeted safety and efficacy metrics.

The verumontanum is an anatomical landmark near the entrance of the ejaculatory ducts into the urethra, and may also be referred to as the seminal colliculus. The structure of the verumontanum consists of striated muscle fibers of the external sphincter, interwoven with smooth muscle tissue from the urethral wall. Some of the described embodiments herein allow for a targeted specific treatment of the prostatic tissue in close proximity to the verumontanum. According to the embodiments illustrated in FIGS. 17A-17C, a user can specify the resection profile a treatment plan for various areas of the prostate. For example, a treatment plan is created that includes unique treatments for the prostate, bladder neck, and median lobe, and a unique plan for the verumontanum area.

The user can adjust the resection profiles in response to the safety and efficacy parameters shown on the display.

Although FIGS. 17A to 17C refer to a display coupled to a surgical system, in some embodiments similar images and user input can be used for remote treatment planning and preplanning at a remote location away from the surgical instrument, such as in another room or building. The processor can be configured with instructions for the user to plan the treatment, these parameters can be stored and loaded onto the processor of the surgical system. For example, a diagnostic image of the patient can be generated prior to treatment, for example in an imaging lab. The image can be shown on a display to the user on a mobile device, and the can adjust the treatment profiles and other aspects of the treatment. Once accepted, the treatment parameters, e.g. the resection profile, can be loaded onto the surgical instrument.

Figure 18:
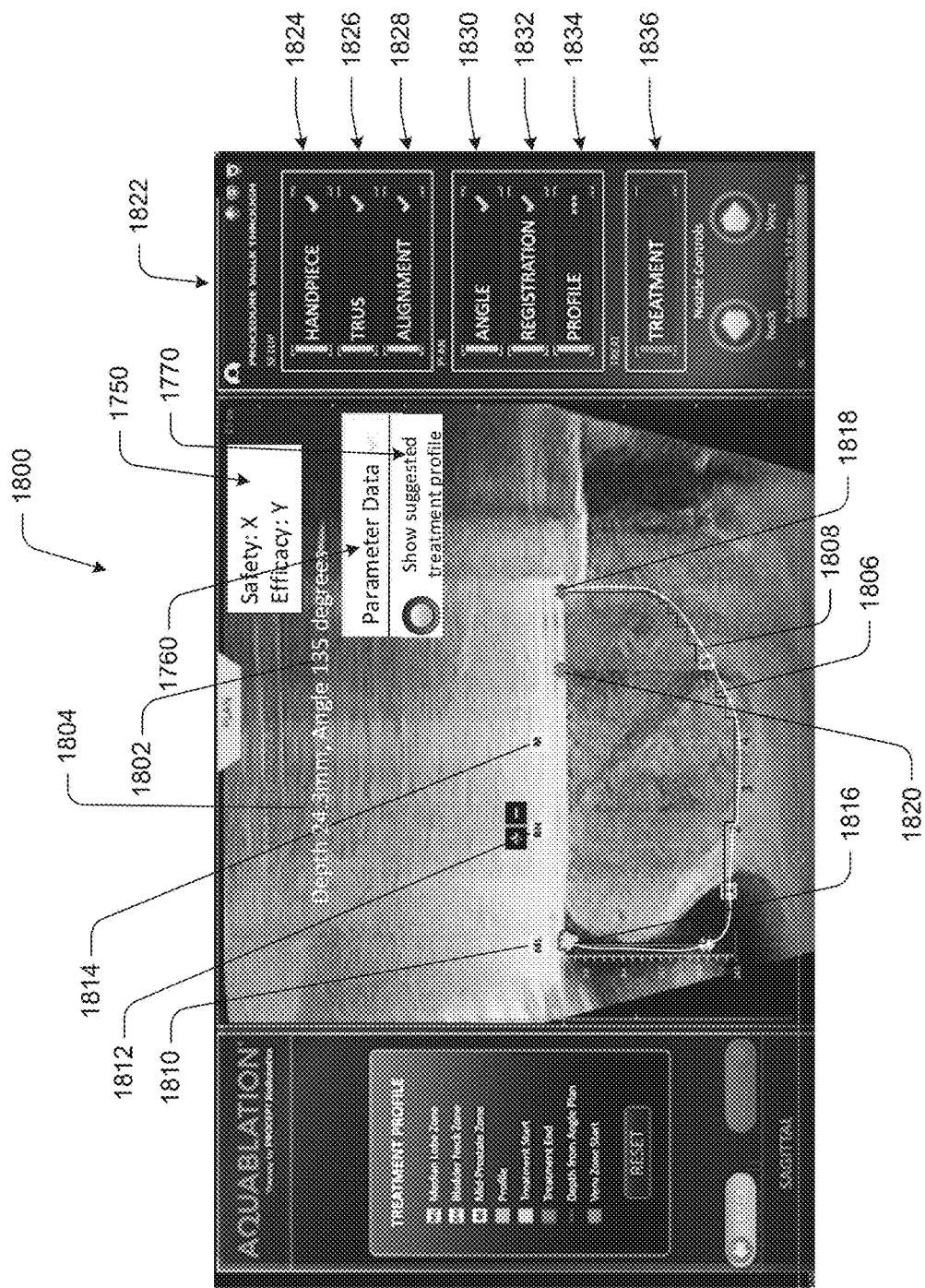
FIG. 18 shows a user interface screen of an apparatus, in accordance with some embodiments.

With reference to FIG. 18, a sagittal user interface 1800 showing a sagittal view of the treatment area with the anatomically distal organs to the left of the figure. The user interface may comprise transverse interface 1700 and sagittal interface 1800 to plan the treatment profile in three dimensions for 3D volumetric tissue removal. This screen displays information from the treatment plan already entered, such as the angle of rotation of the treatment probe 1802, which is 135 degrees in this example, and the depth of resection 1804, which is 24.3 mm in the illustrated example.

The user interface 1800 allows further refining of the treatment plan by manipulating a treatment profile 1806. The treatment profile 1806 generally follows an anatomical curve fit 1808 of the area of interest. In some cases, the system can detect the anatomical features, such as through one or more algorithms executed on ultrasound imaging, such as image analysis, feature recognition, edge detection, or some other algorithm or combinations of algorithms to detect a recommended boundary of the anatomical features and/or a recommended boundary of the resection profile and treatment area.

The system can present an overlay of information over the ultrasound imaging information, which may include anatomical portions of organs, instructions, resection profiles, as well as other information. In the illustrated user interface 1800, the overlay identifies areas corresponding to the median lobe zone 1810, the Bladder Neck Zone 1812, and the Mid-Prostate Zone 1814. Each of these identified zones may have a different treatment plan associated therewith. For example, the median lobe zone 1810 may have a designated angle of resection, depth of resection, and translational distance of tissue resection, which may be different than the treatment plan specific to the bladder neck zone 1812, which may also be different than the treatment plan for the mid-prostate zone 1814.

The processor can be configured to not only recognize the various anatomical zones, but to also store information regarding the recommended and chosen treatment plan for each of the zones. For example, information from prior surgeries may be stored in a database that corresponds with one or more treatment plans for individual organs, or portions of individual organs. This information from prior surgeries can be used to train a classifier or a neural network as described herein. The trained classifier or neural network can generate an appropriate recommended treatment plan comprising a plurality of tissue resection profiles. This recommended resection profile can be generated and presented on a display along with the predicted safety value X and predicted safety value Y in window 1750. As a treatment plan comprising a plurality of cut profiles is modified by the user, the processor may receive the modified treatment plan, cut profile and ultrasound images and the trained classifier or neural network can be used to generate updated safety and efficacy parameters shown on display 1750. The trained classifier or neural network may also receive as input patient information, such as age, height, weight, symptoms, and other information as described herein in determining values of the safety and efficacy parameters and in generating a treatment plan.

The user interface 1800 may include controls to allow a user to adjust the treatment plan. For example, a treatment start control 1816, a treatment end control 1818, and a veru zone start control 1820. Any of these controls may be manipulated by a user in order to modify the resection profile of the treatment plan. For example, a user may move one or more of the controls to modify the resection profile, such as by modifying the depth of resection, the location of the resection start control 1816, or the location of the veru start zone control 1820. Changes made by the user at the user interface 1800 are stored in memory of an associated computing system for later execution during the procedure. In some cases, the procedure is performed by robotic equipment executing the procedure according to the resection boundary limits.

The user interface 1800 further has informational and/or educational components, such as a procedure walk through area 1822 that provides guidance to a user of the system. For example, as illustrated, the procedure walk through area 1822 includes a list of procedural setup steps for a user to perform, such as locating the handpiece 1824, locating the TRUS probe 1826, and aligning the handpiece and TRUS probe 1826.

The procedure walk through area further includes creation and/or modification of the treatment plan, such as by providing the user and opportunity to enter and/or modify the angle of resection 1830, the registration of the treatment probe 1832, and a cutting profile 1834. As shown in FIG. 18, the setup steps have been completed for a procedure, as indicated by the checkmarks next to the handpiece 1824, TRUS 1826, alignment 1828, angle 1830, and registration 1832. At the current stage in the illustrated example, a user still needs to complete the profile 1834 adjustment. Upon completion of the setup steps and plan steps in the user interface 1800, a user can indicate that the procedure is ready to begin by selecting the Treatment icon 1836, at which point, the system may autonomously begin the procedure according to the treatment plan.

In some cases, the treatment plan is stored in a database along with other treatment plans and may include data regarding the patient and the treatment plan, such a patient age, weight, height, symptoms, length of symptoms, diagnosis, past treatment history, treatment efficacy, medication history, and the like. Past treatment plans may include data such as angle and resection profile for a plurality of historical treatments for multiple patients and be stored as historical treatment plan data.

The historical treatment plan data may be analyzed by one or more suitable algorithms as described herein, such as one or more of artificial intelligence algorithms, supervised machine learning, unsupervised machine learning, neural networks, or convolutional neural networks. In some cases, the historical treatment plan data is analyzed by one or more machine learning algorithms and may be used to train a classifier. For example, a neural network may analyze the historical treatment data to provide a recommended treatment plan for one or more current patients. For example, based upon the historical treatment data, a neural network may be used to build, train, and deploy a machine learning model including preparing and labeling historical treatment data, choose an algorithm, train the model, validate the model, tune and optimize the model, deploy the model, make predictions about future treatment plans, and provide treatment plans for current or future patients.

In some instances, a convolutional neural network may be implemented to analyze visual data, such as ultrasonic imaging from a TRUS probe, and provide feedback to feed into a machine learning model. The visual data analysis may include identifying anatomical features, along with relevant position, size, shape, health, and other information.

The processor as described herein can be configured with instructions to provide the user interface, images and windows as described herein, for example with reference to FIGS. 17A to 18.

With reference to FIGS. 19A to 19D, a resection procedure 1900 is illustrated. As shown with FIG. 19A, a treatment probe 1902 is inserted through the urethra to the distal portion of the treatment area. When used in the illustrated example of FIGS. 19A-19D, the terms "proximal" and "distal" are from the perspective of the treatment probe. Thus, the distal end of the treatment probe is the portion of the probe inserted farthest into the patient.

The treatment probe 1902 includes an aspiration port 1904 and an energy treatment probe 1906. A treatment area 1908 is shown by a dotted line for clarity of the series of FIGS. 19A-19D. As shown in the illustration, the resection procedure has begun and the energy treatment probe 1906 has been moved proximally from one end of the treatment area and ablated tissue from the distal portion of the treatment area 1908. The aspiration port actively aspirates fluid and ablated tissue during the procedure, and may comprise a component of a fluid management systems. The energy treatment probe is rotated through the angle and translated along the length specified in the user interface 1800 as described above. Further, the depth of resection is also controlled based upon the user input into the user interface 1800.

Figure 19A:
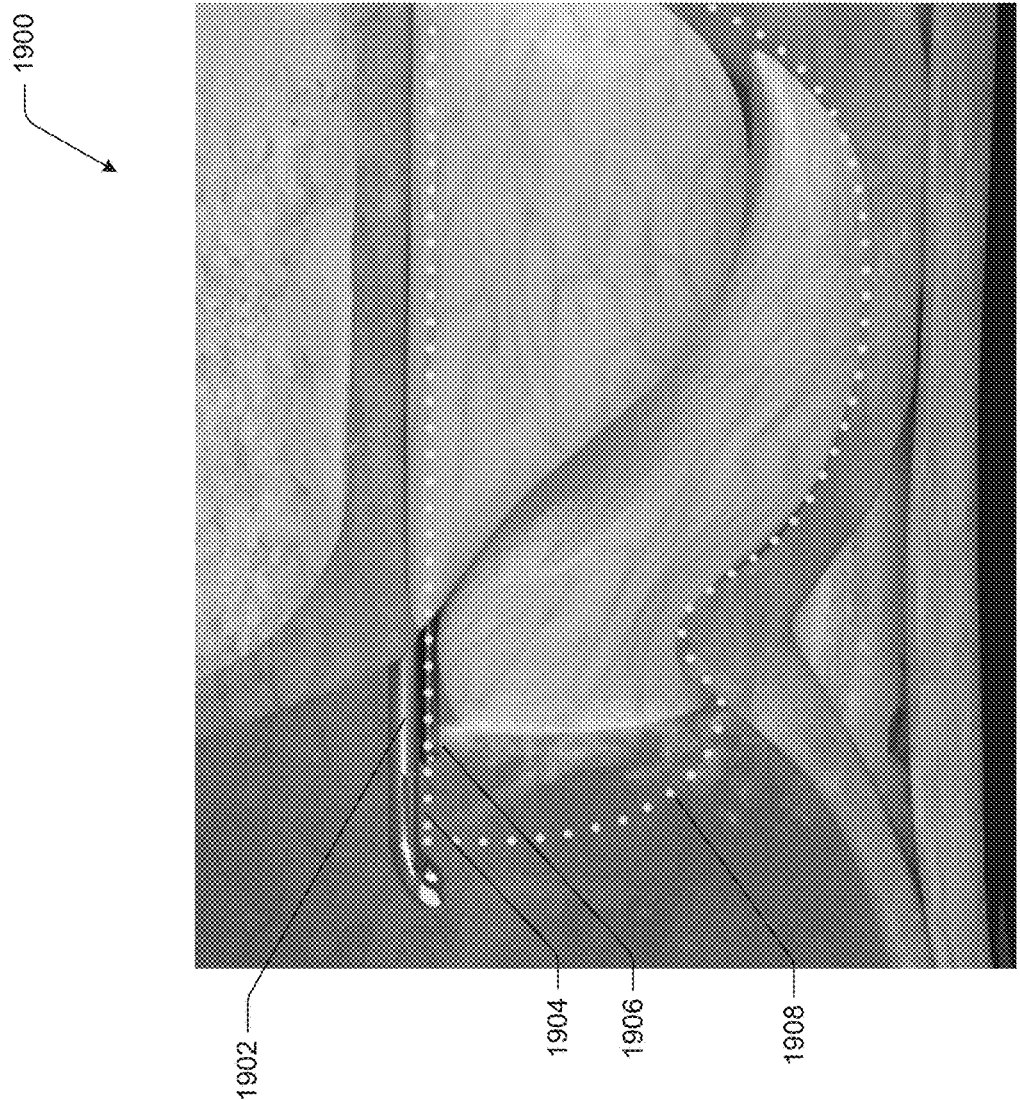
FIGS. 19A to 19D show a representation of treatment of a patient, according to some embodiments.
Figure 19B:
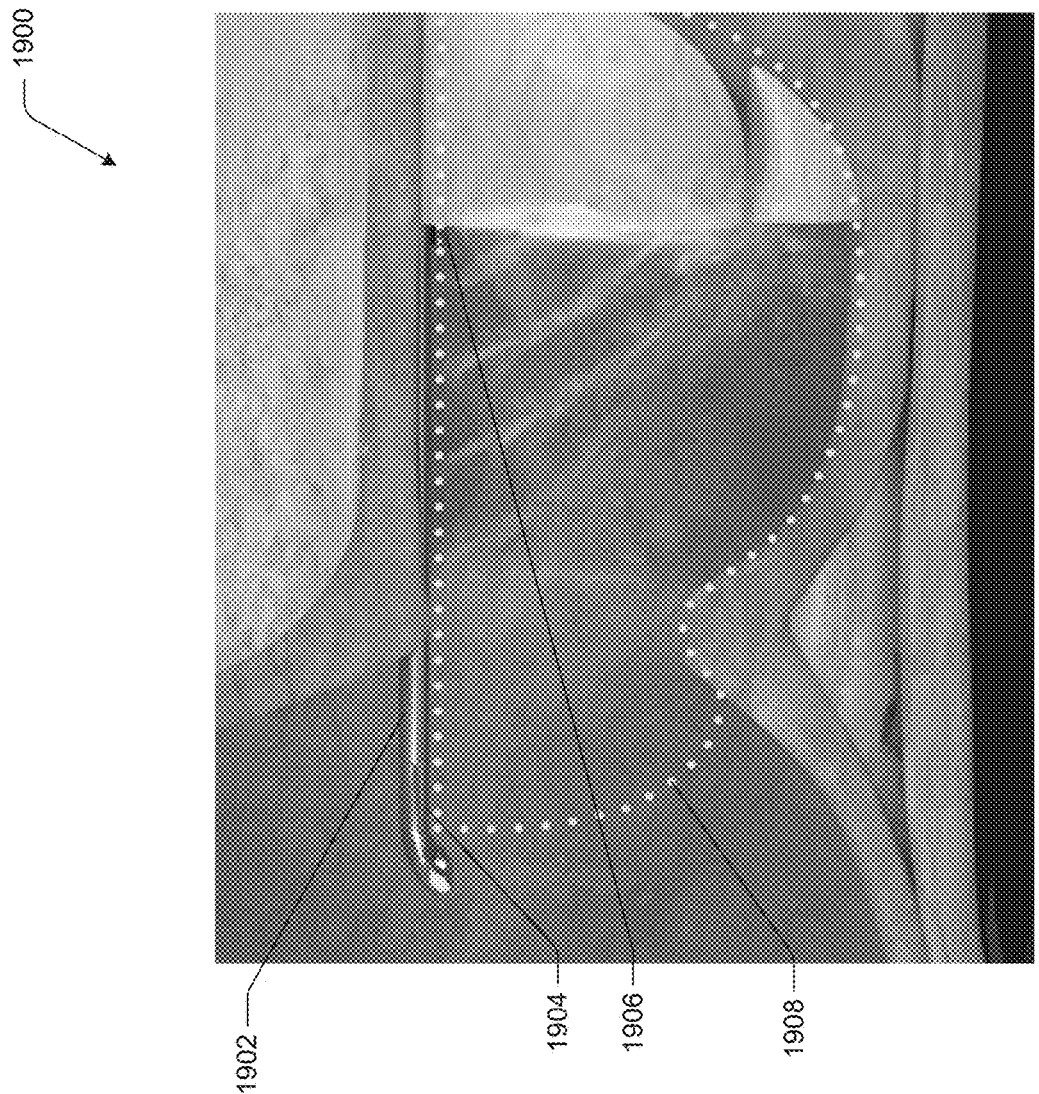

With reference to FIG. 19B, it can be seen that the energy treatment probe 1906 has moved further proximally to ablate a greater volume of tissue. During the translational movement of the energy treatment probe 1906, the intensity of the resection energy has been varied according to the treatment plan so that the resection closely follows the treatment area boundary 1908.

Figure 19C:
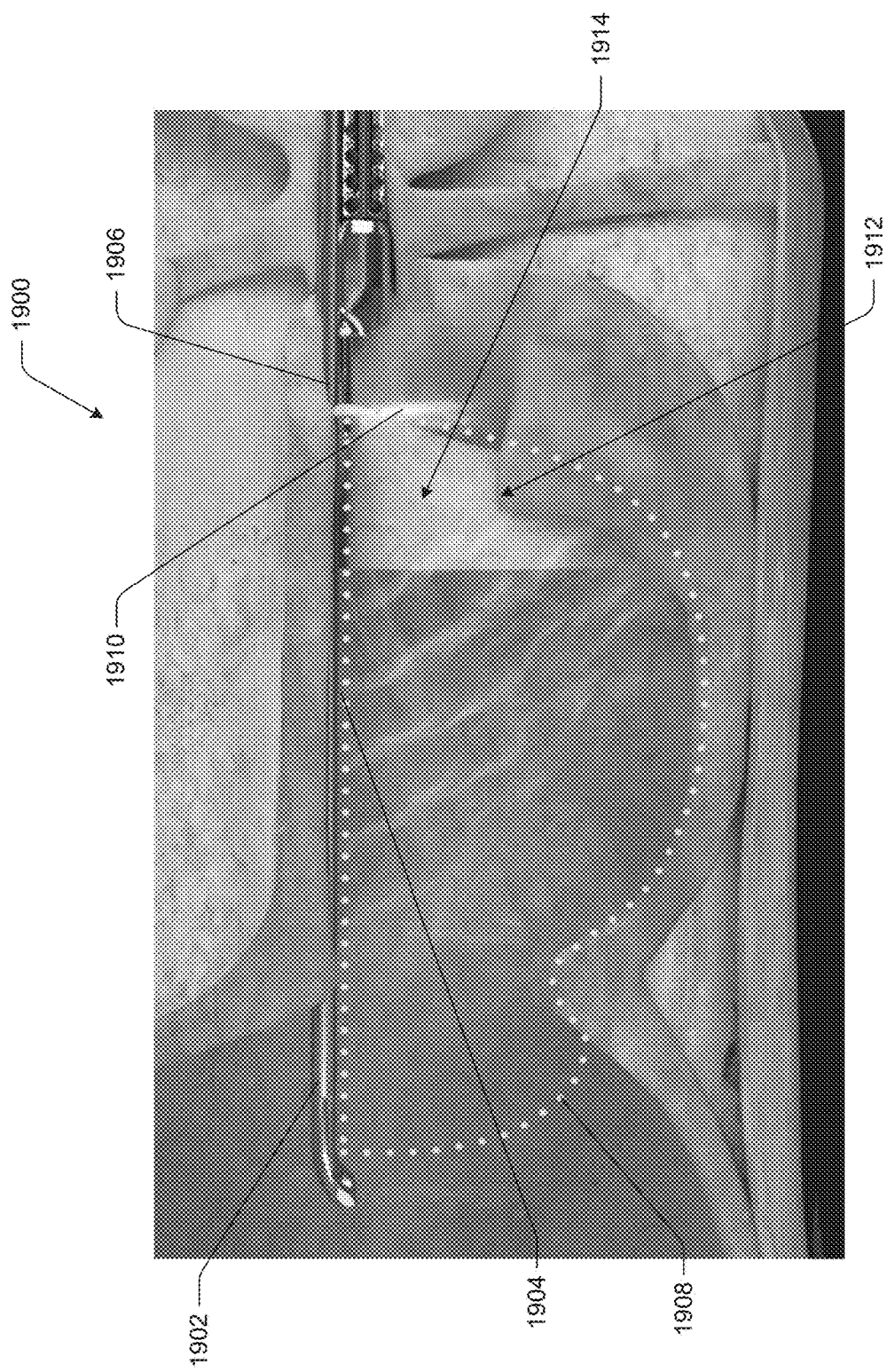

Referring now to FIG. 19C, the energy treatment probe 1906 has moved to a position roughly aligning with the proximal edge of the treatment area 1908. The resection energy 1910 can be seen coming from the energy treatment probe 1906 at a relatively low intensity. In the illustrated treatment plan, it can be seen that tissue has been retained within the area of the verumontanum 1912. When a user establishes the veru protection zone 1724, as illustrated in FIG. 17C, the treatment plan is created that protects this zone from aggressive resection. In some instances, the tissue within the veru protection zone 1724 is ablated separately from the surrounding tissue. As shown, the tissue next to the verumontanum 1912 has been ablated, but the tissue directly above the verumontanum has not been ablated. Resecting according to the treatment plan in which the veru protection zone 1724 has been established will leave a wedge of tissue 1914 above the verumontanum 1912. The wedge of tissue 1914 may be ablated according to a unique treatment plan that may gently ablate the tissue, such as by utilizing a relatively low energy intensity from the energy treatment probe 1906 utilizing multiple sweeps in a translational and rotational direction in order to ablate the wedge of tissue 1914.

In some cases, the tissue to one side of the wedge of tissue 1914 is ablated first, and then the tissue to the other side of the wedge of tissue 1914 is ablated, and finally, the wedge of tissue 1914 is ablated to protect the verumontanum from aggressive resection.

Figure 19D:
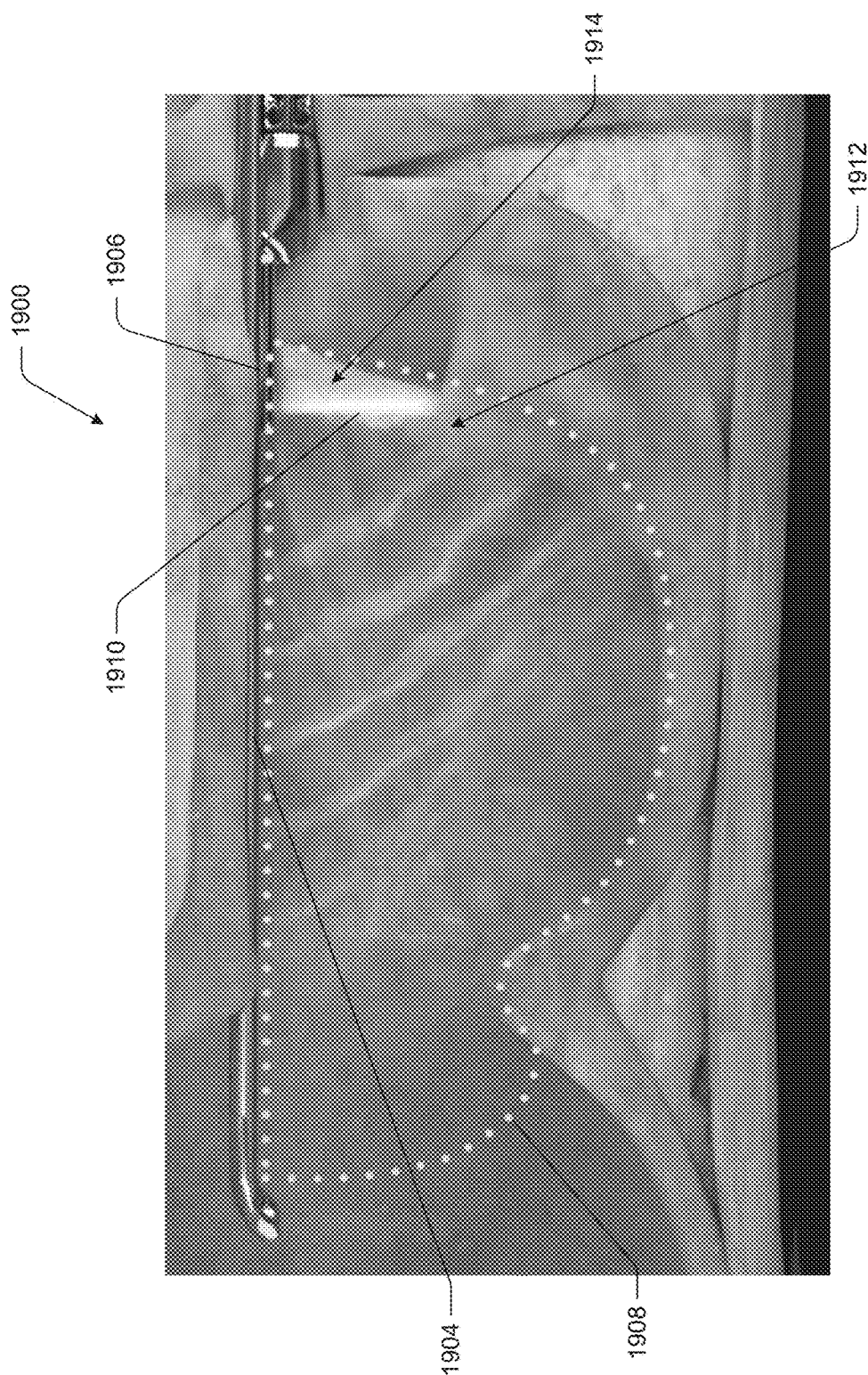

With reference to FIG. 19D, the energy treatment probe 1906 has continued to move proximally and is resecting the wedge of tissue 1914 above the verumontanum. While the illustration shows that the wedge of tissue 1914 is being ablated in a single translational pass of the energy treatment probe 1906, it should be understood that the energy treatment probe 1906 may make a plurality of translational passes and/or a plurality of rotational sweeps in order to adequately remove the wedge of tissue 1914. The aspiration port 1904 may include multiple ports or channels through which material is removed from the treatment location.

Figure 20:
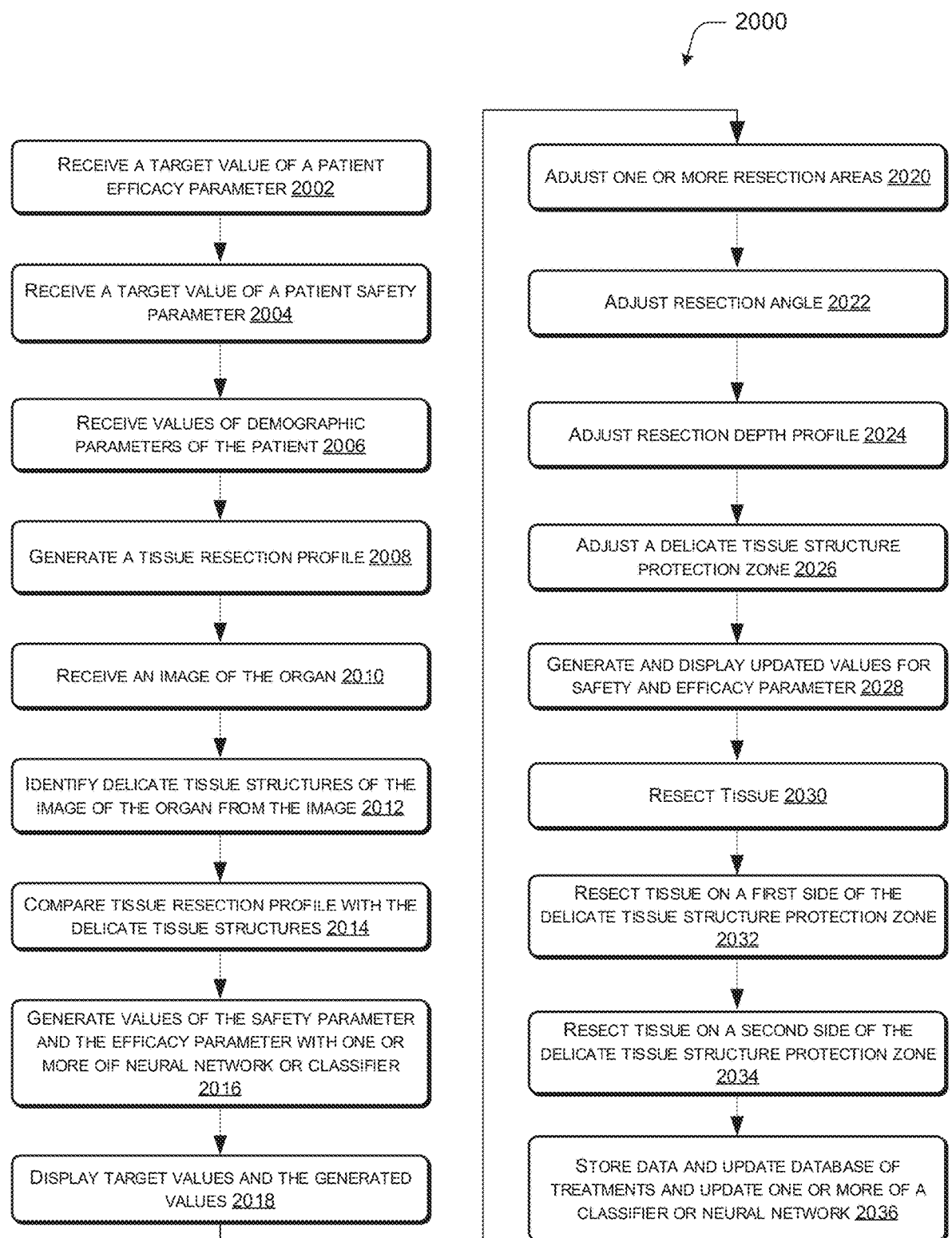
FIG. 20 shows a method of treating a patient, in accordance with some embodiments.

FIG. 20 shows a method 2000 of resecting tissue.

At a step 2002, a target value of a patient efficacy parameter is received.

At a step 2004, a target value of a patient safety parameter is received

At a step 2006, values of demographic parameters of the patient are received

At a step 2008, a tissue resection profile is generated. This process may be automated or may be created or modified by user input, such as by modifying the cut profile of the treatment area. In some embodiments the resection profile is generated in response to the values of the target safety and efficacy parameters.

At a step 2010, an image of the organ to be resected is received.

At a step 2012, delicate tissue structures of the image of the organ are identified from the image. This may be based upon image feature recognition by applying a convolutional neural network employing any of a number of suitable image analysis algorithms, such as, edge detection, feature recognition, segmentation, 3D model reconstruction, among others.

At a step 2014, a tissue resection profile is compared with the delicate tissue structures of the image.

At a step 2016, values of the safety parameter and the efficacy parameter are generated with one or more of neural network or classifier trained on a database as described herein. These values may be generated with a trained a convolutional neural network application that classifies image features, such as with ultrasonic imaging.

At a step 2018, the target values and the generated values are displayed.

At step 2020, one or more of the resection areas is adjusted. This may include determining different treatment areas for a single organ, such as determining separate treatment areas for the bladder neck, median lobe, and mid-prostate, for example. Determining different treatment zones facilitates creating separate treatment plans for each of the treatment zones.

At step 2022, a resection angle is adjusted. The treatment angle has been described herein, for example above in reference to FIGS. 17A-17C, and may be based upon an overlay of real-time imaging of an area to be treated.

At step 2024, the resection profile, is adjusted. This may be done by the user in response to the target values and generated values shown on the display. The resection profile may be adjusted for each of one or more treatment areas.

At step 2026, a delicate tissue structure protection zone is adjusted. The delicate tissue structure protection zone may comprise a veru protection zone, for example.

At a step 2028, updated values for safety and efficacy parameters are generated and displayed to the user.

At a step 2030, tissue is resected, for example away from the protection zone. The energy treatment probe may translate along its longitudinal axis and may additionally rotate about its longitudinal axis. The energy treatment probe may move across the tissue within the treatment area in a single pass to ablate the tissue according to the treatment plan, or may make multiple passes in order to ablate the tissue according to the treatment plan.

At step 2032, tissue near the delicate tissue structures is resected on a first side of the protection zone.

At step 2034, tissue on a second side of the delicate tissue structure protection zone is resected, which can leave a wedge of unresected tissue above the delicate tissue structures, such as the delicate tissue structures of the verumontanum. The tissue may be resected by an energy treatment probe providing ablative energy to the tissue.

At a step 2036, treatment data are stored and the database of treatment is updated as described herein. One or more of classifier or neural network may also be updated as described herein.

Although FIG. 20 shows a method 2000 of resecting tissue of an organ such as prostatic tissue in accordance with some embodiments, many variations and adaptations can be made as will be readily recognized by one of ordinary skill in the art. For example, some of the steps can be repeated, some of the steps omitted, and the steps can be performed in a different order. Also, other types of tissue as described herein can be treated.

One or more of the steps of method 2000 can be combined with method 1500. For example, a classifier or neural network can be trained with a database of patient treatments. Once the classifier or neural network has been trained, the trained classifier or neural network can be used determine the safety and efficacy parameters of the patient being treated in response to the demographic data, the ultrasound images and the as described with reference to method 2000.

Method 1500 can be used to train a neural network as described herein, either alternatively or in combination with the classifier as described herein.

The processor as described herein can be configured to perform one or more steps of the methods disclosed herein, such as the steps of method 1500 and method 2000.

Figure 21:
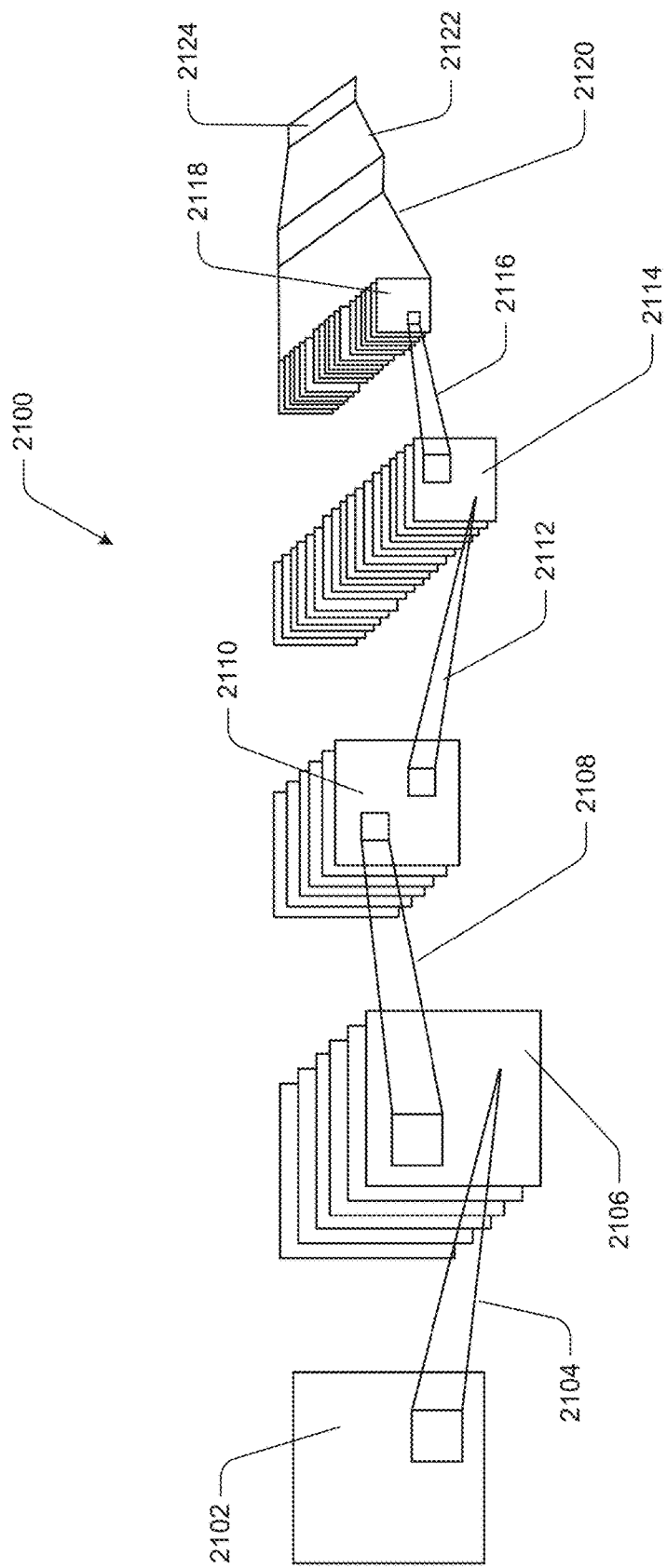
FIG. 21 shows an example convolutional neural network, in accordance with some embodiments.

With reference to FIG. 21, an example of a two-dimensional convolutional neural network 2100 is shown. A dataset 2102 is initially provided, which may include imagery from historical treatment data from prior patients and procedures. A convolution operation 2104 results in data in a 2nd data set 2106, which in turn has a pooling layer 2108 applied to result in a pooled layer 2110 of subsample data in order to further condense the spatial size of the representation. The subsample data may be convoluted 2112 to produce a third data set 2114, which may further have a pooling layer applied 2116 to provide subsample data 2118. The subsample data 2118 may be passed through a first fully connected layer 2120 and a second fully connected layer 2122 to generate a classification matrix output 2124. One or more filters can be applied at each convolution layer to provide different types of feature extraction. After the model is defined, it may be compiled and may utilize accuracy of the feature recognition as a performance metric. The model may be trained over time, such as by using historical procedure data as training data and verified according to the model's predictions, and verified over time until the model's predictions converge with truth data.

Figure 22:
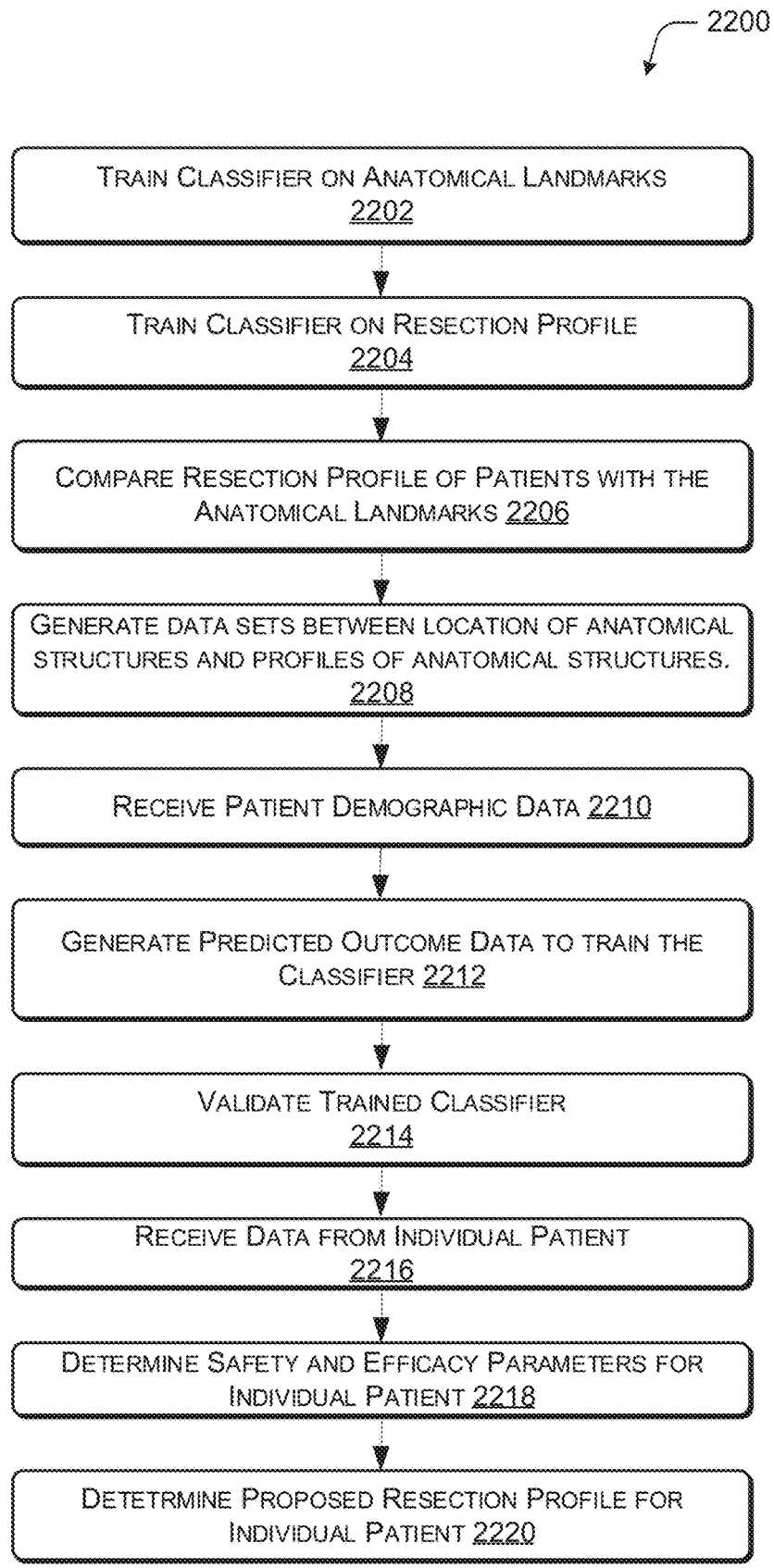
FIG. 22 shows a method of training and using a classifier, in accordance with some embodiments.

FIG. 22 shows a method 2200 of training and using an artificial intelligence or machine learning classifier, in accordance with some embodiments. While the method can be performed in many ways, in some embodiments, a classifier is trained to recognize anatomical landmarks and a plurality of resection profiles associated with the anatomical landmarks. The method includes comparing resection profiles of past patients with the anatomical landmarks and patient data as described herein, such as outcome data and demographic data. The resection profiles may comprise past actual resection profiles overlaid on images from the treatment, or generated and suggested profiles based upon the machine learning algorithms, the weight of the data points, the patient data, among other input types.

Data sets are generated and may be stored in a database comprising historical information, which may comprise a library of actual historical data. The library of patient data can be stored in a database keyed by a unique patient identifier for each patient and associated data for each patient as described herein. The database may comprise a relational database keyed by a unique patient identifier. The historical data stored for each patient may comprise robotics data from the surgery, images from the surgery, pre-operative questionnaire data, post-operative questionnaire data, retreatment data and sexual function data, for each patient of the database. The database may comprise data from any suitable number of patients, such as at least 100 patients, and least 1000 patients, and at least 10,000 patients, and in some embodiments from 10,000 to 1,000,000 patients. Based upon the data input, as described herein, the method utilizes an appropriate model to generate predicted outcome data which is used to train the classifier. The classifier is validated with the data can be through iterative training. The validated classifier is then used to receive input from an actual patient and output useful information, such as a proposed resection profile in response to values of targeted safety and efficacy parameters as described herein. The input data may comprise an image of the patient and the targeted safety and efficacy parameters and other patient data as described herein. Alternatively or in combination, the input data may comprise a target tissue resection profile and values of predicted safety and efficacy parameters as described herein. In some embodiments, the patient data comprises one or more of tensile strength, modulus, elasticity, vascularity, biomarker data, medication history, or genetic data of each patient.

At a step 2202 a classifier is trained on plurality of anatomical landmarks from a plurality of images. This may be performed one or more image analysis algorithms that allow the classifier such as a convolutional neural network to determine anatomical features displayed with the image data. While the classifier can be trained in many ways, in some embodiments a trained professional such as a radiologist or surgeon identifies landmarks and inputs the locations and type of anatomical landmark with a user interface such as a touchpad. The anatomical landmarks may comprise one or more delicate tissue structures as described herein, such as a verumontanum, a retina of an eye, or a tumor, for example. This training can be completed for several images from the library of treatments for example.

At a step 2204, the classifier is trained on a plurality of resection profiles. The resection profile may comprise a target resection profile overlaid on an image as described herein, in which the image has been stored on a database. Alternatively or in combination, the classifier can be trained with user input to identify the resection profile from an image such as an ultrasound image as described herein. For example, the treatment profession can identify locations and the profile of the resection with user input to locations of the images with an input device such as a touchpad, and the user can draw a line of the resection profile with the input device to train the classifier.

At a step 2206, the resection profile is compared with the anatomical landmarks. For example, the distances between resection profile and anatomical landmarks can be compared. The anatomical landmarks may comprise one or more delicate tissue structures as described herein, and the distance between the resection profile and the anatomical landmark compared for each patient of the plurality of patients. In some cases, a resection profile comprises one or more protection zones to protect sensitive tissue structures as described herein. The distances from the protection zone to the delicate tissue structure compared for each of the plurality of patients.

At a step 2208, the method generates data sets between locations of anatomical structures and resection profiles of anatomical structures. This may be based upon actual historical data that indicates the efficacy of treatment based upon the resection profiles.

At a step 2210, the patient demographic data is received. The patient demographic data may include any of a wide number of data types that present information about the patient as described herein. As a non-limiting example, demographic data may include information relating to age, weight, body mass index, medication history, procedure history, flow, sexual function, geography, race, symptoms, diet, family structure, and the like.

At a step 2212, the predicted outcome data is generated and used to train the classifier. For instance, the method may generate predicted outcome data, which may be compared against actual historical data. Where there is an identified gap between the predicted outcome data and the actual outcome data from the historical data, the classifier may be modified, and the training may be iterated until the predicted outcome data matches the actual historical data within a threshold amount.

At a step 2214, the trained classifier is validated. As described, this may be an iterative process that compares predicted data against actual data and the classifier can be modified until the predicted data converges toward the actual data.

At a step 2216, data from an individual patient is received. This may include any of the demographic data described, along with other data types that provides the classifier with sufficient information to generate a resection profile.

At a step 2218, the safety parameters and efficacy parameters are generated for an individual patient. These may be based upon user input or may automatically be generated based upon likely or desired outcome.

At a step 2220, a proposed resection profile is determined for the individual patient. In other words, based upon the input data, the trained classifier generates and outputs a proposed resection profile for an individual patient. The resection profile may be modified as described herein to reduce the amount of resecting or ablative aggression in the protection zones or other zones as described herein. Alternatively, the resection profile can be modified to increase the aggressiveness of the tissue resection The proposed resection profile, the actual resection profile, and the actual procedural outcome can be stored in the database and used to refine the classifier and other machine learning algorithms. The procedural parameters can be recorded for each procedure, and may include any parameter as described herein, such as one or more of a measured treatment time, a measured set up time, a measured imaging time, a measured time the treatment probe moves, a measured intensity of the energy source to remove tissue, a plurality of recorded positions of the treatment probe, a plurality of recorded images of the tissue during treatment, a plurality of recorded orientations of the treatment probe, or a plurality of tissue images corresponding to each of the plurality of recorded positions and orientations. The plurality of treatment parameters recorded during treatment may include a plurality of sequentially arranged data frames, each of the plurality of sequentially arranged data frames comprising an image of the tissue, an image of the treatment probe positioned in relation to the tissue being treated, a position of the treatment probe, an orientation of the treatment probe, or an energy of the treatment probe and optionally wherein each of the plurality of sequentially arranged data frames corresponds to a substantially fixed time interval between said each of the plurality of frames. The values of each of these parameters can be stored in the library of treatments for each of the plurality of patients stored in the database as described herein.

The described artificial intelligence and machine learning system may comprise a processor having instructions configured to perform one or more of artificial intelligence, search and mathematical optimization, artificial neural networks, statistics, probability, support vector machine learning, clustering of data groups, image classification, image segmentation. The instructions may comprise one or more of decision tree learning, association rule learning, artificial neural networks, deep learning, inductive logic programming, support vector machines, clustering, Bayesian networks, reinforcement learning, representation learning, similarity and metric learning, sparse dictionary learning, genetic algorithms, rule-based machine learning, or a learning classifier system.

One or more steps of the method 2200 can be performed with a processor as described herein. One or more steps of the method 2200 may be performed with circuitry or processor instructions as described herein, for example, one or more of a processor or a logic circuitry of the systems described herein. The circuitry may be programmed to provide one or more steps of the method 2200, and the program may comprise program instructions stored on a computer readable memory or programmed steps of the logic circuitry such as with programmable array logic or a field programmable gate array, for example.

FIG. 22 shows a method in accordance with some embodiments. A person of ordinary skill in the art will recognize many variations and adaptations in accordance with the teachings disclosed herein. For example, some of the steps of the method can be removed. Additional steps can be provided. Some of the steps may comprise sub-steps. Some of the steps can be repeated. The order of the steps can be changed.

The convolutional neural network may be used to classify image data, and this, or an alternative machine learning algorithm, may be applied to result in the generation of recommended treatment profiles. The machine learning neural network models may be trained over time by utilizing historical treatment data as well as modifications to the recommended treatment plan output from the model. The result is the generation of a recommended treatment plan that improves over time based upon continuing training of the machine learning model.

The energy source may comprise one or more of mechanical energy, a water jet, electromagnetic energy, laser energy, radiofrequency (RF) energy, radiotherapy (RT) energy, or ultrasound energy, vapor, water vapor, heated water vapor, or any other type of suitable energy source for ablating, resection, or removing tissue, and combinations thereof.

The specification includes the following numbered clauses, which are part of the present disclosure.

Clause 1. An apparatus for robotic surgery, the apparatus comprising: a processor configured with instructions to: receive patient data for each of a plurality of treated patients, the data for each of the plurality of treated patients comprising one or more of patient demographic data, a cut profile of tissue to be removed, an actual profile of tissue removed, a target volume of tissue to be removed, an actual volume of tissue removed, or a ratio of an amount of tissue targeted for removal to an amount removed, receive surgical robotics data for each of the plurality of treated patients, the surgical robotics data comprising a plurality of treatment parameters recorded during treatment, a treatment time, a set up time, an imaging time, a time a treatment probe moves, a plurality of locations and orientations of a treatment probe, a plurality of images of tissue, a plurality of images of the tissue each comprising the treatment probe, or an intensity of an energy source to remove tissue; and output a treatment plan of a patient to be treated in response to the patient data and the surgical robotics data.

Clause 2. The apparatus of clause 1, wherein the instructions further comprise: receive an adjustment to the treatment plan of the patient to be treated, wherein the adjustment to the treatment plan of the patient to be treated comprises an adjustment to one or more of a cut profile of tissue to be removed, an actual profile of tissue removed, a target volume of tissue to be removed, an actual volume of tissue removed, a treatment time, a set up time, an imaging time, time a treatment probe moves, an intensity of an energy source to remove tissue, or a ratio of an amount of tissue targeted for removal to an amount removed.

Clause 3. The apparatus of clause 2, wherein the cut profile comprises a plurality of locations comprising a plurality of angular coordinates about a treatment axis, a plurality of corresponding axial coordinates along the axis, and a plurality of radial distances from the axis and wherein an adjustment to the cut profile comprises an adjustment to the plurality of angular coordinates about the treatment axis, the plurality of corresponding axial coordinates along the axis, or the plurality of radial distances from the axis.

Clause 4. The apparatus of clause 1, wherein the processor is configured with instructions to display an initial cut profile overlaid on an image of tissue to be resected on a display and to display an adjusted cut profile on the image of the tissue to be treated.

Clause 5. The apparatus of clause 1, wherein the plurality of treatment parameters recorded during treatment comprises a measured treatment time, a measured set up time, a measured imaging time, a measured time the treatment probe moves, a measured intensity of the energy source to remove tissue, a plurality of recorded positions of the treatment probe, a plurality of recorded images of the tissue during treatment, a plurality of recorded orientations of the treatment probe, a plurality of tissue images corresponding to each of the plurality of recorded positions and orientations.

Clause 6. The apparatus of clause 5, wherein the plurality of treatment parameters recorded during treatment comprises a plurality of sequentially arranged data frames, each of the plurality of sequentially arranged data frames comprising an image of the treatment probe positioned in relation to the tissue being treated, a position of the treatment probe, an orientation of the treatment probe, or an energy of the treatment probe and optionally wherein each of the plurality of sequentially arranged data frames corresponds to a substantially fixed time interval between said each of the plurality of frames.

Clause 7. The apparatus of any one of the preceding clauses, wherein the patient demographic data for each of the plurality of patients and the patient to be treated comprises one or more of patient age, weight, sex, body mass index, race, geography, diet, or family structure.

Clause 8. The apparatus of clause 1, wherein the intensity of the energy source comprises a water jet intensity, an optical beam intensity, a radio frequency energy intensity, an ionizing radiation intensity, a stereotactic radiation intensity, or an ultrasonic energy intensity.

Clause 9. The apparatus of clause 1, wherein the treatment plan of the patient to be treated in response to the patient data and the surgical robotics data is determined with processor instructions comprising one or more of artificial intelligence or machine learning.

Clause 10. The apparatus of clause 9, wherein the treatment plan is determined with the artificial intelligence processor instructions and wherein the artificial intelligence processor instructions comprise one or more of machine learning, search and mathematical optimization, artificial neural networks, statistics, probability, support vector machine learning, clustering of data groups, image classification, or image segmentation.

Clause 11. The apparatus of clause 9, wherein the treatment plan is determined with the machine learning processor instructions and wherein the machine learning processor instructions comprise one or more of decision tree learning, association rule learning, artificial neural networks, deep learning, inductive logic programming, support vector machines, clustering, Bayesian networks, reinforcement learning, representation learning, similarity and metric learning, sparse dictionary learning, genetic algorithms, rule based machine learning or a learning classifier system.

Clause 12. The apparatus of clause 11, wherein the instructions further cause the processor to receive human interaction to provide input to one or more of select AI approaches using one or more of a plurality of AI tools, select visualization of different recommended treatment plans, or change an importance of data used to generate the treatment plan.

Clause 13. The apparatus of anyone of the preceding clauses wherein the artificial intelligence or machine learning is trained on the patient data for each of the plurality of treated patients and the surgical robotics data for each of the plurality of treated patients and the treatment plan of the patient to be treated is determined in response to the artificial intelligence or machine learning trained in response to the treated patient data and the surgical robotics data.

Clause 14. The apparatus of any one of the preceding clauses wherein the target volume of tissue to be removed comprises a total volume of tissue targeted for removed and the actual volume of tissue removed comprises an actual total volume of tissue removed.

Clause 15. The apparatus of any one of the preceding clauses wherein the artificial intelligence ("AI") or machine learning is configured to train the AI or machine learning algorithm on a plurality of treatment plans and patient outcomes (optionally based on physician or patient reported info) of the plurality of treated patients and determine the treatment plan of the patient to be treated.

Clause 16. The apparatus of clause 15, wherein the plurality of treatment plans to be treated is coupled to corresponding outcomes comprising one or more of quality of life score, sexual function, durability of treatment or flow rates, and wherein the AI or machine learning is configured to provide semi-automated planning to optimize treatment contours based on patient's prostate anatomy of a patient to be treated.

Clause 17. The apparatus of any one of the preceding clauses wherein outcome data of the plurality of treated patients is used as input to train the AI or machine learning classifier and optionally wherein the outcome data comprises one or more of hemoglobin loss, complications, pain scores, return to work time, uroflow data, catheterization time, hospital stay, days to continence, hemostasis method, sexual function measures, balloon model, balloon technique, catheter tension, Foley catheter tension, catheter tensioning device method, surgeon case notes, anesthesia used, pain med usage, or urodynamics before and after and optionally wherein the AI or machine learning is configured to perform calculations to determine and adjusted treatment plan to improve critical outcomes measures and optionally wherein the adjusted treatment plan comprises an adjusted treatment profile and optionally wherein the adjusted treatment profile comprises an optimized treatment profile.

Clause 18. The apparatus of any one of the preceding clauses wherein the AI or machine learning is trained to auto-adjust a depth of penetration based on image recognition of imaging parameters of tissue images during treatment of a patient during treatment in response to the AI or machine learning trained on a plurality of treated patients and optionally wherein the auto adjustment comprises an intended depth of penetration comparted to an actual depth of penetration and wherein the AI or machine learning is configured to auto-adjust a cut profile if mismatched or vary intensity of source based on tissue density.

Clause 19. The apparatus of clause 18, wherein the cut profile is adjusted in response to a value of a biomechanical tissue parameter measured from the patient.

Clause 20. The apparatus of any one of the preceding clauses wherein the AI or machine learning is trained with baseline data comprising a library of many ultrasound images from charts with peer reviewed identification of organ tissue planes and anatomical features identified such as prostate capsule, bladder neck, sphincter, veru, ducts, medial lobe, lateral lobes and wherein the AI or machine learning is configured to provide physician assisted guidance of a patient to be treated in response to data of the patient to be treated and the AI or machine learning trained with the baseline data.

Clause 21. An apparatus for determining a tissue removal profile for a prostate surgery of a patient having a verumontanum, the apparatus comprising: a processor configured with instructions to: display an image of a prostate; display a tissue removal profile on the image of the prostate; and display one or more of an efficacy parameter, a probability of decreased sexual function, or a probability of retreatment of the prostate with the cut profile and the image of the prostate.

Clause 22. The apparatus of clause 21, wherein the processor comprises instructions to receive a digital signature from the patient accepting the one or more of the efficacy parameter, the probability of decreased sexual function or the probability of retreatment.

Clause 23. The apparatus of clause 22, wherein the processor comprises instructions to display the digital signature with the image of the prostate, the one or more of the cut profile, the efficacy parameter, the probability of decreased sexual function or the probability of retreatment.

Clause 24. An apparatus for determining a treatment plan for a prostate surgery of a patient having a verumontanum, the apparatus comprising: a processor configured with instructions to: receive user input comprising a sexual importance parameter corresponding to an importance of sexual activity to the patient and an acceptance parameter corresponding the patient's tolerance of a second prostate surgery of the patient; and output the treatment plan, wherein the treatment plan comprises instructions to remove tissue to a distance from the verumontanum, the distance farther from the verumontanum when the sexual importance parameter corresponds to increased importance of sexual activity and the acceptance parameter corresponds to increased acceptance of the second prostate surgery procedure, the distance closer to the verumontanum when the sexual activity parameter corresponds to decreased importance of sexual activity and acceptance of the second prostate surgery procedure.

Clause 25. The apparatus of clause 24, wherein the treatment plan comprises a tissue removal profile and the processor comprises instructions to generate the tissue removal profile in response to the user input.

Clause 26. The apparatus of clause 25, wherein the tissue removal profile comprises a distance to the verumontanum and the distance increases with increased importance and acceptance and decreases with decreased importance and acceptance.

Clause 27. The apparatus of clause 24, wherein the processor comprises instructions to display a tissue removal profile on an image of the prostate and optionally wherein the image comprises an image of the prostate of the patient.

Clause 28. The apparatus of clause 27, wherein the image comprises one or more of ultrasound imaging, magnetic resonance imaging, computed tomography (CT) scan imaging, or cystoscopy imaging.

Clause 29. The apparatus of clause 28, wherein the ultrasound imaging comprises one or more of pulse ultrasound, echo ultrasound, doppler ultrasound, or sheer wave elasticity imaging.

Clause 30. The apparatus of clause 27, wherein the image of the prostate comprises one or more of a sagittal image or a transverse image of the prostate.

Clause 31. The apparatus of clause 30, wherein the image of the prostate further comprises one or more of a parasagittal image, coronal image, paracoronal image, or a three-dimensional image.

Clause 32. The apparatus of clause 27, wherein the image comprises a verumontanum of a prostate and optionally wherein the verumontanum of the prostate comprises an image of the verumontanum of the patient.

Clause 33. The apparatus of clause 27, wherein the processor comprises instructions to move the removal profile shown on the display farther from a verumontanum in response to increased importance and increased acceptance and closer to a verumontanum in response to decreased importance and increased acceptance.

Clause 34. The apparatus of clause 24, wherein the processor comprises instructions to receive a ranking parameter corresponding to a ranking of the importance of sexual activity in relation to the acceptance of the second prostate surgery and wherein the distance to the verumontanum increases with increased importance of sexual activity and decreased acceptance of the second prostate surgery in response to the ranking parameter indicating sexual activity corresponds to greater importance than acceptance of the second prostate surgery and wherein the distance to the verumontanum decreases with increased importance of sexual activity and decreased acceptance of the second prostate surgery in response to the raking parameter indicating sexual activity corresponds to lesser importance than acceptance of the second procedure.

Clause 35. The apparatus of clause 24, wherein the processor comprises instructions to generate a first prostate tissue removal profile in response to a first importance of sexual activity and a first acceptance of the second prostate surgery and a second prostate tissue removal profile in response to a second sexual importance of sexual activity and a second acceptance of the second prostate surgery.

Clause 36. The apparatus of clause 35, wherein the first prostate tissue removal profile comprises a first distance to the verumontanum along the first prostate tissue removal profile and the second prostate tissue removal profile comprises a second distance to the verumontanum along the second prostate tissue removal profile.

Clause 37. The apparatus of clause 36, wherein the first distance is greater than the second distance when the first importance and the first acceptance are less than the second importance and the second acceptance and the first distance is less than the second distance when the first importance and the first acceptance are less than the second importance and the second acceptance.

Clause 38. The apparatus of clause 37, wherein the processor comprises instructions to generate treatment instructions to move a source of energy in accordance with the treatment plan to remove the prostate tissue to the first distance or the second distance in response to the user inputting the first importance and the first acceptance or the second importance and the second acceptance.

Clause 39. An apparatus to resect tissue of an organ of a patient, the apparatus comprising: a display; a processor operatively coupled to the display, the processor configured with instructions to, receive one or more of a safety or an efficacy parameter for the patient, receive an image of the organ, determine a resection profile of the organ in response to the image and the one or more of the safety or the efficacy parameter, and display the resection profile with the image on the display.

Clause 40. The apparatus of clause 39, wherein the organ comprises a delicate tissue structure and the resection profile comprises a protection zone, and the protection zone of the removal profile is determined in response to the image of the organ and the one or more of the safety profile or the efficacy profile.

Clause 41. The apparatus of clause 40, wherein the organ comprises a prostate and the delicate tissue structure comprises a verumontanum of the prostate.

Clause 42. The apparatus of clause 40, wherein the delicate tissue structure comprises cancerous tissue.

Clause 43. The apparatus of clause 40, wherein the protection zone is one of a plurality of protection zones, and the plurality of protection zones of the removal profile are determined, at least in response, to the image of the organ and the one or more of the safety profile or the efficacy profile.

Clause 44. The apparatus of clause 43, wherein one or more of the plurality of protection zones are associated with a resection profile determined, at least in part, based on one or more of avoiding damage to delicate tissue structures or avoiding disbursement of pathogenic tissue.

Clause 45. The apparatus of clause 40, wherein the image of the organ is shown on the display with the resection profile in a sagittal view and a transverse view, and resection profile comprises a three-dimensional volumetric resection profile.

Clause 46. The apparatus of clause 40, wherein the processor is configured with instructions to display the image of the organ with the resection profile in one or more of a sagittal view, parasagittal view, a transverse view, a coronal view, a paracoronal view, or a three-dimensional view.

Clause 47. The apparatus of clause 46, wherein the processor is configured with instructions to display the safety parameter and the efficacy parameter on the display.

Clause 48. The apparatus of clause 46, wherein the processor is configured with instructions to receive a user input to adjust the resection profile shown on the display to generate an adjusted resection profile and determine a second values of the one or more of safety or efficacy parameters on the display in response to the user adjusted resection profile.

Clause 49. The apparatus of clause 39, wherein the processor is configured with instructions to display the safety parameter and the efficacy parameter on the display.

Clause 50. The apparatus of clause 39, wherein the processor is configured with instructions to display a value of a target safety parameter, value of a target efficacy parameter, an adjusted safety parameter and an adjusted efficacy parameter, wherein the adjusted safety parameter and the adjusted efficacy parameter are updated in real time and shown on the display in response to the user adjusting the resection profile.

Clause 51. The apparatus of clause 39, wherein the organ comprises a prostate and the processor is configured with instructions to identify a location of a verumontanum of the prostate.

Clause 52. The apparatus of clause 39, wherein the image of the organ comprises one or more of tissue margin identification, tissue plane identification, tissue differentiation detection, fluoroscopy, CT scan imaging, magnetic resonance imaging, radioactivity detection, or radiopaque imaging.

Clause 53. An apparatus to resect tissue of an organ of a patient, the apparatus comprising: a display; a processor operatively coupled to the display, the processor configured with instructions to, receive an image of the organ, receive a resection profile of the organ, and display a value of one or more of a safety parameter or an efficacy parameter in response to the resection profile and the image.

Clause 54. The apparatus of clause 53, wherein the organ comprises a delicate tissue structure and the processor is configured with instructions to determine a location of the delicate tissue structure in relation to the resection profile and to display the value of the one or more of the safety parameter or the efficacy parameter in response to the location of the delicate tissue structure and the removal profile.

Clause 55. The apparatus of clause 54, wherein the organ comprises a prostate and the delicate tissue structure comprises a verumontanum of the prostate.

Clause 56. The apparatus of clause 54, wherein the delicate tissue structure comprises cancerous tissue.

Clause 57. The apparatus of clause 54, wherein the resection profile comprises one or more protection zones determined, at least in part, based upon one or more of decreasing damage to the delicate tissue structure or avoiding disbursement of pathogenic tissue.

Clause 58. The apparatus of clause 53, wherein the image of the organ is shown on the display with the resection profile in a sagittal view and a transverse view, and resection profile comprises a three dimensional volumetric resection profile.

Clause 59. The apparatus of clause 53, wherein the processor is configured with instructions to display the image of the organ overlaid with the resection profile in a sagittal view and a transverse view.

Clause 60. The apparatus of clause 59, wherein the processor is configured with instructions to display the safety parameter and the efficacy parameter on the display.

Clause 61. The apparatus of clause 53, wherein the processor is configured with instructions to receive a user input to adjust the resection profile shown on the display to generate an adjusted resection profile and determine a second values of the one or more of safety or efficacy parameters on the display in response to the user adjusted resection profile.

Clause 62. The apparatus of clause 53, wherein the processor is configured with instructions to display the safety parameter and the efficacy parameter on the display.

Clause 63. The apparatus of clause 53, wherein the processor is configured with instructions to display a value of a target safety parameter, a value of a target efficacy parameter, an adjusted safety parameter and an adjusted efficacy parameter, wherein the adjusted safety parameter and the adjusted efficacy parameter are updated in real time and shown on the display in response to the user adjusting the resection profile.

Clause 64. The apparatus of clause 53, wherein the organ comprises a prostate and the processor is configured with instructions to identify a location of a verumontanum of the prostate.

Clause 65. An apparatus as in any one of the preceding clauses wherein the resection profile comprises a cut profile.

Clause 66. An apparatus as in any one of the preceding clauses wherein an energy source to resect tissue to a resection profile comprises one or more of mechanical energy, a water jet, electromagnetic energy, laser energy, radiofrequency (RF) energy, radiotherapy (RT) energy, ultrasound energy, vapor, water vapor energy, heated water vapor energy, or steam energy.

Clause 67. The apparatus as in any one of the preceding clauses wherein the patient data comprises one or more of tensile strength, modulus, elasticity, vascularity, biomarker data or genetic data.

Clause 68. An apparatus as in any one of the preceding clauses, wherein the processor is configured with instructions for the user to select one or more parameters used to determine one or more of a safety parameter value, an efficacy parameter value or a proposed tissue resection profile.

Clause 69. An apparatus as in any one of the preceding clauses, wherein the processor is configured with instructions for a user to plan a surgery on a first display remote from a surgery system, store parameters for the planned surgery, and provide parameters to a processor operatively coupled to a display of a surgical system.

Clause 70. A method of robotics surgery, the method comprising performing a step of the processor instructions of any one of the preceding clauses.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus to treat tissue of a prostate of a patient, the apparatus comprising:
a display;
a processor operatively coupled to the display; and
memory comprising instructions that when executed by the processor, cause the apparatus to,
receive an image of the prostate,
identify delicate a tissue structure of the prostate based on the image, and
generate, using a trained classifier, a treatment plan for treating a lobe of the prostate, the treatment plan including a tissue removal profile for the lobe of the prostate,
display the tissue removal profile on the display,
receive a user input to adjust the tissue removal profile shown on the display to generate an adjusted tissue removal profile.

2. The apparatus of claim 1, wherein the memory comprises the instructions that further cause the apparatus to determine a location of the delicate tissue structure in relation to the tissue removal profile and to display a value of the one or more of a safety parameter or an efficacy parameter.

3. The apparatus of claim 2, wherein the tissue removal profile comprises one or more protection zones determined based, at least in part, upon one or more of decreasing damage to the delicate tissue structure or avoiding disbursement of a pathogenic tissue.

4. The apparatus of claim 3, wherein the prostate comprises a delicate tissue structure and the tissue removal profile comprises a protection zone, and the protection zone of the tissue removal profile is determined in response to the image of the prostate and the one or more of the safety parameter or the efficacy parameter.

5. The apparatus of claim 4, wherein the protection zone is one of a plurality of protection zones, and the plurality of protection zones of the tissue removal profile are determined, at least in response, to the image of the prostate and the one or more of the safety parameter or the efficacy parameter.

6. The apparatus of claim 5, wherein one or more of the plurality of protection zones are determined, at least in part, based on one or more of avoiding damage to delicate tissue structures or avoiding disbursement of the pathogenic tissue.

7. The apparatus of claim 2, wherein the safety parameter and the efficacy parameter are generated with a classifier.

8. The apparatus of claim 1, wherein the delicate tissue structure comprises a verumontanum of the prostate.

9. The apparatus of claim 1, wherein the delicate tissue structure comprises cancerous tissue.

10. The apparatus of claim 1, wherein the trained classifier is a trained neural network.

11. The apparatus of claim 1, wherein the trained classifier is a trained artificial intelligence network.

12. The apparatus of claim 1, wherein instructions to identify delicate tissue structures of the prostate based on the image include instructions to identify, using the trained classifier, the delicate tissue structures of the prostate within the image.

13. The apparatus of claim 1, wherein the tissue removal profile includes a cut profile.

14. The apparatus of claim 13, wherein the cut profile includes a plurality of locations comprising a plurality of angular coordinates about a treatment axis, a plurality of corresponding axial coordinates along the treatment axis, and a plurality of radial distances from the treatment axis.

15. The apparatus of claim 14, wherein the memory comprises instructions that further cause the apparatus to adjust the cut profile based on the use input.

16. The apparatus of claim 15, wherein the instructions to adjust the cut profile further include instructions to adjust at least one of:
the plurality of angular coordinates about the treatment axis,
the plurality of corresponding axial coordinates along the axis, or
the plurality of radial distances from the axis.

17. The apparatus of claim 1, wherein the instructions to identify the delicate tissue structures of the prostate based on the image includes instructions to identify the delicate tissue structures of the prostate with a trained convolutional neural network.

18. The apparatus of claim 1, wherein the instructions to identify the delicate tissue structures of the prostate based on the image includes instructions to identify the delicate tissue structures of the prostate using edge detection, feature recognition, or segmentation.

19. The apparatus of claim 1, wherein the instructions to display the tissue removal profile on the display further include instructions to display the image of the prostate with the tissue removal profile in one or more of a sagittal view, parasagittal view, a transverse view, a coronal view, a paracoronal view, or a three-dimensional view.

20. The apparatus of claim 1, wherein the image of the prostate comprises one or more of tissue margin identification, tissue plane identification, tissue differentiation detection, fluoroscopy, CT scan imaging, magnetic resonance imaging, radioactivity detection, or radiopaque imaging.

* * * * *